United States Patent
Suwa et al.

(10) Patent No.: US 8,058,009 B2
(45) Date of Patent: Nov. 15, 2011

(54) TARGET PROTEIN AND TARGET GENE IN DRUG DESIGNING AND SCREENING METHOD

(75) Inventors: Yorimasa Suwa, Hino (JP); Tadakazu Yamauchi, Gotenba (JP); Tsuyoshi Yamada, Suita (JP); Hironori Oosaki, Tsukuba (JP); Morikazu Kito, Kawasaki (JP)

(73) Assignee: Reverse Proteomics Research Institute Co., Ltd., Tokyo (JP)

( * ) Notice: Subject to any disclaimer, the term of this patent is extended or adjusted under 35 U.S.C. 154(b) by 959 days.

(21) Appl. No.: 11/718,946

(22) PCT Filed: Nov. 9, 2005

(86) PCT No.: PCT/JP2005/020989
§ 371 (c)(1),
(2), (4) Date: Oct. 24, 2007

(87) PCT Pub. No.: WO2006/052000
PCT Pub. Date: May 18, 2006

(65) Prior Publication Data
US 2008/0102457 A1    May 1, 2008

(30) Foreign Application Priority Data
Nov. 9, 2004 (JP) .................................. 2004-325537

(51) Int. Cl.
*G01N 33/53* (2006.01)
(52) U.S. Cl. .......................................... 435/7.1; 435/7.8

(58) Field of Classification Search .................... None
See application file for complete search history.

(56) References Cited

U.S. PATENT DOCUMENTS
2002/0119929 A1    8/2002    Bishop et al.
2004/0115726 A1    6/2004    Nagashima et al.

FOREIGN PATENT DOCUMENTS
JP    2004-509406 A    3/2004
WO    WO 03/087768 A2    10/2003

OTHER PUBLICATIONS

Brown et al., *Drug Discovery Today*, 8(23): 1067-1077 (Dec. 2003).
Dimasi, *Clinical Pharmacology & Therapeutics*, 69(5): 297-307 (May 2001).
Drews, *Science*, 287: 1960-1964 (Mar. 17, 2000).
Frantz et al., *Nature Reviews*, 2: 95-96 (Feb. 2003).
Fujii et al., *Chem-Bio Informatics Journal*, 1(1): 18-22 (2001).
Hopkins et al., *Nature Reviews*, 1: 727-730 (Sep. 2002).

*Primary Examiner* — Daniel C Gamett
(74) *Attorney, Agent, or Firm* — Leydig, Voit & Mayer, Ltd.

(57) ABSTRACT

The present invention provides target proteins and target genes for bioactive substances such as drugs, and means that enable the development of novel bioactive substances using the same. To be specific, the present invention provides target proteins and target genes for bioactive substances; screening methods for substances capable of regulating bioactivities; bioactivity regulators; a bioactive substance derivative production method; a complex comprising a bioactive substance and a target protein, and a method of producing the complex; and kits comprising a bioactive substance or a salt thereof; determination methods for the onset or risk of onset of a specified disease or condition, determination methods for susceptibility to a bioactive substance, and determination kits used for the determination methods, and the like.

4 Claims, No Drawings

TARGET PROTEIN AND TARGET GENE IN DRUG DESIGNING AND SCREENING METHOD

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 69,673 bytes ASCII (Text) file named "701603SequenceListing.txt," created May 8, 2007.

TECHNICAL FIELD

The present invention relates to target proteins and target genes that are useful for the development of bioactive substances, for example, drug discovery; a screening method for a bioactive substance and the substance obtained by the screening method; a bioactivity regulator; a bioactive substance derivative and a method of producing the derivative; and a complex comprising a bioactive substance and a target protein therefor and a method of producing the complex, and the like.

PRIOR ART

Traditionally, the success rate of new drug research and development is quite low, with only one or two of about 100 research projects ending successfully with the launch of a new drug (D. Brown and G. Superti-Furga, Drug Discovery Today, December, 2003). This is mostly because of premature termination of the development due to a problem with the economy, safety or efficacy of the new drug candidate compound (Dimasi, Clin. Pharmacol. Ther., 69, 297-307, 2001).

Pharmaceutical companies are spending 10 to 20% of their sales on R&D activities; it is of paramount importance to efficiently spend R&D budgets for pharmaceutical companies to be highly competitive. Furthermore, because about 80% of R&D expenditures are spent for costly clinical studies in the developmental stage, it is critical to select appropriate candidate compounds in the initial stage prior to progress to the developmental stage.

In recent years, on the other, the genome sequences of a variety of organisms have been elucidated and analyzed at the global level. For the human genome, in particular, a worldwide cooperative research project was implemented, and completion of analysis of all sequences thereof was announced in April 2003. As a result, it is becoming possible to analyze complex biological phenomena in the context of the functions and control of all genes, or networks of gene-gene, protein-protein, cell-cell, and individual-individual interactions. The genome information thus obtained has been significantly revolutionizing a number of industries, including drug development, as well as in academic sectors.

For example, it has been reported that there are about 480 kinds of target proteins for drugs having been in common use to date, and that these target proteins are limited to membrane receptors, enzymes, ion channels, or nuclear receptors and the like (J. Drews, Science, 297, 1960-1964, 2000). Meanwhile, target protein search based on genome information has discovered an extremely large number of target proteins, including novel proteins not covered in the conventional range of target proteins one after another, which are estimated to total about 1,500 kinds (A. L. Hopkins & C. R. Groom, Nature Reviews; Drug Discovery, 1, 727-730, 2002).

However, despite the fact that the research and development expenditures spent by pharmaceutical companies are increasing due to rises in infrastructuring costs for coping with vast amounts of data like genome information and clinical developmental costs, the number of new drugs approved is tending to decrease on the contrary (Nature Reviews; Drug Discovery, February, 2003). This shows that the above-described genome information is actually not efficiently utilized.

As a means for overcoming these circumstances, Nagashima et al. invented "Method, System, Apparatus, and Device for Discovering and Preparing Chemical for Medical and Other Uses" and filed a patent application for that invention (National Publication of Translated Version No. 2004-509406).

Disclosed in that patent application are methods, systems, databases, user interfaces, software, media, and services that are useful for the evaluation of compound-protein interactions, and are also useful for the utilization of the information resulting from such an evaluation intended to discover compounds in medical and other areas. Furthermore, it is intended to produce a very large pool of novel target proteins for drug discovery, novel methods for designing novel drugs, and a pool of small substances for therapeutic purposes that are virtually synthesized as having been inconceivable in the past.

Specifically, disclosed in that patent application were a method of identifying a protein or partial protein that is appropriate as a novel drug discovery target, which comprises the following steps:
(i) a step for selecting a plurality of proteins or partial proteins showing desired affinity and specificity for a selected target compound;
(ii) a step for identifying the structure and function of the protein or the partial protein; and
(iii) a step for selecting a single protein or single partial protein having a desired function, and a method of discovering a drug, which comprises the following steps:
(i) a step for investigating the chemical structure of the target compound selected using the above-described method; and
(ii) a step for chemically modifying the structure of the selected target compound to optimize the affinity and specificity of the modified compound for the protein or the partial protein, which is appropriate as a novel drug target.

Furthermore, another feature of the method disclosed in that patent application resides in that the selected target compound is a compound approved for medical use.

Conventional drugs that have been used to date include many drugs for which target proteins are unknown, or for which target proteins are known but not all of whose pharmacological effects and adverse effects can be explained by mechanisms mediated by the proteins.

Typically, aspirin, one of the drugs that have longest been used, may be mentioned. When aspirin was launched in the market for the first time more than 100 years ago, the mechanism for its anti-inflammatory action was unclear. About 70 years later, aspirin was found to have cyclooxygenase (COX) inhibitory action. Still 20 years later, it was demonstrated that COX occurred in two subtypes: COX-1 and COX-2, that the primary pharmacological effect of aspirin was based on COX-2 inhibition, and that COX-1 inhibitory action was the cause of adverse effects such as gastrointestinal disorders. However, not all the target proteins for aspirin have been elucidated. In recent years, aspirin has been shown to exhibit anticancer action and antidementic action in clinical settings, but these pharmacological effects cannot be explained by COX inhibition. On the other hand, recent years have seen many papers reporting that aspirin acts on transcription factors such as IKKβ and on nuclear receptors such as PPAR-γ, but the association of these and the various pharmacological effects of aspirin remains unclear.

For these reasons, elucidating target proteins for traditionally used drugs can be said to be a very effective approach to discovering novel drug discovery target proteins.

Hirayama, one of the inventors of the above-described published patent, and others generated a database integrating the structural and physical property data on about 1,500 kinds of drugs commercially available in Japan, and found that existing pharmaceutical compounds share structural features (Chem-Bio Informatics Journal, 1, 18-22, 2001). Drugs that have been commonly used to date can be described as excellent in that they have cleared the issues of localization in the body and safety in their developmental processes. Searching novel target proteins with these existing drugs as probes, and selecting novel new drug candidate compounds on the basis of their structures is thought to be a highly reasonable and efficient approach.

A second problem arises concerning how to make use of the genome information during the search for novel target proteins. Solely determining the genome sequence is not sufficient to ensure the elucidation of the functions of all genes and the discovery of drug discovery target proteins. It is estimated that in humans, about 30,000 to 40,000 kinds of genes are present; taking into consideration variants from alternative splicing, there are reportedly more than 100,000 kinds of mRNA. It is important, therefore, that out of the vast amount of new genes revealed from the genome sequence, those having useful functions in industrial applications, including drug development, should be efficiently selected and identified.

In the genome sequences of eukaryotic organisms, each gene is divided into a plurality of exons by introns; therefore, it is impossible to accurately predict the structure of the protein encoded by the gene solely from the sequence information on the gene. In contrast, for a cDNA prepared from intron-excluded mRNA, information on the amino acid sequence of protein is obtained as information on a single continuous sequence, enabling easy determination of the primary structure thereof.

In particular, analyzing a full-length cDNA enables the identification of the mRNA transcription initiation point on the genome sequence based on the 5'-terminal sequence of the cDNA, and also enables analysis of the stability of mRNA contained in the sequence and of factors involved in expression control in the translation stage. Also, because the ATG codon, which serves as the translation initiation point, is present on the 5' side, translation into protein in the right frame can be achieved. Therefore, by using an appropriate gene expression system, it is also possible to mass-produce the protein encoded by the cDNA, and to express the protein and analyze the biological activity thereof. Hence, it is considered that by performing an analysis using a protein expressed from full-length cDNA, important information that could not be obtained solely by genome sequence analysis is obtained, and that it is possible to discover novel target proteins that do not lie in the conventional category of drug discovery target proteins.

DISCLOSURE OF THE INVENTION

The objects of the present invention are to provide target proteins and target genes for the development of bioactive substances (e.g., drug discovery), and various means that enable the development of novel bioactive substances using the same and the like.

The present inventors diligently investigated new target proteins that can be useful for the development of bioactive substances by analyzing interactions between human proteins and drugs or compounds that have been used as bioactive substances by means of surface plasmon resonance, and found novel target proteins and novel target genes that are useful for the development of bioactive substances, for example, drug discovery. The present inventors conducted further investigations based on this finding, conceived that substances that regulate the expression or function of these genes are capable of regulating various bioactivities, and that substances capable of regulating various bioactivities are developed by screening substances that regulate the expression or function of these genes, and by derivatizing these bioactive substances so that the expression or function of the target genes therefor can be regulated, and the like, and completed the present invention.

Accordingly, the present invention is as follows:

[1] A screening method for a substance capable of regulating an action associated with bioactive substance X, which comprises determining whether or not a test substance is capable of regulating the expression or function of target protein Y or a gene that encodes the protein, wherein the combination of the bioactive substance X and the target protein Y is any of the following (a1) to (a8):

(a1) a combination of cefaclor and a protein containing the amino acid sequence shown by SEQ ID NO:2, SEQ ID NO:6, SEQ ID NO:8 or SEQ ID NO:12;

(a2) a combination of ubenimex and a protein containing the amino acid sequence shown by SEQ ID NO:2;

(a3) a combination of aclarubicin and a protein containing the amino acid sequence shown by SEQ ID NO:4;

(a4) a combination of cefadroxil and a protein containing the amino acid sequence shown by SEQ ID NO:6;

(a5) a combination of ursolic acid and a protein containing the amino acid sequence shown by SEQ ID NO:10;

(a6) a combination of dicloxacillin and a protein containing the amino acid sequence shown by SEQ ID NO:14;

(a7) a combination of ketanserin and a protein containing the amino acid sequence shown by SEQ ID NO:16;

(a8) a combination of ampicillin and a protein containing the amino acid sequence shown by SEQ ID NO:18.

[2] The method of [1] above, which comprises the following steps (a) to (c):

(a) a step for bringing the test substance into contact with the target protein Y;

(b) a step for measuring the functional level of the protein in the presence of the test substance, and comparing said functional level with the functional level of the protein in the absence of the test substance;

(c) a step for selecting a test substance that alters the functional level of the protein on the basis of the result of the comparison in (b) above.

[3] The method of [1] above, which comprises the following steps (a) to (c):

(a) a step for bringing the test substance into contact with cells allowing a measurement of the expression of target protein Y or a gene encoding the target protein Y;

(b) a step for measuring the expression level of the gene in cells in contact with the test substance, and comparing said expression level with the expression level of the gene in control cells not in contact with the test substance;

(c) a step for selecting a test substance that regulates the expression level of the gene on the basis of the result of the comparison in (b) above.

[4] The method of [1] above, which comprises the following steps (a) to (c):

(a) a step for bringing the test substance into contact with the target protein Y or a mutant protein thereof having a binding ability to bioactive substance X;

(b) a step for measuring an ability of the test substance to bind to the protein;

(c) a step for selecting a test substance capable of binding to the protein on the basis of the result from (b) above.

[5] The method of [1] above, which comprises the following steps (a) to (c):
(a) a step for bringing the test substance and a target protein Y-binding substance into contact with the target protein Y or a mutant protein thereof having a binding ability to bioactive substance X;
(b) a step for measuring the binding level of the target protein Y-binding substance to the protein in the presence of the test substance, and comparing said level with the binding level of the target protein Y-binding substance to the protein in the absence of the test substance;
(c) a step for selecting a test substance that alters the binding level of the target protein Y-binding substance to the protein on the basis of the result of the comparison in (b) above.

[6] A screening method for a substance capable of regulating a function associated with target protein Y, which comprises determining whether or not a test substance is capable of regulating the bindability of bioactive substance X to target protein Y or a mutant protein thereof capable of binding to bioactive substance X,
wherein the combination of target protein Y and bioactive substance X is any of the following combinations (b1) to (b9):
(b1) a combination of a protein containing the amino acid sequence shown by SEQ ID NO:2 and cefaclor, ubenimex or a derivative thereof capable of binding to the protein;
(b2) a combination of a protein containing the amino acid sequence shown by SEQ ID NO:4 and aclarubicin or a derivative thereof capable of binding to the protein;
(b3) a combination of a protein containing the amino acid sequence shown by SEQ ID NO:6 and cefaclor, cefadroxil or a derivative thereof capable of binding to the protein;
(b4) a combination of a protein containing the amino acid sequence shown by SEQ ID NO:8 and cefaclor or a derivative thereof capable of binding to the protein;
(b5) a combination of a protein containing the amino acid sequence shown by SEQ ID NO:10 and ursolic acid or a derivative thereof capable of binding to the protein;
(b6) a combination of a protein containing the amino acid sequence shown by SEQ ID NO:12 and cefaclor or a derivative thereof capable of binding to the protein;
(b7) a combination of a protein containing the amino acid sequence shown by SEQ ID NO:14 and dicloxacillin or a derivative thereof capable of binding to the protein;
(b8) a combination of a protein containing the amino acid sequence shown by SEQ ID NO:16 and ketanserin or a derivative thereof capable of binding to the protein;
(b9) a combination of a protein containing the amino acid sequence shown by SEQ ID NO:18 and ampicillin or a derivative thereof capable of binding to the protein.

[7] The method of [6] above, which comprises the following steps (a) to (c):
(a) a step for bringing a test substance and bioactive substance X into contact with target protein Y or a mutant protein thereof capable of binding to bioactive substance X;
(b) a step for measuring the binding level of bioactive substance X to the protein in the presence of the test substance, and comparing this binding level with the binding level of bioactive substance X to the protein in the absence of the test substance;
(c) a step for selecting a test substance that alters the binding level of bioactive substance X to the protein on the basis of the results of the comparison in step (b) above.

[8] A substance obtained by the method of any of [1] to [7] above.

[9] A regulator of bioactivity comprising a substance obtained by the method of any of [1] to [7] above.

[10] A binder to a target protein for a bioactive substance, which comprises a substance obtained by the method of any of [1] and [4] to [7] above.

[11] An agent of regulating an action associated with bioactive substance X, which comprises a substance that regulates the expression or function of target protein Y or a gene that encodes the protein, wherein the combination of the bioactive substance X and the target protein Y is any of the following (a1) to (a8):
(a1) a combination of cefaclor and a protein containing the amino acid sequence shown by SEQ ID NO:2, SEQ ID NO:6, SEQ ID NO:8 or SEQ ID NO:12;
(a2) a combination of ubenimex and a protein containing the amino acid sequence shown by SEQ ID NO:2;
(a3) a combination of aclarubicin and a protein containing the amino acid sequence shown by SEQ ID NO:4;
(a4) a combination of cefadroxil and a protein containing the amino acid sequence shown by SEQ ID NO:6;
(a5) a combination of ursolic acid and a protein containing the amino acid sequence shown by SEQ ID NO:10;
(a6) a combination of dicloxacillin and a protein containing the amino acid sequence shown by SEQ ID NO:14;
(a7) a combination of ketanserin and a protein containing the amino acid sequence shown by SEQ ID NO:16;
(a8) a combination of ampicillin and a protein containing the amino acid sequence shown by SEQ ID NO:18.

[12] The agent of [11] above, wherein the substance that regulates the expression or function of target protein Y or a gene that encodes the protein is a substance that suppresses the expression or function of the gene.

[13] The agent of [12] above, wherein the substance that suppresses the expression or function of target protein Y or a gene that encodes the target protein is the following (i) or (ii):
(i) a nucleic acid selected from the group consisting of an antisense nucleic acid, ribozyme, decoy nucleic acid, siRNA, a nucleic acid that encodes an antibody, and a nucleic acid that encodes a dominant negative mutant, or an expression vector comprising the nucleic acid;
(ii) a protein selected from the group consisting of an antibody and a dominant negative mutant.

[14] The regulating agent of [11] above, which comprises target protein Y or an expression vector comprising a nucleic acid that encodes the protein.

[15] An agent of regulating a function associated with target protein Y, which comprises bioactive substance X, wherein the combination of the target protein Y and the bioactive substance X is any of the following (b1) to (b9):
(b1) a combination of a protein containing the amino acid sequence shown by SEQ ID NO:2 and cefaclor, ubenimex or a derivative thereof capable of binding to the protein;
(b2) a combination of a protein containing the amino acid sequence shown by SEQ ID NO:4 and aclarubicin or a derivative thereof capable of binding to the protein;
(b3) a combination of a protein containing the amino acid sequence shown by SEQ ID NO:6 and cefaclor, cefadroxil or a derivative thereof capable of binding to the protein;
(b4) a combination of a protein containing the amino acid sequence shown by SEQ ID NO:8 and cefaclor or a derivative thereof capable of binding to the protein;
(b5) a combination of a protein containing the amino acid sequence shown by SEQ ID NO:10 and ursolic acid or a derivative thereof capable of binding to the protein;
(b6) a combination of a protein containing the amino acid sequence shown by SEQ ID NO:12 and cefaclor or a derivative thereof capable of binding to the protein;
(b7) a combination of a protein containing the amino acid sequence shown by SEQ ID NO:14 and dicloxacillin or a derivative thereof capable of binding to the protein;

(b8) a combination of a protein containing the amino acid sequence shown by SEQ ID NO:16 and ketanserin or a derivative thereof capable of binding to the protein;
(b9) a combination of a protein containing the amino acid sequence shown by SEQ ID NO:18 and ampicillin or a derivative thereof capable of binding to the protein.
[16] The agent of any of [11] to [15] above, which is a binder to target protein Y.
[17] A method of producing a derivative of bioactive substance X, which comprises the derivatizing bioactive substance X so as to be able to regulate the expression or function of target protein Y or a gene that encodes the protein, wherein the combination of the bioactive substance X and the target protein Y is any of the following (a1) to (a8):
(a1) a combination of cefaclor and a protein containing the amino acid sequence shown by SEQ ID NO:2, SEQ ID NO:6, SEQ ID NO:8 or SEQ ID NO:12;
(a2) a combination of ubenimex and a protein containing the amino acid sequence shown by SEQ ID NO:2;
(a3) a combination of aclarubicin and a protein containing the amino acid sequence shown by SEQ ID NO:4;
(a4) a combination of cefadroxil and a protein containing the amino acid sequence shown by SEQ ID NO:6;
(a5) a combination of ursolic acid and a protein containing the amino acid sequence shown by SEQ ID NO:10;
(a6) a combination of dicloxacillin and a protein containing the amino acid sequence shown by SEQ ID NO:14;
(a7) a combination of ketanserin and a protein containing the amino acid sequence shown by SEQ ID NO:16;
(a8) a combination of ampicillin and a protein containing the amino acid sequence shown by SEQ ID NO:18.
[18] A production method for a derivative of a substance capable of regulating a function associated with target protein Y, which comprises derivatizing bioactive substance X so that the bindability thereof to target protein Y or a mutant protein thereof capable of binding to bioactive substance X can be regulated,
wherein the combination of target protein Y and bioactive substance X is any of the following combinations (b1) to (b9):
(b1) a combination of a protein containing the amino acid sequence shown by SEQ ID NO:2 and cefaclor, ubenimex or a derivative thereof capable of binding to the protein;
(b2) a combination of a protein containing the amino acid sequence shown by SEQ ID NO:4 and aclarubicin or a derivative thereof capable of binding to the protein;
(b3) a combination of a protein containing the amino acid sequence shown by SEQ ID NO:6 and cefaclor, cefadroxil or a derivative thereof capable of binding to the protein;
(b4) a combination of a protein containing the amino acid sequence shown by SEQ ID NO:8 and cefaclor or a derivative thereof capable of binding to the protein;
(b5) a combination of a protein containing the amino acid sequence shown by SEQ ID NO:10 and ursolic acid or a derivative thereof capable of binding to the protein;
(b6) a combination of a protein containing the amino acid sequence shown by SEQ ID NO:12 and cefaclor or a derivative thereof capable of binding to the protein;
(b7) a combination of a protein containing the amino acid sequence shown by SEQ ID NO:14 and dicloxacillin or a derivative thereof capable of binding to the protein;
(b8) a combination of a protein containing the amino acid sequence shown by SEQ ID NO:16 and ketanserin or a derivative thereof capable of binding to the protein;
(b9) a combination of a protein containing the amino acid sequence shown by SEQ ID NO:18 and ampicillin or a derivative thereof capable of binding to the protein.
[19] A derivative of a bioactive substance obtained by the method of [17] or [18] above.

[20] A regulator of bioactivity comprising a derivative of a bioactive substance obtained by the method of [17] or [18] above.
[21] A binder to a target protein for a bioactive substance, which comprises a derivative of a bioactive substance obtained by the method of [17] or [18] above.
[22] A complex comprising bioactive substance X and target protein Y thereof, wherein the combination of the bioactive substance X and the target protein Y is any of the following (a1) to (a8) or (b1) to (b9):
(a1) a combination of cefaclor and a protein containing the amino acid sequence shown by SEQ ID NO:2, SEQ ID NO:6, SEQ ID NO:8 or SEQ ID NO:12;
(a2) a combination of ubenimex and a protein containing the amino acid sequence shown by SEQ ID NO:2;
(a3) a combination of aclarubicin and a protein containing the amino acid sequence shown by SEQ ID NO:4;
(a4) a combination of cefadroxil and a protein containing the amino acid sequence shown by SEQ ID NO:6;
(a5) a combination of ursolic acid and a protein containing the amino acid sequence shown by SEQ ID NO:10;
(a6) a combination of dicloxacillin and a protein containing the amino acid sequence shown by SEQ ID NO:14;
(a7) a combination of ketanserin and a protein containing the amino acid sequence shown by SEQ ID NO:16;
(a8) a combination of ampicillin and a protein containing the amino acid sequence shown by SEQ ID NO:18;
(b1) a combination of a protein containing the amino acid sequence shown by SEQ ID NO:2 and cefaclor, ubenimex or a derivative thereof capable of binding to the protein;
(b2) a combination of a protein containing the amino acid sequence shown by SEQ ID NO:4 and aclarubicin or a derivative thereof capable of binding to the protein;
(b3) a combination of a protein containing the amino acid sequence shown by SEQ ID NO:6 and cefaclor, cefadroxil or a derivative thereof capable of binding to the protein;
(b4) a combination of a protein containing the amino acid sequence shown by SEQ ID NO:8 and cefaclor or a derivative thereof capable of binding to the protein;
(b5) a combination of a protein containing the amino acid sequence shown by SEQ ID NO:10 and ursolic acid or a derivative thereof capable of binding to the protein;
(b6) a combination of a protein containing the amino acid sequence shown by SEQ ID NO:12 and cefaclor or a derivative thereof capable of binding to the protein;
(b7) a combination of a protein containing the amino acid sequence shown by SEQ ID NO:14 and dicloxacillin or a derivative thereof capable of binding to the protein;
(b8) a combination of a protein containing the amino acid sequence shown by SEQ ID NO:16 and ketanserin or a derivative hereof capable of binding to the protein;
(b9) a combination of a protein containing the amino acid sequence shown by SEQ ID NO:18 and ampicillin or a derivative thereof capable of binding to the protein.
[23] A production method for the complex of [22] above, which comprises bringing the bioactive substance and the target protein therefor into contact with each other.
[24] A kit comprising the following (i) and (ii):
(i) bioactive substance X or a salt thereof;
(ii) target protein Y, a nucleic acid that encodes the protein, an expression vector comprising the nucleic acid, cells that enable a measurement of the expression of the target protein Y, or an expression vector comprising the transcription regulatory region of a gene that encodes the target protein Y and a reporter gene functionally linked thereto, wherein the combination of the bioactive substance X and the target protein Y is any of (a1) to (a8) or (b1) to (b9) described in [22] above.

BEST MODE FOR CARRYING OUT THE INVENTION

1. Target Proteins and Target Genes for Bioactive Substances

The present invention provides target proteins and target genes for the development of bioactive substances.

A bioactive substance means any substance that has an action on the body. The bioactive substance can be an exogenous substance such as a drug, vitamin, herbal medicine ingredient, or food ingredient, and can be an endogenous substance such as a cytokine, growth factor, or hormone. When a given bioactive substance is intended, it is expressed as bioactive substance X as required.

Bioactive substance X includes the bioactive substances capable of regulating the expression or function of target gene Y described below, for example, bioactive substances capable of binding to target protein Y. Specifically, bioactive substance X can be cefaclor, ubenimex, aclarubicin, cefadroxil, ursolic acid, dicloxacillin, ketanserin or ampicillin, or a derivative thereof capable of binding to target protein Y (described later), or a salt thereof.

Bioactive substances can also be roughly divided, from the viewpoint of the type of activity that can be regulated thereby, into substances capable of regulating an action associated with bioactive substance X, and substances capable of regulating a function associated with target gene Y.

The target proteins and target genes for the development of bioactive substances can preferably be target proteins and target genes for drug discovery. When a given target protein and a given target gene are intended, they are expressed as target protein Y and target gene Y, respectively, as required. The term protein has the same definition as a translation product, and the term target gene Y has the same definition as a gene corresponding to target protein Y; these terms are interchangeably used.

For example, target protein Y can be a target protein for the above-described bioactive substance X. Specifically, target protein Y can be a protein containing the amino acid sequence shown by SEQ ID NO:2, SEQ ID NO:4, SEQ ID NO:6, SEQ ID NO:8, SEQ ID NO:10, SEQ ID NO:12, SEQ ID NO:14, SEQ ID NO:16 or SEQ ID NO:18. As mentioned herein, the target proteins of the present invention are not limited to human proteins mentioned above, but include orthologues of different animal species. Referring to human proteins for reference of each protein, FLJ No. (registration No. in NEDO (New Energy and Industrial Technology Development Organization) protein cDNA structure analysis project), GenBank accession No., H-Inv cDNA ID and H-Inv locus ID in H-Invitational database (H-Inv DB), and some examples of binding bioactive substances discovered by the present inventors are shown in Table 1, respectively.

According to the present invention, a mutant protein of the above-mentioned protein having a binding ability to bioactive substance X is provided. The mutant protein can also be, for example, a protein that contains an amino acid sequence resulting from the substitution, deletion, addition or insertion of one or more amino acids in the amino acid sequence shown by SEQ ID NO: 2, SEQ ID NO:4, SEQ ID NO:6, SEQ ID NO:8, SEQ ID NO:10, SEQ ID NO:12, SEQ ID NO:14, SEQ ID NO:16 or SEQ ID NO:18, and that interacts with a bioactive substance.

The number of amino acids substituted, deleted, added or inserted can be any one that allows the retention of the function, for example, about 1 to 30, preferably about 1 to 20, more preferably about 1 to 10, further more preferably about 1 to 5, most preferably 1 or 2. The site for substitution, deletion, addition or insertion of an amino acid can be any site that allows the retention of the function, for example, a site other than functionally important domains.

Furthermore, the mutant protein provided by the present invention can be a protein which consists of, for example, an amino acid sequence having a homology of about 50% or more, preferably about 70% or more, more preferably about 80% or more, further more preferably about 90% or more, most preferably about 95% or more (but excluding 100% homology), to the amino acid sequence shown by SEQ ID NO:2, SEQ ID NO:4, SEQ ID NO:6, SEQ ID NO:8, SEQ ID NO:10, SEQ ID NO:12, SEQ ID NO:14, SEQ ID NO:16 or SEQ ID NO:18, and which interacts with a bioactive substance. Here, the numerical values of the above-described homology are calculated by, for example, executing the commands for the maximum matching method using the DNASIS sequence analytical software (Hitachi Software Engineering). The parameters for the calculation should be used in default settings (initial settings).

When a target protein of the present invention is used, the protein may be a labeled supply or a non-labeled supply, or a mixture of a labeled supply and a non-labeled supply mixed in a specified ratio. Examples of the labeling substance include fluorescent substances such as FITC and FAM, luminescent substances such as luminol, luciferin and lucigenin, radioisotopes such as $^3H$, $^{14}C$, $^{32}P$, $^{35}S$, and $^{123}I$, affinity substances such as biotin and streptavidin, and the like.

The target genes of the present invention may be any ones that encode the target proteins of the present invention. For example, the target genes of the present invention can be those corresponding to proteins has the above-described amino acid sequences. Preferably, the target genes of the present invention consist of the nucleotide sequences shown by SEQ ID NO:1, SEQ ID NO:3, SEQ ID NO:5, SEQ ID NO:7, SEQ

TABLE 1

| FLJ NO. | SEQ ID NO | GenBank Accession No. | H-InV cDNA ID | H-Inv locus ID | Example of bioactive substance to be bound with |
|---|---|---|---|---|---|
| FLJ10335 | 2 | AK001197 | HIT000003671 | HIX0002071 | cefaclor ubenimex |
| FLJ10889 | 4 | AK001751 | HIT000004225 | HIX0009296 | aclarubicin |
| FLJ11045 | 6 | AK001907 | HIT000004381 | HIX0011179 | cefaclor cefadroxil |
| FLJ11474 | 8 | AK021536 | HIT000004810 | HIX0012725 | cefaclor |
| FLJ12502 | 10 | AK022564 | HIT000005838 | HIX0011889 | ursolic acid |
| FLJ14467 | 12 | AK027373 | HIT000010645 | HIX0014016 | cefaclor |
| FLJ14583 | 14 | AK027489 | HIT000010761 | HIX0016824 | dicloxacillin |
| FLJ14797 | 16 | AK027703 | HIT000010975 | HIX0012185 | ketanserin |
| FLJ31146 | 18 | AK055708 | HIT000012322 | HIX0006596 | ampicillin |

ID NO:9, SEQ ID NO:11, SEQ ID NO:13, SEQ ID NO:15 or SEQ ID NO:17. In the present specification, the target genes of the present invention are not limited to human genes mentioned above, but include orthologues of different animal species.

According to the present invention, a gene that consists of a nucleotide sequence that hybridizes to a sequence complementary to the nucleotide sequence shown by SEQ ID NO:1, SEQ ID NO:3, SEQ ID NO:5, SEQ ID NO:7, SEQ ID NO:9, SEQ ID NO:11, SEQ ID NO:13, SEQ ID NO:15 or SEQ ID NO:17 under stringent conditions, and that corresponds to a protein that interacts with a bioactive substance is also provided. Here, "hybridize under stringent conditions" means that a positive hybridization signal remains observable even under conditions of, for example, heating in a solution of 6×SSC, 0.5% SDS and 50% formamide at 42° C., followed by washing in a solution of 0.1×SSC and 0.5% SDS at 68° C.

The target proteins and target genes of the present invention can be used for the development of drugs for diseases or conditions associated with bioactive substance X, or diseases or conditions associated with target gene Y, or for the development of investigational reagents for the diseases or conditions, and the like. Diseases or conditions associated with bioactive substance X and diseases or conditions associated with target gene Y are described in detail below.

(Diseases or Conditions Associated with Bioactive Substance X)

"A disease or condition associated with bioactive substance X" means a disease for which bioactive substance X is used or a disease corresponding to an adverse effect of bioactive substance X, or a condition for which use of bioactive substance X is desired (e.g., a deficiency of bioactive substance X) or an unwanted condition caused by bioactive substance X (e.g., an unwanted condition caused by excess intake of bioactive substance X). A disease or condition associated with bioactive substance X can be ameliorated or exacerbated by bioactive substance X.

"An action associated with bioactive substance X" means an action of the same kind as, or opposite kind to, a kind of action actually exhibited by bioactive substance X (including pharmacological actions and adverse effects). Hence, an action associated with bioactive substance X is an action capable of ameliorate or exacerbate "a disease or condition associated with bioactive substance X". For example, "an action associated with bioactive substance X" is an antiinflammatory action/inflammatory action and the like when bioactive substance X is ursolic acid, and is hypotensive action/hypertensive action and the like when it is ketanserin.

"A disease or condition associated with bioactive substance X" and "an action associated with bioactive substance X" vary depending on the kind of bioactive substance X. Described below are "diseases or conditions associated with bioactive substance X" with reference to substances that represent bioactive substance X. Because "an action associated with bioactive substance X" is any action capable of ameliorating or exacerbating "a disease or condition associated with bioactive substance X", the following description of "diseases or conditions associated with bioactive substance X" will surely lead to the clarification of "actions associated with bioactive substance X".

Cefaclor

A disease associated with cefaclor means a disease for which cefaclor is used or a disease corresponding to an adverse drug reaction of cefaclor. Cefaclor is known as a first-generation cefem-series antibiotic and the like. In addition, cefaclor may have a neuroprotective action. Examples of the disease for which cefaclor is used include infectious diseases (laryngopharyngitis, tonsillitis, bronchitis, cellulitis, infectious atheroma, subcutaneous abscess, felon, lymphadenitis, tympanitis) caused by cefaclor-sensitive strains of bacteria of the genus *Staphylococcus*, bacteria of the genus *Streptococcus* (excluding enterococci), *Haemophilus influenzae*, *Escherichia coli*, and bacteria of the genus *Klebsiella*, as well as neurodegenerative disease, amyotrophic lateral sclerosis (ALS), and the like. Examples of the adverse drug reaction of cefaclor include shock, anaphylactoid symptoms, acute renal insufficiency, pancytopenia, agranulocytosis, thrombocytopenia, pseudomembranous colitis, mucocutaneous eye syndrome (Stevens-Johnson syndrome), toxic epidermal necrolysis (Lyell syndrome), interstitial pneumonia, PIE syndrome, liver dysfunction, jaundice and the like. An action associated with cefaclor can be closely relevant to a target protein (target gene) therefor, for example, a protein consisting of the amino acid sequence shown by SEQ ID NO:2, SEQ ID NO:6, SEQ ID NO:8 or SEQ ID NO:12.

Ubenimex

A disease associated with ubenimex means a disease for which ubenimex is used or a disease corresponding to an adverse drug reaction of ubenimex. Ubenimex is known as an anti-malignant tumor agent and the like. Examples of the disease for which ubenimex is used include extension of survival by combination therapy with chemotherapeutic agents for maintenance enhancement after induction of complete remission for adult acute non-lymphatic leukemia and the like. Examples of the adverse drug reaction of ubenimex include hepatopathies (elevation of AST (GOT)/ALT (GPT) and the like), dermatopathies (eruption/reddening, sensation of itching and the like), gastrointestinal disorders (nausea/vomiting, anorexia and the like) and the like. An action associated with ubenimex can be closely relevant to a target protein (target gene) therefor, for example, a protein consisting of the amino acid sequence shown by SEQ ID NO:2.

Aclarubicin

A disease associated with aclarubicin means a disease for which aclarubicin is used or a disease corresponding to an adverse drug reaction of aclarubicin. Aclarubicin is known as an antitumor antibiotic and the like. Examples of the disease for which aclarubicin is used include remission and amelioration of subjective and objective symptoms of gastric cancer, lung cancer, breast cancer, ovarian cancer, malignant lymphoma, and acute leukemia. Examples of the adverse drug reaction of aclarubicin include cardiomyopathy, bone marrow suppression and the like. An action associated with aclarubicin can be closely relevant to a target protein (target gene) therefor, for example, a protein consisting of the amino acid sequence shown by SEQ ID NO:4. As a target for aclarubicin, DNA topoisomerase II is known.

Cefadroxil

A disease associated with cefadroxil means a disease for which cefadroxil is used or a disease corresponding to an adverse drug reaction of a disease corresponding to an adverse drug reaction of cefadroxil. Cefadroxil is known as a first-generation cefem-series antibiotic and the like. In addition, cefadroxil may have a neuroprotective action. Examples of the disease for which cefadroxil is used include infectious diseases (laryngopharyngitis, tonsillitis, bronchitis, cystitis, pyelonephritis, folliculitis (including acne pustulosa), furuncle, furunculosis, carbuncle, subcutaneous abscess, cellulitis, acne conglobata, hidradenitis, infectious atheroma) caused by cefadroxil-sensitive strains of bacteria of the genus *Staphylococcus*, hemolytic streptococci, pneumococci, *Escherichia coli*, and *Proteus mirabilis*, as well as neurodegenerative disease, amyotrophic lateral sclerosis (ALS), and the like. Examples of the adverse drug reaction of cefadroxil include shock, pseudomembranous colitis, and ucocutaneous eye syndrome (Stevens-Johnson syndrome). An action associated with cefadroxil can be closely relevant to a target protein (target gene) therefor, for example, a protein consisting of the amino acid sequence shown by SEQ ID NO:6.

Ursolic Acid

A condition associated with ursolic acid means a condition for which use of ursolic acid is desired or an unwanted condition caused by ursolic acid. Ursolic acid is contained in extracts from rosemary, a kind of herbal plant, and the like. Ursolic acid generally exhibits anti-inflammatory action and blood circulation promoting action, and is known to be effective in preventing and ameliorating stress-induced chapped skin and barrier functional reduction, and promoting skin regeneration, and the like. Hence, an action associated with ursolic acid may be exemplified by these actions or actions opposite thereto. An action associated with ursolic acid can be closely relevant to a target protein (target gene) therefor, for example, a protein consisting of the amino acid sequence shown by SEQ ID NO:10.

Dicloxacillin

A disease associated with dicloxacillin means a disease for which dicloxacillin is used or a disease corresponding to an adverse drug reaction of dicloxacillin. Dicloxacillin is known as a penicillin-series antibiotic and the like. In addition, dicloxacillin may have a neuroprotective action. Examples of the disease for which dicloxacillin is used include bacterial pneumonia, bronchial pneumonia, infections with bronchiectasis/chronic bronchitis/pulmonary emphysema and bronchial asthma, lung suppuration, pyothorax, secondary infection of pulmonary tuberculosis, complex urinary tract infection, as well as neurodegenerative disease, amyotrophic lateral sclerosis (ALS), and the like. Examples of the adverse drug reaction of dicloxacillin include shock, mucocutaneous eye syndrome (Stevens-Johnson syndrome), toxic epidermal necrolysis (Lyell syndrome), agranulocytosis, hemolytic anemia, serious nephropathies such as acute renal insufficiency, and serious forms of colitis with hematochezia, such as pseudomembranous colitis. An action associated with dicloxacillin can be closely relevant to a target protein (target gene) therefor, for example, a protein consisting of the amino acid sequence shown by SEQ ID NO:14.

Ketanserin

A disease associated with ketanserin means a disease for which ketanserin is used or a disease corresponding to an adverse drug reaction of ketanserin. Ketanserin is known as a 5-HT2A receptor antagonist, antihypertensive drug and the like. Examples of the disease for which ketanserin is used include hypertension. Examples of the adverse drug reaction of ketanserin include QT prolongation. An action associated with ketanserin can be closely relevant to a target protein (target gene) therefor, for example, a protein consisting of the amino acid sequence shown by SEQ ID NO:16. As a target for ketanserin, 5-hydroxytryptamine 2C receptor is known.

Ampicillin

A disease associated with ampicillin means a disease for which ampicillin is used or a disease corresponding to an adverse drug reaction of ampicillin. Ampicillin is known as a penicillin-series antibiotic and the like. In addition, ampicillin may have a neuroprotective action. Examples of the disease for which ampicillin is used include sepsis, bacterial endocarditis, furuncle, carbuncle, impetigo, pyoderma, phlegmon, mastitis, lymphadenitis, osteomyelitis, tonsillitis, pharyngitis, laryngitis, bronchitis, pneumonia, lung suppuration, pyothorax, peritonitis, acute pancreatitis, liver abscess, cholangitis, cholecystitis, bacterial dysentery, pyelonephritis, cystitis, urethritis, intrauterine infection, gonorrhea, syphilis, scarlatina, palpebral abscess, sties, serpiginous corneal ulcers, tympanitis, sinusitis, acute marginal supprative periodontitis, acute apical supprative periodontitis, inflammation around wisdom teeth, gingival abscess, alveolitis, acute inflammation of the jaw, infections after tooth removal, secondary infections after wounds/burns and surgery, prevention of secondary infection of severe burns, actinomycosis, anthrax, as well as neurodegenerative disease, amyotrophic lateral sclerosis (ALS), and the like. Examples of the adverse drug reaction of ampicillin include shock, mucocutaneous eye syndrome (Stevens-Johnson syndrome), toxic epidermal necrolysis (Lyell syndrome), agranulocytosis, hemolytic anemia, serious nephropathies such as acute renal insufficiency, serious forms of colitis with hematochezia such as pseudomembranous colitis and the like. An action associated with ampicillin can be closely relevant to a target protein (target gene) therefor, for example, a protein consisting of the amino acid sequence shown by SEQ ID NO:18.

(Diseases or Conditions Associated with Target Gene Y)

"A disease or condition associated with target gene Y (or target protein Y)" refers to a disease or condition that can be caused as a result of a functional change (e.g., functional changes due to mutations (e.g., polymorphism)), or a change in the expression level, in target gene Y (or target protein Y), or in a gene located downstream of target gene Y in the signal transduction system mediated by target gene Y (downstream gene). A functional change in target gene Y or a gene downstream thereof can be caused by, for example, a mutation (e.g., polymorphism) in the gene. Examples of the mutation include a mutation in the coding region, which promotes or suppresses a function of the gene, a mutation in the non-coding region, which promotes or suppresses the expression thereof, and the like. The change in the expression level include increases or reductions in the expression level. A disease or condition associated with target gene Y can be ameliorated or exacerbated by target protein Y.

"A function associated with target gene Y" means a function of the same kind as, or opposite kind to, the kind of function that is actually exhibited by target protein Y. In other words, a function associated with target gene Y is a function capable of ameliorating or exacerbating "a disease or condition associated with target gene Y". Hence, "a function associated with target gene Y" is a function for promoting or suppressing an immune reaction, and the like, when target gene Y encodes a factor that promotes an immune reaction and the like.

Since target gene Y is considered to mediate a wide variety of physiological functions in the body; as diseases or conditions associated with target gene Y, a very wide variety of diseases or conditions are supposed. One example of possible diseases or conditions is a disease or condition postulated from the annotation of target gene Y. Those skilled in the art can postulate such diseases or conditions by identifying homologous genes by homology search, and subsequently extensively examining the functions of the homologous gene or the diseases or conditions mediated thereby by a commonly known method. Various methods are available for annotation analysis. Described below are the results of annotation of target genes for bioactive substances in the present application, by various methods using the sequences of human genes representative of target genes for bioactive substances as query sequences.

Amino Acid Analysis 1

Homology Analysis by BLASTP

The calculation program used was blastall 2.2.6. The target databases used were swiss-prot: 146720 (Mar. 29, 2004), (Refseq)hs: 21170 (May 6, 2004), (Refseq)mouse: 17089

(May 6, 2004), and (Refseq)rat: 4893 (May 6, 2004). The cutoff value was established at 1.00E-05. The following data were processed by filtering:

For Swiss-prot:
  Having a definition beginning with "ALU SUBFAMILY"
  Having a definition beginning with "Alu subfamily"
  Having a definition beginning with "!!!! ALU SUBFAMILY"
  Having a definition beginning with "B-CELL GROWTH FACTOR PRECURSOR"
  Having a definition including "NRK2"
  Having a definition beginning with "PROLINE-RICH"
  Having a definition beginning with "GLYCINE-RICH"
  Having a definition beginning with "EXTENSIN PRECURSOR"
  Having a definition beginning with "COLLAGEN"
  Having a definition beginning with "100KD"
  Having a definition beginning with "RETROVIRUS-RELATED POL POLYPROTEIN"
  Having a definition beginning with "CUTICLE COLLAGEN"
  Having a definition beginning with "HYPOTHETICAL"
  Having a definition beginning with "Hypothetical"
  Having a definition beginning with "SALIVARY PROLINE-RICH PROTEIN"
  Having a definition beginning with "IMMEDIATE-EARLY PROTEIN"
  Having the accession number "P49646"

For Ref-seq:
  Having a definition beginning with "hypothetical protein FLJ"
  Having a definition beginning with "KIAA"
  Having a definition beginning with "hypothetical protein DKFZ"
  Having a definition beginning with "DKFZ"
  Having a definition beginning with "RIKEN cDNA"
  Having a definition beginning with "hypothetical protein MGC"
  Having a definition as "hypothetical protein"
  Having a definition beginning with "hypothetical protein PP"
  Having a definition as "neuronal thread protein"
  Having a definition beginning with "clone FLB"
  Having a definition beginning with "hypothetical protein PRO"
  Having a definition as "PRO0483 protein"
  Having a definition including "MNC"
  Having a definition including "MOST-1"
  Having a definition beginning with "similar to"
  Having a definition including "TPR gene on Y"
  Having a definition beginning with "HSPC"
  Having a definition beginning with "CGI-"
  ReFSeq sequence composed of self only (information referenced from LL_tmpl)

The annotation information obtained by this analysis is shown in Tables 2-1 to 2-2.

TABLE 2-1

| FLJ No. | Accession No. and definition | Key words |
|---|---|---|
| FLJ10335 | Q9NW38 ubiquitin ligase protein PHF9 (EC 6.3.2.—) (FAAP 43) Q9CR14 ubiquitin ligase protein PHF9 (EC 6.3.2.—) (Proliferation of germ cells) NP_060532.1 Fanconi anemia, complementation group L; PHD finger protein 9 [Homo sapiens] | DNA repair; Ubl conjugation pathway; ligase; nuclear protein; metal bond; zinc; |

TABLE 2-1-continued

| FLJ No. | Accession No. and definition | Key words |
|---|---|---|
|  | NP_080199.1 Fanconi anemia, complementation group L; Proliferation of germ cells; PHD finger protein 9; germ cell deficient [Mus musculus] | zinc finger; alternative splicing |
| FLJ10889 | O35286 putative pre-mRNA splicing factor RNA helicase (DEAH box protein 15) O43143 putative pre-mRNA splicing factor RNA helicase(DEAH box protein 15) (ATP-dependent RNA helicase #46) O22899 putative pre-mRNA splicing factor ATP-dependent RNA helicase NP_060650.2 DEAD/H (Asp-Glu-Ala-Asp/His) box polypeptide 32 [Homo sapiens] NP_598702.1 helicase DDX32; DEAD/H (Asp-Glu-Ala-Asp/His) box polypeptide 32 [Mus musculus] NP_291084.1 DEAQ RNA-dependent ATPase [Mus musculus] | mRNA processing; mRNA splicing; helicase; ATP-binding; nuclear protein |
| FLJ11045 | Q9NUY9 tudor domain-containing protein 4 Q9BXT4 tudor domain-containing protein 1 O88884 A kinase anchor protein 1, mitochondrial precursor (protein kinase A-anchoring protein 1) (PRKA1) (A-kinase anchor protein 121 kDa) (AKAP 121) (Dual specificity A-kinase-anchoring protein 1) (D-AKAP-1) (Spermatid A-kinase anchor protein 84) (S-AKAP84) NP_061911.2 tudor domain-containing 4 [Homo sapiens] NP_942090.1 tudor domain containing protein1 [Homo sapiens] NP_113564.1 tudor domain-containing protein1 [Mus musculus] | RNA-bindig; mitochondrion; alternative splicing; outer membrane; transmenbrane; transit peptide |
| FLJ11474 | Q00808 vegetatible incompatibility protein HET-E-1 P78706 transcription repressorrco-1 Q9V3J8 Will die slowly protein NP_064372.2 G protein beta subunit-like; transducin (beta)-like 4 [Mus musculus] NP_071799.1 G protein beta subunit-like; G beta-like protein [Rattus norvegicus] NP_071767.2 G protein beta subunit-like [Homo sapiens] | GTP-binding; repeat; WD repeat Conidiation; transcriptional control; repressor |
| FLJ12502 | NP_079228.3 chromosome 14 open reading frame 160 [Homo sapiens] |  |

TABLE 2-2

| FLJ14467 | Q9HB40 Retinoid-inducible serine carboxypeptidase precursor (EC 3.4.16.—) (serine carboxypeptidase 1) (MSTP034) Q920A6 Retinoid-inducible serine carboxypeptidase precursor (EC 3.4.16.—) Q920A5 Retinoid-inducible serine carboxypeptidase precursor (EC 3.4.16.—) NP_067639.1 serine carboxypeptidase 1 precursor protein; promising homologue of rat and mouse retinoid-inducible serine carboxypeptidases [Homo sapiens] NP_596874.1 Retinoid-inducible serine carboxypeptidase [Rattus norvegicus] NP_083299.2 serine carboxypeptidase 1; Retinoid-inducible serine carboxypeptidase; Retinoid-inducible serine carboxypeptidase [Mus musculus] | hydrolase; carboxy-peptidase; signal; glyocprotein; alternative splicing |
|---|---|---|
| FLJ14583 | Q12816 Trophinin (MAGE-D3 antigen) Q9UNF1 Melanoma-associated antigen D2 (MAGE-D2 antigen) (MAGE-D) (breast cancer- associated gene 1 protein) (BCG-1) (11B6) (Hepatocellular carcinoma-associated protein JCL-1) Q9QYH6 Melanoma-associated antigen D1 (MAGE-D1 antigen) (Neurotrophin receptor-interacting MAGE homolog) (Dlxin-1) NP_808224.1 Trophinin isoform 2; | cell adhesion; antigen; repeat antigen; Multigene family; polymorphism; alternative splicing |

TABLE 2-2-continued

| | | |
|---|---|---|
| | magphinin; MAGE superfamily protein [*Homo sapiens*] NP_057241.2 Trophinin isoform 2; magphinin; MAGE superfamily protein [*Homo sapiens*] NP_808223.1 Trophinin isoform 1; magphinin; MAGE superfamily protein [*Homo sapiens*] | |
| FLJ14797 | Q9UGJ1 Gamma-tubulin complex component 4 (GCP-4) (hGCP4) (h76p) (Hgrip76) Q9D4F8 Gamma-tubulin complex component 4 (GCP-4) Q9M350 Gamma-tubulin complex component 4 homologue NP_055259.2 gamma tubulin ring complex protein (76p gene) [*Homo sapiens*] NP_700436.1 gamma tubulin ring complex protein [*Mus musculus*] NP_598516.1 tubulin, gamma complex associated protein 2 [*Mus musculus*] | microtubule |
| FLJ31146 | Q9JJK5 Homocysteine-responsive endoplasmic reticulum-resident ubiquitin-like domain member 1 protein Q15011 Homocysteine-responsive endoplasmic reticulum-resident ubiquitin-like domain member 1 protein (Methyl methanesulfonate (MMF)-inducible fragment protein 1) NP_071726.1 homocysteine-inducible, endoplasmic reticulum stress-inducible, ubiquitin-like domain member 1 [*Mus musculus*] NP_445975.1 homocysteine-inducible, endoplasmic reticulum stress-inducible, ubiquitin-like domain member 1 [*Rattus norvegicus*] NP_055500.1 homocysteine-inducible, endoplasmic reticulum stress-inducible, ubiquitin-like domain member 1; MMS-inducible gene [*Homo sapiens*] | unfold protein response; endoplasmic reticulum; transmembrane, alternative splicing |

Amino Acid Analysis 2
Motif Analysis by Pfam

The calculation program used was hmmpfam (v2.3.2). The target databases used were Pfam DB entry: 7426 families (Pfam13.0, Pfam_1s). (April 2004). The cutoff value was established at 1E-10. The annotation information obtained by this analysis is shown by Table 3.

TABLE 3

| | PfamID and Pfam name | Pfam description |
|---|---|---|
| FLJ10335 | | |
| FLJ10889 | PF04408.6 HA2 | helicase-associated domain (HA2) |
| FLJ11045 | PF00567.10 TUDOR | tudor domain¥tudor domain |
| FLJ11474 | | |
| FLJ12502 | PF07286.1 DUF1445 | protein of unknown function (DUF1445) |
| FLJ14467 | PF00450.9 Peptidase_S10 | serine carboxypeptidase |
| FLJ14583 | PF01454.6 MAGE | MAGE family |
| FLJ14797 | PF04130.3 Spc97_Spc98 | Spc97/Spc98 family |
| FLJ31146 | | |

Amino Acid Analysis 3
Prediction of Secretory Signal Sequences by Signal IP

The calculation program used was SignalP ver 3.0 (May 18, 2004). From this analysis, it was postulated that the FLJ14467-derived protein had a secretory signal.

Amino Acid Analysis 4
Functional Categorization by GeneOntology

Performed per the procedures described below.

1) Extract results having E-values that meet the following conditions from among the results of homology analysis using BLASTP (RefSeq and SwissProt with filter) that produced three higher BLAST results (six in total).

Condition 1: Use all results having E-values of not more than 1E-50.

Condition 2: Do not use results having E-values of not less than 1E-10.

Condition 3: Use results having E-values exceeding 1E-50, provided that the difference in E-value from Top Hit is within 1E+20.

Condition 4: If the E-value of Top Hit is 0, use results having E-values of not more than 1E-50.

2) Search GO by the keywords of SwissProt using spkw2go.

3) Search xref.goa by accession numbers of SwissProt to acquire Refseq IDs, further acquire LOCUS IDs by the Refseq IDs using LL_tmpl, and acquire GO terms by the LOCUS IDs using loc2go.

4) Acquire LOCUS IDs by accession numbers of Refseq using LL_tmpl, and acquire GO terms by the LOCUS IDs using loc2go.

5) Acquire information on higher categories for each GO term acquired, with reference to the Molecular Function text file, Biological Process text file, and Cellular Component text file.

6) Remove overlapping information from the GO term information acquired in 1)-5) above, and make an output.

The annotation information obtained by this analysis is shown in Tables 4-1 and 4-2.

TABLE 4-1

| FLJ No. | GO classification | GO No. (term) |
|---|---|---|
| FLJ10335 | MF | GO: 0016874¥MF|ligase activity |
| | BP | GO: 0006281¥BP|DNA repair; GO: 0007276¥BP|gametogenesis; GO: 0042127¥BP|control of cell growth |
| | CC | GO: 0005634¥CC|nucelus |
| FLJ10889 | MF | GO: 0000166¥MF|nucleotide bond; GO: 0003676¥MF|nucleic acid-binding; GO: 0003724¥MF|RNA helicase activity; GO: 0004386¥MF|helicase activity; GO: 0005488¥MF|bond; GO: 0005509¥MF|calcium ion-binding; GO: 0005524¥MF|ATP-binding; GO: 0008026¥MF|ATP-dependent helicase activity; GO: 0016887¥MF|ATPase activity |
| | BP | GO: 0000398¥BP|spliceosome-mediated nuclear mRNA splicing; GO: 0006397¥BP|mRNA processing; GO: 0006810¥BP|transport |
| | CC | GO: 0005622¥CC|intracellular; GO: 0005634¥CC|nucelus; GO: 0005743¥CC|mitochondrial inner membrane |
| FLJ11045 | MF | GO: 0003676¥MF|nucleic acid-binding |
| | BP | |
| | CC | |
| FLJ11474 | MF | GO: 0005554¥MF|molecular function unknown |
| | BP | GO: 0000004¥BP|biological process unknown |
| | CC | GO: 0008372¥CC|cellular component unknown |

TABLE 4-2

| FLJ12502 | MF | |
|---|---|---|
| | BP | |
| | CC | |
| FLJ14467 | MF | GO: 0003824¥MF|catalytic activity; GO: 0004177¥MF|aminopeptidase activity; GO: 0004180¥MF|carboxypeptidase activity; GO: 0004185¥MF|serine carboxypeptidase activity; GO: 0016787¥MF|hydrolase activity |
| | BP | GO: 0006508¥BP|protein degradation peptide degradation |
| | CC | GO: 0005615¥CC|extracellular space |

TABLE 4-2-continued

| FLJ14583 | MF | GO: 0005515¥MF\|protein-binding |
| --- | --- | --- |
| | BP | GO: 0007155¥BP\|cell adhesion; |
| | | GO: 0007156¥BP\|homophilic cell adhesion; |
| | | GO: 0007566¥BP\|embryo implantation |
| | CC | GO: 0005887¥CC\|component of plasma membrane |
| FLJ14797 | MF | GO: 0005200¥MF\|structural component of cytoskeleton |
| | BP | GO: 0006461¥BP\|protein complex assembly; |
| | | GO: 0007020¥BP\|nuclear aggregation of microtubule (nucleation) |
| | CC | GO: 0005813¥CC\|centrosome; GO: 0008274¥CC\|gamma-tubulin ring complex; |
| | | GO: 0015630¥CC\|microtubular cytoskeleton |
| FLJ31146 | MF | GO: 0005554¥MF\|molecule function unknown |
| | BP | GO: 0006950¥BP\|stress-responsive; |
| | | GO: 0006986¥BP\|unfold protein-responsive |
| | CC | GO: 0005783¥CC\|endoplasmic reticulum; |
| | | GO: 0005789¥CC\|endoplasmic reticulum membrane; |
| | | GO: 0016021¥CC\|membrane component |

Nucleic Acid Analysis 1

Homology Analysis 1 by BLASTX

The calculation program used was blastall 2.2.6. The target database used was nr:1552011 (Jul. 16, 2004). The cutoff value was established at 1.00E-05. The following data were processed by filtering:

Having a definition beginning with "ALU SUBFAMILY"

Having a definition including "Alu subfamily"

Having a definition beginning with "!!!! ALU SUBFAMILY"

Beginning with "*Drosophila melanogaster* genomic scaffold"

Beginning with "Human DNA sequence from"

Including "genomic DNA"

Including "BAC clone"

Including "PAC clone"

Including "cosmid"

Including "complete genome"

Ending with "complete sequence"

Including "genomic sequence"

Including "exon"

A "HIT LENGTH (sequence length of the hit sequence) of not less than 50000 obtained by this analysis The annotation information obtained by this analysis is shown in Tables 5-1 to 5-3.

TABLE 5-1

| FLJ No. | nraccession No. and definition |
| --- | --- |
| FLJ10335 | ref\|NP_060532.1\| Fanconi anemia, complementation group L; PHD finger protein 9 [*Homo sapiens*]¥ sp\|Q9NW38\|PHF9_human ubiquitin ligase protein PHF9 (FAAP 43)¥ dbj\|BAA91548.1\| unnamed protein product [*Homo sapiens*] gb\|AAH54517.1\| Fanconi anemia, complementation group L [*Homo sapiens*] ref\|NP_080199.1\| Fanconi anemia, complementation group L; Proliferation of germ cells; PHD finger protein 9; germ cell deficient [*Mus musculus*]¥ dbj\|BAB25772.1\| unnamed protein product [*Mus musculus*]¥ dbj\|BAB27674.1\| unnamed protein product [*Mus musculus*]¥ dbj\|BAB27820.1\| unnamed protein product [*Mus musculus*]¥ dbj\|BAB31039.1\| unnamed protein product [*Mus musculus*]¥ gb\|AAN64921.1\| proliferation of germ cells protein [*Mus musculus*]¥ dbj\|BAC36123.1\| unnamed protein product [*Mus musculus*] ref\|XP_223701.2\| similar to PHD finger protein 9; proliferation of germ cells; germ cell deficient [*Rattus norvegicus*] dbj\|BAB27906.1\| unnamed protein product [*Mus musculus*] |

TABLE 5-1-continued

| FLJ No. | nraccession No. and definition |
| --- | --- |
| FLJ10889 | gb\|AAH02473.2\| DEAD/H (Asp-Glu-Ala-Asp/His) box protein 32 [human] dbj\|BAA91882.1\| unnamed protein product [*Homo sapiens*] ref\|NP_060650.2\| DEAD/H (Asp-Glu-Ala-Asp/His) box protein 32 [*Homo sapiens*]¥ gb\|AAL26550.1\| putative DEAD/DEXH helicase DDX32 [*Homo sapiens*]¥ gb\|AAL55437.1\| DEAD/H helicase-like protein-1 [*Homo sapiens*]¥ gb\|AAL55441.1\| DEAD/H helicase-like protein-1 [*Homo sapiens*] dbj\|BAA91754.1\| unnamed protein product [*Homo sapiens*] ref\|NP_598702.1\| helicase DDX32 [*Mus musculus*]¥ gb\|AAL47579.1\| helicase DDX32 [*Mus musculus*]¥ gb\|AAH22920.1\| helicase DDX32 [*Mus musculus*] |

TABLE 5-2

| FLJ11045 | ref\|NP_061911.1\| tudor domain-containing 4 [*Homo sapiens*]¥ sp\|Q9NUY9\|TDR4_human tudor domain-containing protein 4¥ dbj\|BAA91972.1\| unnamed protein product [*Homo sapiens*] dbj\|BAB64438.1\| hypothetical protein [*Macaca fascicularis*] ref\|XP_224231.2\| similar to hypothetical protein [*Rattus norvegicus*] ref\|XP_354818.1\| similar to tudor domain-containing protein 4 [*Mus musculus*] dbj\|BAC26567.1\| unnamed protein product [*Mus musculus*] |
| --- | --- |
| FLJ11474 | gb\|AAH01313.1\| GBL protein [*Homo sapiens*]¥ gb\|AAH17119.1\| GBL protein [*Homo sapiens*]¥ gb\|AAH52292.1\| GBL protein [*Homo sapiens*] ref\|NP_064372.2\| G protein beta subunit-like; transducin (beta)-like 4 [*Mus musculus*]¥ dbj\|BAB22328.1\| unnamed protein product [*Mus musculus*]¥ gb\|AAH15279.1\| G protein beta subunit-like [*Mus musculus*]¥ dbj\|BAC30024.1\| unnamed protein product [*Mus musculus*]¥ dbj\|BAC30510.1\| unnamed protein product [*Mus musculus*]¥ dbj\|BAC36952.1\| unnamed protein product [*Mus musculus*] ref\|XP_346397.1\| G protein beta subunit-like [*Rattus norvegicus*]¥ gb\|AAF37719.1\|G beta-like protein GBL [*Mus musculus*] dbj\|BAC33243.1\| unnamed protein product [*Mus musculus*] dbj\|BAC39006.1\| unnamed protein product [*Mus musculus*] |
| FLJ12502 | ref\|NP_079228.2\| hypothetical protein FLJ20950 [*Homo sapiens*]¥ dbj\|BAB14102.1\| unnamed protein product [*Homo sapiens*]¥ gb\|AAH10614.1\| chromosome 14 open reading frame 160 [*Homo sapiens*] gb\|AAQ88880.1\| PFTL2439 [*Homo sapiens*] emb\|CAD61880.1\| unnamed protein product [*Homo sapiens*] emb\|CAD97934.1\| hypothetical protein [*Homo sapiens*] emb\|CAD62323.1\| unnamed protein product [*Homo sapiens*] |
| FLJ14467 | ref\|NP_067639.1\| serine carboxypeptidase 1 precursor protein [*Homo sapiens*]¥ gb\|AAG16692.1\| serine carboxypeptidase 1 precursor protein [*Homo sapiens*]¥ dbj\|BAB55069.1\| unnamed protein product [*Homo sapiens*]¥ gb\|AAQ88923.1\| HSCP1 [*Homo sapiens*] gb\|AAG39285.1\| MSTP034 [*Homo sapiens*] ref\|NP_596874.1\| retinoid-inducible serine carboxypeptidase [*Rattus norvegicus*]¥ gb\|AAK84661.1\| retinoid-inducible serine carboxypeptidase precursor [*Rattus norvegicus*] dbj\|BAB29501.1\| unnamed protein product [*Mus musculus*]¥ dbj\|BAC34111.1\| unnamed protein product [*Mus musculus*] gb\|AAK84662.1\| retinoid-inducible serine carboxypeptidase precursor [*Mus musculus*] |
| FLJ14583 | ref\|NP_808224.1\| Trophinin isoform 2; magphinin; MAGE superfamily protein [*Homo sapiens*]¥ ref\|NP_057241.2\| Trophinin isoform 2; magphinin; MAGE superfamily protein [*Homo sapiens*]¥ dbj\|BAB55149.1\| unnamed protein product [*Homo sapiens*] gb\|AAK30171.1\| magphinin beta[*Homo sapiens*] ref\|NP_808223.1\| Trophinin isoform 1; magphinin; MAGE superfamily protein [*Homo sapiens*]¥ gb\|AAH26914.1\| Trophinin, isoform1 [*Homo sapiens*] gb\|AAK30170.1\| magphinin alpha [*Homo sapiens*] dbj\|BAA83066.1\| KIAA1114protein [*Homo sapiens*] |

TABLE 5-3

| | |
|---|---|
| FLJ14797 | ref|NP_055259.1| gamma tubulin ring complex protein (76p gene) [Homo sapiens]¥ sp|Q9UGJ1|GCP4_human gamma-tubulin complex component 4 (GCP-4) (hGCP4) (h76p) (Hgrip76)¥ emb|CAB62539.1| gamma tubulin ring complex component protein [human] gb|AAH09870.1| gamma tubulin ring complex protein (76p gene) [Homo sapiens]¥ gb|AAH12801.1| gamma tubulin ring complex protein (76p gene) [Homo sapiens] ref|NP_700436.1| gamma tubulin ring complex protein [Mus musculus]¥ sp|Q9D4F8|GCP4_mouse gamma-tubulin complex component 4 (GCP-4)¥ gb|AAH29106.1| gamma tubulin ring complex protein [Mus musculus]¥ dbj|BAC32303.1| unnamed protein product [Mus musculus]¥ dbj|BAC32610.1| unnamed protein product [Mus musculus] dbj|BAC30170.1| unnamed protein product [Mus musculus] dbj|BAC34146.1| unnamed protein product [Mus musculus] |
| FLJ31146 | ref|NP_071768.2| hypothetical protein FLJ22313 [Homo sapiens]¥ gb|AAH05091.1| FLJ22313 protein [Homo sapiens]¥ gb|AAH20264.1| hypothetical protein FLJ22313 [Homo sapiens] gb|AAH29691.1| RIKEN cDNA 5031400M07 [Mus musculus] ref|NP_065611.1| RIKEN cDNA 5031400M07 [Mus musculus]¥ dbj|BAA95064.1| unnamed protein product [Mus musculus]¥ gb|AAH43693.1| RIKEN cDNA 5031400M07 [Mus musculus] dbj|BAB31889.1| unnamed protein product [Mus musculus] dbj|BAB15300.1| unnamed protein product [Homo sapiens] |

Nucleic Acid Analysis 2
Homology Analysis 2 by BLASTX

The calculation program used was blastall 2.2.6. The target databases used were swiss-prot:146720 (Mar. 29, 2004), (Refseq)hs:21170 (May 6, 2004), (Refseq)mouse:17089 (May 6, 2004), and (Refseq)rat:4893 (May 6, 2004). The cutoff value was established at 1.00E-05. The following data were processed by filtering:

For Swiss-Prot:
   Having a definition beginning with "ALU SUBFAMILY"
   Having a definition beginning with "Alu subfamily"
   Having a definition beginning with "!!!!ALU SUBFAMILY"
   Having a definition beginning with "B-CELL GROWTH FACTOR PRECURSOR"
   Having a definition including "NRK2"
   Having a definition beginning with "PROLINE-RICH"
   Having a definition beginning with "GLYCINE-RICH"
   Having a definition beginning with "EXTENSIN PRECURSOR"
   Having a definition beginning with "COLLAGEN"
   Having a definition beginning with "100KD"
   Having a definition beginning with "RETROVIRUS-RELATED POL POLYPROTEIN"
   Having a definition beginning with "CUTICLE COLLAGEN"
   Having a definition beginning with "HYPOTHETICAL"
   Having a definition beginning with "Hypothetical"
   Having a definition beginning with "SALIVARY PROLINE-RICH PROTEIN"
   Having a definition beginning with "IMMEDIATE-EARLY PROTEIN"
   Having the accession No "P49646"

For Ref-seq:
   Having a definition beginning with "hypothetical protein FLJ"
   Having a definition beginning with "KIAA"
   Having a definition beginning with "hypothetical protein DKFZ"
   Having a definition beginning with "DKFZ"
   Having a definition beginning with "RIKEN cDNA"
   Having a definition beginning with "hypothetical protein MGC"
   Having a definition as "hypothetical protein"
   Having a definition beginning with "hypothetical protein PP"
   Having a definition as "neuronal thread protein"
   Having a definition beginning with "clone FLB"
   Having a definition beginning with "hypothetical protein PRO"
   Having a definition as "PRO0483 protein"
   Having a definition including "MNC"
   Having a definition including "MOST-1"
   Having a definition beginning with "similar to"
   Having a definition including "TPR gene on Y"
   Having a definition beginning with "HSPC"
   Having a definition beginning with "CGI-"
   RefSeq sequence composed of self only (information referenced from LL_tmpl)

The annotation information obtained by this analysis is shown in Tables 6-1 to 6-3.

TABLE 6-1

| FLJ No. | accession No. and definition | keywords |
|---|---|---|
| FLJ10335 | Q9NW38 ubiquitin ligase protein PHF9 (EC 6.3.2.—) (FAAP43) Q9CR14 ubiquitin ligase protein PHF9 (EC 6.3.2.—) (Proliferation of germ cells protein) Q86Y07 serine/threonine protein kinase VRK2 (EC2.7.1.37) (Vaccinia-related kinase 2) NP_060532.1 Fanconi anemia, complementation group L; PHD finger protein 9 [Homo sapiens] NP_080199.1 Fanconi anemia, complementation group L; Proliferation of germ cells; PHD finger protein 9; germ cell deficient [Mus musculus] NP_006287.1 Vaccinia-related kinase 2; Vaccinia-related kinase-2 [Homo sapiens] | DNA repair; Ubl conjugation pathway; ligase; nuclear protein; metal bond; zinc; zinc-finger, alternative splicing transferase; serine/threonine protein kinase; ATP-binding; transmembrane; polymorphism |
| FLJ10889 | O35286 putative pre-mRNA splicing factor RNA helicase (DEAH box protein 15) O43143 putative pre-mRNA splicing factor RNA helicase (DEAH box protein 15) (ATP-dependent RNA helicase #46) O22899 putative pre-mRNA splicing factor ATP-dependent RNA helicase NP_060650.2 DEAD/H (Asp-Glu-Ala-Asp/His) box polypeptide 32 [Homo sapiens] NP_598702.1 helicase DDX32; DEAD/H (Asp-Glu-Ala-Asp/His) box polypeptide 32 [Mus musculus] NP_291084.1 DEAQ RNA-dependent ATPase [Mus musculus] | mRNA processing; mRNA splicing; helicase; ATP bond; nucleic protein. |
| FLJ11045 | Q9NUY9 tudor containing protein 4 Q9BXT4 tudor containing protein 1 Q99MV1 tudor containing protein 1 NP_061911.2 tudor domain-containing 4 [Homo sapiens] NP_942090.1 tudor domain-containing protein 1 [Homo sapiens] NP_113564.1 tudor domain-containing protein 1 [Mus musculus] | RNA-binding; mitochondrion; alternative splicing; outer membrane; transmembrane; transit peptide |

TABLE 6-2

| FLJ11474 | Q00808 Vegetatible incompatible protein HET-E-1 P78706 transcription repressor rco-1 Q9V3J8 Will die slowly protein NP_064372.2 G protein beta subunit-like; transducin (beta)-like 4 [Mus musculus] | GTP-binding; repeat; WD repeat conidiation; transcriptional control; repressor |

TABLE 6-2-continued

| | | |
|---|---|---|
| | NP_071799.1 G protein beta subunit-like; G beta-like protein [*Rattus norvegicus*] NP_071767.2 G protein beta subunit-like [*Homo sapiens*] | |
| FLJ12502 | NP_079228.3 chromosome 14 open reading frame 160 [*Homo sapiens*] | |
| FLJ14467 | Q9HB40 retinoid-inducible serine carboxypeptidase precursor (EC 3.4.16.—) (serine carboxypeptidase 1) (MSTP034) Q920A6 retinoid-inducible serine carboxypeptidase precursor (EC 3.4.16.—) Q920A5 retinoid-inducible serine carboxypeptidase precursor (EC 3.4.16.—) NP_067639.1 serine carboxypeptidase 1 precursor protein; promising homologue of rat and mouse retinoid-inducible serine carboxypeptidases [*Homo sapiens*] NP_596874.1 retinoid-inducible serine carboxypeptidase [*Rattus norvegicus*] NP_083299.2 serine carboxypeptidase1; retinoid-inducible serine carboxypeptidase, retinoid-inducible serine carboxypeptidase [*Mus musculus*] | hydrolase; carboxypeptidase; signal; glycoprotein; alternative splicing |
| FLJ14583 | Q12816 Trophinin (MAGE-D3 antigen) Q9UNF1 melanoma-associated antigen D2 (MAGE-D2 antigen) (MAGE-D) (breast cancer-related gene 1 protein) (BCG-1) (11B6) (hepatocellular carcinoma-associated protein JCL-1) Q9QYH6 melanoma-associated antigen D1 (MAGE-D1antigen) (Neurotrophin receptor-interacting MAGE homolog) (Dlxin-1) NP_808224.1 Trophinin isoform 2; magphinin; MAGE superfamily protein [*Homo sapiens*] NP_057241.2 Trophinin isoform 2; magphinin; MAGE superfamily protein [*Homo sapiens*] NP_808223.1 Trophinin isoform 1; magphinin; MAGE superfamily protein [*Homo sapiens*] | cell adhesion; antigen; repeat antigen; Multigene family; polymorphism; alternative splicing |
| FLJ14797 | Q9UGJ1 Gamma-tubulin complex component 4 (GCP-4) (hGCP4) (h76p) (Hgrip76) | microtubule |

TABLE 6-2-continued

| | | |
|---|---|---|
| | Q9D4F8 Gamma-tubulin complex component 4 (GCP-4) Q9M350 Gamma-tubulin complex component 4 homologue NP_055259.2 gamma tubulin ring complex protein (76p gene) [*Homo sapiens*] NP_700436.1 gamma tubulin ring complex protein [*Mus musculus*] NP_598516.1 tubulin, gamma complex associated protein 2 [*Mus musculus*] | |

TABLE 6-3

| | | |
|---|---|---|
| FLJ31146 | Q9JJK5 Homocysteine-responsive endoplasmic reticulum-resident ubiquitin-like domain member 1 protein Q15011 Homocysteine-responsive endoplasmic reticulum-resident ubiquitin-like domain member 1 protein (Methyl methanesulfonate (MMF)-inducible fragment protein 1) P20931 Very very hypothetical B-cell growth factor (BCGF-12 kDa) NP_071726.1 homocysteine-inducible, endoplasmic reticulum stress-inducible, ubiquitin-like domain member 1 [*Mus musculus*] NP_445975.1 homocysteine-inducible, endoplasmic reticulum stress-inducible, ubiquitin-like domain member 1 [*Rattus norvegicus*] NP_055500.1 homocysteine-inducible, endoplasmic reticulum stress-inducible, ubiquitin-like domain member 1; MMS-inducible gene [*Homo sapiens*] | unfold protein response; endoplasmic reticulum; transmembrane; alternative splicing |

Other examples of possible diseases or conditions are the diseases or conditions registered with OMIM. These diseases or conditions can easily be searched by, for example, inputting H-Inv ID numbers or H-Inv cluster ID numbers in H-Inv DB. The chromosomes where the genes for bioactive substances in this application are present, gene loci and gene cluster No. and OMIM information on orphan diseases expected to be associated with these genes, are respectively shown in Tables 7-1 to 7-2.

TABLE 7-1

| FLJ No. | chromosome | genome · locus | gene cluster | OMIM disease information (OMIM Co-localized orphan disease) |
|---|---|---|---|---|
| FLJ10335 | 2 | 58360917-58443015, minus | chr2 – 674 | OMIM605244: CARNEY COMPLEX, TYPE II; CNC2 OMIM604254: DYSLEXIA, SUSCEPTIBILITY TO, 3; DYX3 |
| FLJ10889 | 10 | | chr10 – 1639 | none |
| FLJ11045 | 13 | | chr13 + 69 | OMIM605844: DERMATITIS, ATOPIC, 5; ATOD5 |
| FLJ11474 | 16 | 2195129-2199321, plus | chr16 + 106 | none |
| FLJ12502 | 14 | 89570827-89681737, plus | chr14 + 855 | OMIM138800: GOITER, MULTINODULAR 1; MNG1 OMIM160500: MYOPATHY, DISTAL 1; MPD1 OMIM164210: HEMIFACIAL MICROSOMIA; HFM OMIM213600: FAHR DISEASE OMIM276900: USHER SYNDROME, TYPE IA; USH1A |

TABLE 7-2

| | | | | |
|---|---|---|---|---|
| FLJ14467 | 17 | 55530133-55558490, plus | chr17 + 1067 | OMIM154275: MALIGNANT HYPERTHERMIA, SUSCEPTIBILITY TO, 2; MHS2<br>OMIM168860: PATELLA APLASIA-HYPOPLASIA; PTLAH<br>OMIM249000: MECKEL SYNDROME, TYPE 1; MKS1<br>OMIM600852: RETINITIS PIGMENTOSA 17; RP17<br>OMIM602723: PSORIASIS SUSCEPTIBILITY 2; PSORS2 |
| FLJ14583 | X | | chrX + 442 | OMIM204300: CEROID LIPOFUSCINOSIS, NEURONAL, 4; CLN4<br>OMIM300047: MENTAL RETARDATION, X-LINKED 20; MRX20<br>OMIM300062: MENTAL RETARDATION, X-LINKED 14; MRX14<br>OMIM300115: MENTAL RETARDATION, X-LINKED 50; MRX50<br>OMIM301830: ARTHROGRYPOSIS MULTIPLEX CONGENITA, DISTAL, X-LINKED<br>OMIM300220: CHORIOATHETOSIS WITH MENTAL RETARDATION AND ABNORMAL BEHAVIOR<br>OMIM300136: DIABETES MELLITUS, INSULIN-DEPENDENT, X-LINKED, SUSCEPTIBILITY TO<br>OMIM309530: MENTAL RETARDATION, X-LINKED 1; MRX1<br>OMIM309545: MENTAL RETARDATION, NON-SPECIFIC X LINKED, WITH APHASIA; MRXA<br>OMIM300263: SIDERIUS X-LINKED MENTAL RETARDATION SYNDROME<br>OMIM-309610: PRIETO X-LINKED MENTAL RETARDATION SYNDROME; PRS<br>OMIM-309585: WILSON-TURNER X-LINKED MENTAL RETARDATION SYNDROME; WTS |
| FLJ14797 | 15 | 41379355-41413827, plus | chr15 + 375 | OMIM134600: FANCONI RENOTUBULAR SYNDROME<br>OMIM214900: CHOLESTASIS-LYMPHEDEMA SYNDROME<br>OMIM601228: COLORECTAL ADENOMA AND CARCINOMA 1; CRAC1<br>OMIM602099: AMYOTROPHIC LATERAL SCLEROSIS 5; ALS5<br>OMIM604321: MICROCEPHALY, PRIMARY AUTOSOMAL RECESSIVE, 4; MCP<br>OMIM604329: HYPERTENSION, ESSENTIAL, SUSCEPTIBILITY TO, 2<br>OMIM605738: MICROPHTHALMIA 2; NNO2<br>OMIM605275: NOONAN SYNDROME 2<br>OMIM604360: SPASTIC PARAPLEGIA 11, AUTOSOMAL RECESSIVE; SPG11 |
| FLJ31146 | 7 | | chr7 − 422 | none |

Other possible diseases or conditions are diseases or conditions accompanied by abnormalities at expression sites of target gene Y, or in tissues from which the source library for target gene Y is derived. The expression sites and tissues can easily be searched by, for example, inputting H-Inv ID numbers or H-Inv cluster ID numbers in H-Inv DB, whereby those skilled in the art are able to postulate the diseases or conditions.

For example, some of target gene Y are expressed at the sites shown below.

The FLJ10335-derived gene can be expressed in the brain stem, cerebellum, corpus callosum, glia, spinal cord, spleen, uterus, prostate, testis, heart, muscles, colon, liver, lungs, kidneys, adrenals, mammary glands, pituitary and the like.

The FLJ10889-derived gene can be expressed in the brain stem, cerebellum, corpus callosum, glia, retina, aorta, skin, ovary, placenta, prostate, testis, heart, muscles, colon, stomach, liver, lungs, adrenals, mammary glands, pancreas and the like.

The FLJ11045-derived gene can be expressed in the brain stem, placenta, testis, heart, colon, pancreas and the like.

The FLJ11474-derived gene can be expressed in the cerebrum, cerebellum, eyes, spinal cord, uterus, ovary, prostate, testis, muscles, colon, liver, lungs, kidneys, adrenals, mammary glands, pancreas and the like.

The FLJ12502-derived gene can be expressed in the brain stem, cerebellum, lymph nodes, blood, spleen, prostate, testis, heart, muscles, colon, stomach, liver, lungs, kidneys, adrenals, pancreas, pituitary and the like.

The FLJ14467-derived gene can be expressed in the brain stem, cerebellum, retina, bone marrow, spleen, bone, skin, uterus, ovary, placenta, prostate, testis, heart, muscles, colon, small intestine, lungs, kidneys, adrenals, mammary glands, pituitary, thyroid and the like.

The FLJ14583-derived gene can be expressed in the brain stem, cerebrum, cerebellum, corpus callosum, glia, spinal cord, bone marrow, bone, skin, ovary, placenta, prostate, testis, heart, muscles, small intestine, liver, lungs, mammary glands, pancreas, pituitary, salivary gland and the like.

The FLJ14797-derived gene can be expressed in the brain stem, cerebellum, corpus callosum, glia, spinal cord, bone marrow, thymus, placenta, prostate, testis, muscles, colon, liver, lungs, kidneys, mammary glands, pancreas, pituitary and the like.

The FLJ31146-derived gene can be expressed in the brain stem, cerebrum, eyes, spleen, thymus, bone, skin, uterus, placenta, prostate, testis, muscles, colon, lungs, adrenals, mammary glands and the like.

The target proteins and target genes of the present invention are useful for, for example, the development of drugs for specified diseases or conditions, or the development of investigational reagents for the diseases or conditions.

2. Screening Methods and Products Obtained by the Methods

The present invention provides screening methods for bioactive substances, each of which comprises determining whether or not a test substance is capable of regulating the expression or function of a target protein for the bioactive substance or a gene that encodes the protein (hereinafter sometimes abbreviated as "target protein Y" or "target gene Y" as required), and a product thereof. From the viewpoint of the kind of bioactive substance screened, the screening methods of the present invention can be roughly divided into screening methods for substances capable of regulating an action associated with bioactive substance X, and screening methods for substances capable of regulating a function associated with target protein Y. The screening methods of the present invention can also be performed in vitro, in vivo or in silico. The substances capable of regulating an expression of target protein Y obtained by the screening method of the present invention are the same as the substances capable of regulating the amount of target protein Y, can be substances capable of changing the amount of target protein Y in a given tissue or cell, or the amount of target protein Y at a given intracellular position. Accordingly, the substances capable of regulating expression of target protein Y include, for example, not only substances capable of regulating the biosynthesis of target protein Y from target gene Y, but also substances capable of regulating intracellular localization of target protein Y, substances capable of regulating biodynamics of target protein Y, and substances capable of regulating the metabolism of target protein Y (e.g., synthesis, degradation by metabolism). The individual screening methods are hereinafter described in detail.

2.1. Screening Methods for Substances Capable of Regulating Action Associated with Bioactive Substance X (Screening Method I)

The present invention provides screening methods for substances capable of regulating an action associated with bioactive substance X, each of which comprises determining whether or not a test substance is capable of regulating the expression or function of target protein Y.

The screening methods of this type are generically referred to as "screening method I" as required.

Screening method I can be roughly divided into a screening method for a substance capable of regulating an action associated with bioactive substance X, which comprises determining whether or not a test substance is capable of regulating the expression or function of target protein Y, and selecting a test substance capable of regulating the expression or function of target protein Y (screening method Ia), and a screening method for a substance capable of regulating an action associated with bioactive substance X (particularly an action associated with a known target molecule), which comprises determining whether or not a test substance is capable of regulating the expression or function of target protein Y, and selecting a test substance that is incapable of regulating the expression or function of target protein Y (screening method Ib). Screening method Ia can be useful for the development of regulators of diseases or conditions associated with bioactive substance X and the like. Screening method Ib can be useful for the development of drugs capable of regulating an action associated with a known target molecule, and showing decreased adverse effects of bioactive substance X and the like.

2.1.1. Screening Method for Substances Capable of Regulating Action Associated with Bioactive Substance X, which Comprises Selecting Test Substance Capable of Regulating Expression or Function of Target Protein Y (Screening Method Ia)

The present invention provides a screening method for substances capable of regulating an action associated with bioactive substance X, which comprises determining whether or not a test substance is capable of regulating the expression or function of target protein Y, and selecting a test substance capable of regulating the expression or function of target protein Y.

The test substance subjected to this screening method may be any known compound or new compound; examples include nucleic acids, saccharides, lipids, proteins, peptides, organic small compounds, compound libraries prepared using combinatorial chemistry technique, random peptide libraries prepared by solid phase synthesis or the phage display method, or natural components derived from microorganisms, animals, plants, marine organisms and the like, and the like.

The test substance may be a labeled supply or a non-labeled supply, or a mixture of a labeled supply and a non-labeled supply mixed in a specified ratio. The labeling substance is the same as described above.

In one embodiment, screening method Ia comprises the following steps (a), (b) and (c):
(a) a step for bringing the test substance into contact with target protein Y;
(b) a step for measuring the functional level of the protein in the presence of the test substance, and comparing this functional level with the functional level of the protein in the absence of the test substance;
(c) a step for selecting a test substance that alters the functional level of the protein on the basis of the result of the comparison in step (b) above.

The methodology comprising the above-described steps (a) to (c) is referred to as "methodology I" as required.

In step (a) of methodology I, a test substance is brought into contact with target protein Y. Contact of the test substance with the protein can be performed by contact of isolated target protein Y and the test substance in solution, or contact of cells or tissue capable of expressing target protein Y and the test substance.

Target protein Y can be prepared by a method known per se. For example, target protein Y can be isolated and purified from the above-described expression tissue. However, to prepare target protein Y quickly, easily, and in large amounts, and to prepare human target protein Y, it is preferable to prepare a recombinant protein by gene recombination technology. The recombinant protein may be prepared using a cell system or a cell-free system.

The cells capable of expressing target protein Y can be any cells that express target protein Y; examples include cells derived from the tissue in which target protein Y is expressed, cells transformed with target protein Y expression vector and the like. Those skilled in the art are able to easily identify or prepare these cells; useful cells include primary culture cells, cell lines derivatively prepared from the primary culture cells, commercially available cell lines, cell lines available from cell banks, and the like. As the tissue capable of expressing target protein Y, the above-described expression tissues can be used.

In step (b) of methodology I, the functional level of the protein in the presence of the test substance is measured. A measurement of the functional level can be performed according to the kind of protein by a method known per se. For example, provided that target protein Y is a transcription factor, a substance that regulates a function associated with target protein Y can be screened by performing a reporter assay using target protein Y and a transcription regulatory region to which it binds.

Provided that target protein Y is an enzyme, the functional level can also be measured on the basis of a change in the catalytic activity of the enzyme. The catalytic activity of the enzyme can be measured by a method known per se using a substrate, coenzyme and the like chosen as appropriate according to the kind of enzyme.

Furthermore, provided that target protein Y is a membrane protein (e.g., receptors, transporters), the functional level can be measured on the basis of a change in a function of the membrane protein. For example, provided that target protein Y is a receptor, a screening method of the present invention can be performed on the basis of an intracellular event mediated by the receptor (e.g., inositol phospholipid production, intracellular pH change, intracellular behavior of ions such as calcium ion and chloride ion). Provided that target protein Y is a transporter, the screening methods of the present invention can be performed on the basis of a change in the intracellular concentration of a substrate for the transporter.

The functional level may also be measured on the basis of the functional level of target protein Y to each isoform (e.g., splicing variant) or the isoform-isoform functional level ratio, rather than on the basis of the total functional level of target protein Y.

Next, the functional level of target protein Y in the presence of the test substance is compared with the functional level of target protein Y in the absence of the test substance. This comparison of functional level is preferably performed on the basis of the presence or absence of a significant difference. Although the functional level of target protein Y in the absence of the test substance may be measured prior to, or simultaneously with, the measurement of the functional level of target protein Y in the presence of the test substance, it is preferable, from the viewpoint of experimental accuracy and reproducibility, that the functional level be measured simultaneously.

In step (c) of methodology I, a test substance that alters the functional level of the protein is selected. The test substance that alters the functional level of the protein is capable of promoting or suppressing a function of target protein Y. The test substance thus selected can be useful for the regulation of a disease or condition associated with bioactive substance X.

Methodology I may be performed not only in the presence of target protein Y but also with a coupling factor thereof. For example, when a target protein Y inhibitory factor is used in combination as the coupling factor of target protein Y, a substance that interferes with the interaction between target protein Y and the coupling factor is considered to be capable of promoting a function of target protein Y. When a target protein Y activation factor is used in combination as the coupling factor for target protein Y, a substance that interferes with the interaction between target protein Y and the coupling factor is considered to be capable of suppressing a function of target protein Y. Hence, it is also beneficial to perform methodology I in the presence of a coupling factor of target protein Y.

In another embodiment, screening method Ia comprises the following steps (a), (b) and (c):
(a) a step for bringing the test substance into contact with a cell capable of measuring the expression of target gene Y;
(b) a step for measuring the expression level of the target gene Y in the cell contacted with the test substance, and comparing this expression level with the expression level of the target gene Y in the control cell free of contact with the test substance;
(c) a step for selecting a test substance that regulates the expression level of the target gene Y on the basis of the result of the comparison in step (b) above.

The methodology comprising the above-described steps (a) to (c) is referred to as "methodology II" as required.

In step (a) of methodology II, a test substance is brought into contact with cells capable of measuring the expression of target gene Y. The contact of a test substance with cells capable of measuring the expression of target gene Y can be performed in a culture medium.

"Cells capable of measuring the expression of target gene Y (or gene corresponding to the target protein Y)" refers to cells enabling a direct or indirect evaluation of the expression level of a product of target gene Y, for example, a transcript or translation product. The cells enabling a direct evaluation of the expression level of a product of target gene Y can be cells capable of naturally expressing target gene Y, whereas the cells enabling an indirect evaluation of the expression level of a product of target gene Y can be cells enabling a reporter assay on the target gene Y transcription regulatory region.

The cells capable of naturally expressing target gene Y can be any cells that potentially express target gene Y; examples include cells showing permanent expression of target gene Y, cells that express target gene Y under inductive conditions (e.g., drug treatment) and the like. Those skilled in the art are able to easily identify these cells; useful cells include primary culture cells, cell lines induced from the primary culture cells, commercially available cell lines, cell lines available from cell banks, and the like.

The cells enabling a reporter assay on the target gene Y transcription regulatory region are cells incorporating the target gene Y transcription regulatory region and a reporter gene functionally linked to the region. The target gene Y transcription regulatory region and reporter gene are inserted in an expression vector.

The target gene Y transcription regulatory region may be any region enabling the control of the expression of target gene Y; examples include a region from the transcription initiation point to about 2 kbp upstream thereof, and a region consisting of a base sequence wherein one or more bases are deleted, substituted or added in the base sequence of the region, and that is capable of controlling the transcription of target gene Y, and the like.

The reporter gene may be any gene that encodes a detectable protein or enzyme; examples include the GFP (green fluorescent protein) gene, GUS (β-glucuronidase) gene, LUS (luciferase) gene, CAT (chloramphenicol acetyltransferase) gene and the like.

The cells transfected with the target gene Y transcription regulatory region and a reporter gene functionally linked to the region are not subject to limitation, as long as they enable an evaluation of the target gene Y transcription regulatory function, that is, as long as they enable a quantitative analysis of the expression level of the reporter gene. However, the cells transfected are preferably cells capable of naturally expressing target gene Y because they are considered to express a physiological transcription regulatory factor for target gene Y, and to be more appropriate for the evaluation of the regulation of the expression of target gene Y.

The culture medium in which a test substance and cells enabling a measurement of the expression of target gene Y are brought into contact with each other is chosen as appropriate according to the kind of cells used and the like; examples include minimal essential medium (MEM) containing about 5 to 20% fetal bovine serum, Dulbecco's modified minimal essential medium (DMEM), RPMI1640 medium, 199 medium and the like. Culture conditions are also determined as appropriate according to the kind of cells used and the like; for example, the pH of the medium is about 6 to about 8, culture temperature is normally about 30 to about 40° C., and culture time is about 12 to about 72 hours.

In step (b) of methodology II, first, the expression level of target gene Y in the cells in contact with the test substance is measured. This measurement of expression level can be performed by a method known per se in view of the kind of cells used and the like.

For example, when cells capable of naturally expressing target gene Y are used as the cells enabling a measurement of the expression of target gene Y, the expression level can be measured by a method known per se with a product of target gene Y, for example, a transcription product or translation product, as the subject. For example, the expression level of a transcription product can be measured by preparing total RNA from the cells, and performing RT-PCR, Northern blotting and the like. The expression level of a translation product can be measured by preparing an extract from the cells, and performing an immunological technique. Useful immunological techniques include radioisotope immunoassay (RIA), ELISA (Methods in Enzymol. 70: 419-439 (1980)), fluorescent antibody method and the like.

When cells enabling a reporter assay on the target gene Y transcription regulatory region are used as the cells enabling a measurement of the expression of target gene Y, the expression level can be measured on the basis of the signal intensity of the reporter.

The expression level may also be measured on the basis of the expression level of target gene Y to each isoform (e.g., splicing variant) or the isoform-isoform expression ratio, rather than on the basis of the total functional level of target gene Y.

Moreover, when target gene Y is a gene of an intracellularly localized factor, the expression amount can also be measured based on the intracellular localization. The amount of target protein Y localized in a given intracellular organelle can be measured by a method known per se. For example, provided that target gene Y is a gene for an intracellularly localized factor, screening method I can be performed on the basis of a change in the intracellular localization of target protein Y. The amount of target protein Y localized in a specified organelle can be measured by a method known per se. For example, target gene Y, previously fused with a gene that encodes a fluorescent protein, such as the GFP gene, is introduced to an appropriate cell and cultured in culture medium in the presence of a test substance. Next, a fluorescence signal in the specified organelle is examined using a confocal microscope, and this signal is compared with the fluorescence signal in the absence of the test substance in the same organelle. The amount of target protein Y localized in the specified organelle can also be measured by immunostaining using an antibody against target protein Y.

Next, the expression level of target gene Y in the cells in contact with the test substance is compared with the expression level of target gene Y in control cells not in contact with the test substance. This comparison of expression level is preferably performed on the basis of the presence or absence of a significant difference. Although the expression level of target gene Y in the control cells not in contact with the test substance may be measured prior to, or simultaneously with, the measurement of the expression level of target gene Y in the cells in contact with the test substance, it is preferable, from the viewpoint of experimental accuracy and reproducibility, that the expression level be measured simultaneously.

In step (c) of methodology II, a test substance that regulates the expression level of target gene Y is selected. The regulation of the expression level of target gene Y can be the promotion or suppression of the expression level. The test substance thus selected can be useful for the regulation of an action associated with bioactive substance X.

In another embodiment, screening method Ia comprises the following steps (a), (b) and (c):
(a) a step for bringing the test substance into contact with target protein Y or a mutant protein thereof having a binding ability to bioactive substance X;
(b) a step for measuring the ability of the test substance to bind to the protein;
(c) a step for selecting a test substance capable of binding to the protein on the basis of the results of step (b) above.

The methodology comprising the above-described steps (a) to (c) is referred to as "methodology III" as required.

In step (a) of methodology III, a test substance is brought into contact with target protein Y or a mutant protein thereof.

Contact of the test substance with the protein can be performed by mixing the test substance and the protein in solution.

Target protein Y can be prepared by a method known per se. For example, target protein Y can be isolated and purified from the above-described target gene Y-expressing tissue. However, to prepare target protein Y quickly, easily, and in large amounts, and to prepare human target protein Y, it is preferable to prepare a recombinant protein by gene recombination technology. The recombinant protein may be prepared using a cell system or a cell-free system. Those skilled in the art can also easily prepare a mutant protein capable of binding to bioactive substance X by a method known per se. The mutant protein is the same as described above.

In step (b) of methodology III, the ability of the test substance to bind to the protein is measured. A measurement of the bindability can be performed by a method known per se. In addition to the bindability, binding strength, the concentration dependency of the test substance in the binding to the protein, and the like can further be measured. Binding strength and concentration dependency can be measured using appropriately chosen means of measurement.

A measurement of the binding ability can be performed by, for example, the SEC/MS method (size exclusion chromatography/mass analysis) (see Moy, F. J. et al., Anal. Chem., 2001, 73, 571-581). The SEC/MS method comprises (1) a step for adding a mixed multiplied compound standard to the purified protein, and then separating the free compound and the protein by SEC, and (2) an analytical step for identifying the bound compound contained in the protein fraction by MS. The SEC/MS method is advantageous in that the binding ability can be analyzed while both the protein and the test substance are in non-modified and non-immobilized state. In the SEC/MS method, not only the ability of the test substance to bind to the protein, but also the concentration dependency of the test substance in the binding to the protein and the like can be measured simultaneously.

A measurement of the binding ability can also be performed using a means for measurement based on surface plasmon resonance, for example, Biacore. Using Biacore, the binding and dissociation of a test substance to a protein immobilized on a chip are measured, and the measured values are compared with those obtained when a solution not containing the test substance is loaded on the chip.

Subsequently, a test substance capable of binding to the protein is selected on the basis of the result for the binding and dissociation rate or binding level. Biacore also enables simultaneous measurements of binding strength (e.g., $K_d$ value) and the like, in addition to the ability of a test substance to bind to a protein.

Other methods for measuring the binding ability include, for example, SPR-based methods or optical methods such as the quartz crystal microbalance (QCM) method, the dual polarization interferometer (DPI) method, and the coupled waveguide plasmon resonance method, immunoprecipitation, isothermal titration and differential scanning calorimetry, capillary electrophoresis, energy transfer, fluorescent analytical methods such as fluorescent correlation analysis, and structural analytical methods such as X-ray crystallography and nuclear magnetic resonance (NMR).

In measuring the binding ability, a target protein Y-binding substance can also be used as a control.

"A target protein Y-binding substance" is a compound capable of interacting directly with target protein Y or a mutated protein thereof, and can be, for example, a protein, a nucleic acid, a carbohydrate, a lipid, or a small organic compound. Preferably, the target protein Y-binding substance can be selected from among cefaclor, ubenimex, aclarubicin, cefadroxil, ursolic acid, dicloxacillin, ketanserin and ampicillin, or a derivative thereof (described later) capable of binding to target protein Y (determined according to the kind of bioactive substance X), or a salt thereof.

Although the salts may be any salts, pharmaceutically acceptable salts are preferable; examples include salts with inorganic bases (e.g., alkali metals such as sodium and potassium; alkaline earth metals such as calcium and magnesium; aluminum, ammonium), salts with organic bases (e.g., trimethylamine, triethylamine, pyridine, picoline, ethanolamine, diethanolamine, triethanolamine, dicyclohexylamine, N,N-dibenzylethylenediamine), salts with inorganic acids (e.g., hydrochloric acid, hydrobromic acid, nitric acid, sulfuric acid, phosphoric acid), salt with organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), salts with basic amino acids (e.g., arginine, lysine, ornithine) or salts with acidic amino acids (e.g., aspartic acid, glutamic acid) and the like.

Furthermore, the binding ability may also be measured on the basis of the binding ability of target protein Y to each isoform (e.g., splicing variant) or the isoform-isoform binding ability ratio, rather than on the basis of the total binding ability of target protein Y.

The binding ability can also be measured in silico. For example, a measurement of the binding ability can be performed on the basis of SBDD (structure-based drug design: SBDD) or CADD (computer-aided drug design). Examples of such screening include virtual screening, de novo design, pharmacophore analysis, QSAR (quantitative structure activity relationship) and the like. If information on the steric structure of the protein or the target site of the protein is required during such screening, the information on the steric structure is used, provided that the steric structure is known by a structural analytical technique such as NMR, X-ray crystallographic analysis, or synchrotron radiation analysis. If the steric structure is unknown, information obtained by a structural estimation method such as the homology method or the threading method is used. In virtual screening, a program known per se can be used; examples of the program include DOCK (Kuntz, I. D. et al., Science, 1992, 257, 1078), Gold (Jones, G. et al., J. Mol. Biol., 1995, 245, 43), FlexX (Rarey, M. et al., J. Mol. Biol., 1996, 261, 470), AutoDock (Morris, G. M. et al., J. Comput. Chem., 1998, 19, 1639), ICM (Abagyan, R. A. et al., J. Comput. Chem., 1994, 15, 488) and the like.

In step (c) of methodology III, a test substance capable of binding to target protein Y or a mutant protein thereof is selected. The test substance capable of binding to the protein is capable of promoting or suppressing a function of target protein Y. The test substance thus selected can be useful for the regulation of a disease or condition associated with bioactive substance X.

In still another mode of embodiment, screening method Ia comprises the following steps (a), (b) and (c):

(a) a step for bringing the test substance and a target protein Y-binding substance into contact with target protein Y or a mutant protein thereof having a binding ability to a bioactive substance;

(b) a step for measuring the binding level of the target protein Y-binding substance to the protein in the presence of the test substance, and comparing this binding level with the binding level of the target protein Y-binding substance to the protein in the absence of the test substance;

(c) a step for selecting a test substance that alters the binding level of the target protein Y-binding substance to bind to the protein on the basis of the result of the comparison in step (b) above.

The methodology comprising the above-described steps (a) to (c) is referred to as "methodology IV" as required.

In step (a) of methodology IV, both a test substance and a target protein Y-binding substance are brought into contact with target protein Y or a mutant protein thereof. Contact of the test substance and the target protein Y-binding substance with the protein can be performed by mixing the test substance, the target protein Y-binding substance, and the protein in solution. The order of bringing the test substance and target protein Y-binding substance into contact with the protein is not subject to limitation; one of them may be brought into contact with the protein at a time lag or at the same time.

Target protein Y and a mutant protein thereof having a binding ability to bioactive substance X can be prepared by a method known per se. For example, preparation of the protein can be performed by a method described in methodology III above.

The target protein Y-binding substance may be a labeled supply or a non-labeled supply, or a mixture of a labeled supply and a non-labeled supply mixed in a specified ratio. The labeling substance is the same as described above.

In step (b) of methodology IV, first, the binding level of the target protein Y-binding substance to the protein is measured in the presence of the test substance. A measurement of the binding level can be performed by a method known per se, in view of the kind of target protein Y-binding substance used, the presence or absence of a label, and the like. In addition to the binding level, binding strength (e.g., $K_d$ value), the concentration dependency of the test substance in the binding to the protein, and the like can further be measured. Binding strength and concentration dependency can be measured using appropriately chosen means of measurement.

A measurement of the binding level can be performed using, for example, a labeled target protein Y-binding substance. The target protein Y-binding substance bound to the protein and the unbound target protein Y-binding substance may be separated before measuring the binding level.

A measurement of the binding level can also be performed by, for example, a means of measurement based on the SEC/MS method (size exclusion chromatography/mass analysis) or surface plasmon resonance described in methodology III above.

Other methods for measuring the binding level include, for example, the QCM method, the DPI method, SPR-based methods or optical methods such as the coupled waveguide plasmon resonance method, immunoprecipitation, isothermal titration and differential scanning calorimetry, capillary electrophoresis, energy transfer, fluorescent analytical methods such as fluorescent correlation analysis, and structural analytical methods such as X-ray crystallography and nuclear magnetic resonance (NMR).

The binding ability may also be measured on the basis of the binding ability of target protein Y to each isoform (e.g., splicing variant) or the isoform-isoform binding ability ratio, rather than on the basis of the total amount of target protein Y bound.

Next, the binding level of the target protein Y-binding substance to the protein in the presence of the test substance is compared with the binding level of the target protein Y-binding substance to the protein in the absence of the test substance. This comparison of the binding level is preferably performed on the basis of a significant difference. Although the binding level of the target protein Y-binding substance to the protein in the absence of the test substance may be measured prior to, or simultaneously with, the measurement of the binding level of the target protein Y-binding substance to the protein in the presence of the test substance, it is preferable, from the viewpoint of experimental accuracy and reproducibility, that the binding level be measured simultaneously.

In step (c) of methodology IV, a test substance that alters the binding level of the target protein Y-binding substance to the protein is selected. The change in the binding level can be, for example, a reduction or increase of binding level, with preference given to a reduction of binding level. Hence, the selected test substance can be useful for the regulation of an action associated with bioactive substance X.

Screening method Ia can further comprise (d) (i) a step for confirming that the selected test substance is capable of regulating, for example, promoting or suppressing, an action associated with bioactive substance X (confirmation step), or (ii) a step for identifying the kind of action exhibited by the selected test substance (identification step). The confirmation step or identification step can be performed by, for example, administering the selected test substance to a normal animal, or to an animal with "a disease or condition associated with bioactive substance X" or model animal. Alternatively, these steps can also be performed by contacting a test substance with a cell and evaluating changes in a phenotype of the cell after the contact. According to this identification step, the kind of "action associated with bioactive substance X" possessed by the selected test substance can be determined, and whether or not the selected test substance can be used as either a drug or an investigational reagent, or both, and the kind of drug or investigational reagent to which the test substance is applicable can be confirmed.

Screening method Ia can also be performed by administration of a test substance to an animal. In this case, for example, not only the expression amount of target gene Y but also expression amount of the target protein Y (e.g., the amount of target protein Y present in a given tissue or cell of animal administered with the test substance, intracellularly localized amount) can also be measured. Examples of the animal include mammals such as mice, rats, hamsters, guinea pigs, rabbits, dogs, and monkeys, and birds such as chickens. When a screening method of the present invention is performed using an animal, for example, a test substance that regulates the expression level of target gene Y can be selected.

Screening method Ia can be performed by various methodologies according to the kind of target gene Y. For example, provided that target gene Y is a transcription factor gene, a substance that regulates a function associated with target gene Y can be screened by performing a reporter assay using target protein Y and a transcription regulatory region to which it binds.

Provided that target gene Y is a gene for an intracellularly localized factor, screening method Ia can be performed on the basis of a change in the intracellular localization of target protein Y. The amount of target protein Y localized in a specified organelle can be measured by a method known per se. For example, target gene Y, previously fused with a gene that encodes a fluorescent protein, such as the GFP gene, is introduced to an appropriate cell and cultured in culture medium in the presence of a test substance. Next, a fluorescence signal in the specified organelle is examined using a confocal microscope, and this signal is compared with the fluorescence signal in the absence of the test substance in the same organelle. The amount of target protein Y localized in the specified organelle can also be measured by immunostaining using an antibody against target protein Y.

Provided that target protein Y is an enzyme gene, screening method Ia can also be performed on the basis of a change in the catalytic activity of the enzyme. The catalytic activity of the enzyme can be measured by a method known per se using a substrate, coenzyme and the like chosen as appropriate according to the kind of enzyme.

Furthermore, provided that target gene Y is a gene of a membrane protein (e.g., receptors, transporters), screening method I can be performed on the basis of a change in a function of the membrane protein. For example, provided that target gene Y is a receptor gene, a screening method of the present invention can be performed on the basis of an intracellular event mediated by the receptor (e.g., inositol phospholipid production, intracellular pH change, intracellular behavior of ions such as calcium ion and chlorine ion). Provided that target gene Y is a transporter gene, a screening method of the present invention can be performed on the basis of a change in the intracellular concentration of a substrate for the transporter.

Furthermore, provided that target gene Y is a gene for a soluble (secretory) factor, screening method Ia can be performed on the basis of a change in the blood concentration of the factor in the animal. Administration of the test substance to the animal, blood drawing from the animal, and the measurement of the blood concentration of the factor can be performed by a method known per se.

Screening method Ia enables screening of a substance capable of regulating an action associated with bioactive substance X. Hence, screening method Ia is useful for the development of a prophylactic or therapeutic agent for a disease or condition associated with bioactive substance X, an investigational reagent for the disease or the condition, and the like.

2.1.2. Screening Method for Substances Capable of Regulating Action Associated with Bioactive Substance X, which Comprises Selecting Test Substance Incapable of Regulating Expression or Function of Target Protein Y (Screening Method Ib)

The present invention provides a screening method for substances capable of regulating an action associated with bioactive substance X (particularly an action associated with a known target molecule and/or a pharmacological action that bioactive substance X actually shows), (e.g., a substance having a pharmacological action that bioactive substance X actually shows, which is usable for pharmaceutical use similar to that of bioactive substance X, and free of side effects that bioactive substance X actually shows or with reduced side effects), which comprises determining whether or not a test substance is capable of regulating the expression or function of target protein Y, and selecting a test substance incapable of regulating the expression or function of target protein Y.

Screening method Ib can be performed in the same manner as methodologies I to IV except that a test substance that does not cause a change or does not have the binding ability or regulatory capacity in step (c) of the above-described methodologies I to IV is selected.

In screening method Ib, the test substance to be used can be one capable of regulating the expression or function of a known target molecule, or has an action associated with bioactive substance X (particularly, a pharmacological action that bioactive substance X actually shows). Accordingly, screening method Ib can be used in combination with a screening method of a substance capable of regulating an action relating to a known target molecule, which comprises evaluating whether or not a test substance can regulate the expression or function of a known target molecule. The screening method for a substance capable of regulating an action relating to a known target molecule can be performed in the same manner as in the aforementioned screening method Ia. Alternatively, screening method Ib can be used in combination with a screening method of a substance capable of regulating an action associated with bioactive substance X, which comprises evaluating whether or not a test substance can regulate an action associated with bioactive substance X (particularly, a pharmacological action that bioactive substance X actually shows). Such screening method can be performed in the same manner as in the aforementioned screening method Ia, step (d) using an animal or cell.

Screening method Ib enables the development of drugs capable of regulating an action associated with a known target molecule and/or having a pharmacological action that a bioactive substance X actually shows, and showing decreased adverse effects of bioactive substance X. Hence, screening method Ib is useful for the improvement of existing drugs capable of regulating an action associated with a known target molecule and the like.

2.2. Screening Method for a Substance Capable of Regulating a Function Associated with Target Gene Y (Screening Method II)

The present invention provides a screening method for a substance capable of regulating a function associated with target gene Y, which comprises determining whether or not a test substance is capable of regulating the bindability of bioactive substance X to target protein Y or a mutant protein thereof capable of binding to bioactive substance X.

This screening method is referred to as "screening method II" as required.

In one embodiment, screening method II comprises the following steps (a), (b) and (c):
(a) a step for bringing the test substance into contact with target protein Y;
(b) a step for measuring the functional level of the protein in the presence of the test substance, and comparing this functional level with the functional level of the protein in the presence of bioactive substance X;
(c) a step for selecting a test substance that alters the functional level of the protein on the basis of the result of the comparison in step (b) above.

The methodology comprising the above-described steps (a) to (c) is the same as methodology I except that the reference control for step (b) is not "the functional level of target protein Y in the absence of the test substance" but "the functional level of target protein Y in the presence of bioactive substance X".

In another embodiment, screening method II comprises the following steps (a), (b) and (c):
(a) a step for bringing the test substance and cells enabling a measurement of the expression of target protein Y or a gene that encodes the protein into contact with each other;
(b) a step for measuring the expression level in the cells in contact with the test substance, and comparing this expression level with the expression level in control cells in contact with bioactive substance X;
(c) a step for selecting a test substance that regulates the expression level on the basis of the result of the comparison in step (b) above.

The methodology comprising the above-described steps (a) to (c) is the same as methodology II except that the reference control for step (b) is not "the expression level in control cells not in contact with the test substance" but "the expression level in control cells in contact with bioactive substance X".

In one mode of embodiment, screening method II comprises the following steps (a), (b) and (c):

(a) a step for bringing a test substance and bioactive substance X into contact with target protein Y or a mutant protein thereof capable of binding to bioactive substance X;
(b) a step for measuring the binding level of bioactive substance X to the protein in the presence of the test substance, and comparing this binding level with the binding level of bioactive substance X to the protein in the absence of the test substance;
(c) a step for selecting a test substance that alters the binding level of bioactive substance X to the protein on the basis of the results of the comparison in step (b) above.

The methodology comprising the above-described steps (a) to (c) is the same as methodology IV except that the "bioactive substance X" is used instead of the "target protein Y binding substance".

Screening method II enables, for example, screening of substances capable of regulating a function associated with target gene Y, probes for target gene Y, and the like. Hence, screening method II is useful for the screening of prophylactic or therapeutic agents for diseases or conditions associated with target gene Y, screening of investigational reagents for the diseases or conditions, and the like.

2.3. Products Obtained by Screening Methods

The present invention provides products obtained by the above-described screening methods, for example, screening methods I and II.

A product provided by a screening method of the present invention can be a substance obtained by a screening method of the present invention, or a bioactivity regulator comprising a substance obtained by the screening method (described later).

A product provided by a screening method of the present invention is useful for, for example, the prevention or treatment of a disease or condition associated with bioactive substance X, or a disease or condition associated with target gene Y, or as an investigational reagent for the disease or the condition, and the like.

3. Regulators

The present invention provides bioactivity regulators each comprising a substance that regulates the expression or function of a target gene for a bioactive substance. From the viewpoint of the bioactivity regulated, the regulators of the present invention can be roughly divided into regulators of actions associated with bioactive substance X, and regulators of functions associated with target gene Y. The individual regulators are hereinafter described in detail.

3.1. Regulators of Actions Associated with Bioactive Substance X (Regulator I)

The present invention provides a type of regulators of actions associated with bioactive substance X, each of which comprises a substance that regulates the expression or function of target gene Y.

The regulators of this type are generically referred to as "regulator I" as required.

The substance that regulates the expression or function of target gene Y can be, for example, a substance that suppresses the expression of target gene Y. The expression refers to a state in which a target gene Y translation product is produced and is localized at the action site thereof in a functional condition. Hence, the substance that suppresses the expression may be one that acts in any stage of gene transcription, post-transcriptional regulation, translation, post-translational modification, localization and protein folding and the like.

Specifically, the substance that suppresses the expression of target gene Y is exemplified by transcription suppressor, RNA polymerase inhibitor, RNA decomposing enzyme, protein synthesis inhibitor, nuclear translocation inhibitor, protein decomposing enzyme, protein denaturant and the like; to minimize the adverse effects on other genes and proteins expressed in the cells, it is important that the substance that suppresses the expression of target gene Y be capable of specifically acting on the target molecule.

An example of the substance that suppresses the expression of target gene Y is an antisense nucleic acid to a transcription product of target gene Y, specifically mRNA or initial transcription product. "An antisense nucleic acid" refers to a nucleic acid that consists of a base sequence capable of hybridizing to the target mRNA (initial transcription product) under physiological conditions for cells that express target mRNA (initial transcription product), and capable of inhibiting the translation of the polypeptide encoded by the target mRNA (initial transcription product) in a hybridized state. The kind of antisense nucleic acid may be DNA or RNA, or a DNA/RNA chimera. Because a natural type antisense nucleic acid easily undergoes degradation of the phosphoric acid diester bond thereof by a nucleic acid decomposing enzyme present in the cells, an antisense nucleic acid of the present invention can also be synthesized using a modified nucleotide of the thiophosphate type (P=O in phosphate linkage replaced with P=S), 2'-O-methyl type and the like which are stable to decomposing enzymes. Other important factors for the designing of antisense nucleic acid include increases in water-solubility and cell membrane permeability and the like; these can also be cleared by choosing appropriate dosage forms such as those using liposome or microspheres.

The length of antisense nucleic acid is not subject to limitation, as long as the antisense nucleic acid is capable of specifically hybridizing to the transcription product of target gene Y; the antisense nucleic acid may be of a sequence complementary to a sequence of about 15 bases for the shortest, or the entire sequence of the mRNA (initial transcription product) for the longest. Considering the ease of synthesis, antigenicity and other issues, for example, oligonucleotides consisting of about 15 bases or more, preferably about 15 to about 30 bases, can be mentioned.

The target sequence for the antisense nucleic acid may be any sequence that inhibits the translation of target gene Y or a functional fragment thereof by being hybridized to the antisense nucleic acid, and may be the entire sequence or a partial sequence of mRNA, or the intron moiety of the initial transcription product; when an oligonucleotide is used as the antisense nucleic acid, it is desirable that the target sequence be located between the 5' terminus of the mRNA of target gene Y and the C terminus of the coding region thereof.

Furthermore, the antisense nucleic acid may be not only capable of hybridizing to a transcription product of target gene Y to inhibit its translation, but also binding to target gene Y in the form of double-stranded DNA to form a triple-strand (triplex) and inhibit the transcription to mRNA.

Another example of the substance that suppresses the expression of target gene Y is a ribozyme capable of specifically cleaving a transcription product of target gene Y, specifically mRNA or initial transcription product in the coding region (including the intron portion in the case of initial transcription product). "A ribozyme" refers to an RNA possessing enzyme activity to cleave nucleic acids. Because it has recently been shown that an oligo-DNA having the base sequence of the enzyme activity site also possesses nucleic acid cleavage activity, this term is herein used to mean a concept including DNA, as long as sequence specific nucleic acid cleavage activity is possessed. The most versatile ribozyme is self-splicing RNA, found in infectious RNAs such as those of viroid and virosoid; this self-splicing RNA is known to occur in some types, including hammerhead type and hairpin type. When ribozyme is used in the form of an expression vector comprising a DNA that encodes the same, a hybrid ribozyme wherein a sequence modified from tRNA is further linked to promote localization to cytoplasm may be used [Nucleic Acids Res., 29(13): 2780-2788 (2001)].

A still another example of the substance that suppresses the expression of target gene Y is a decoy nucleic acid. A decoy nucleic acid refers to a nucleic acid molecule that mimics a region to which a transcription regulatory factor binds; the decoy nucleic acid, which is the substance that suppresses the expression of target gene Y, can be a nucleic acid molecule that mimics a region to which a transcription activation factor for target gene Y binds.

Examples of the decoy nucleic acid include oligonucleotides modified to make them unlikely to undergo degradation in a body, such as oligonucleotides having a thiophosphoric diester bond wherein an oxygen atom in the phosphoric diester bond moiety is replaced with a sulfur atom (S-oligo), and oligonucleotides wherein the phosphoric diester bond is replaced with an uncharged methyl phosphate group, and the like. Although the decoy nucleic acid may completely match with the region to which a transcription activation factor binds, the degree of matching may be such that the transcription activation factor for target gene Y is retained. The length of the decoy nucleic acid is not subject to limitation, as long as the transcription activation factor binds thereto. The decoy nucleic acid may comprise a repeat of the same region.

Still another example of the substance that suppresses the expression of target gene Y is a double-stranded oligo-RNA, i.e. siRNA, which is complementary to a partial sequence (including the intron portion in the case of an initial transcription product) in the coding region of a transcription product of target gene Y, specifically, the mRNA or initial transcription product. It has been known that so-called RNA interference (RNAi), which is a phenomenon that if short double stranded RNA is introduced into cells, mRNA complementary to the RNA is degraded, occurs in nematodes, insects, plants and the like; recently, it has been found that this phenomenon also occurs in animal cells [Nature, 411(6836): 494-498 (2001)], which is drawing attention as an alternative technique to ribozymes. The siRNA used may be internally synthesized as described below, and a commercially available one may be used.

An antisense oligonucleotide and ribozyme can be prepared by determining the target sequence for a transcription product of target gene Y, specifically the mRNA or initial transcription product on the basis of the cDNA sequence or genomic DNA sequence of target gene Y, and by synthesizing a sequence complementary thereto using a commercially available automated DNA/RNA synthesizer (Applied Biosystems Company, Beckman Instruments Company and the like). A decoy nucleic acid and siRNA can be prepared by synthesizing a sense strand and an antisense strand in an automated DNA/RNA synthesizer, respectively, denaturing the chains in an appropriate annealing buffer solution at about 90 to about 95° C. for about 1 minute, and then annealing the chains at about 30 to about 70° C. for about 1 to about 8 hours. A longer double-stranded polynucleotide can be prepared by synthesizing a complementary oligonucleotide chain in alternative overlaps, annealing them, and then ligating them with ligase.

Another example of the substance that suppresses the expression of target gene Y is an antibody against target protein Y. The antibody may be a polyclonal antibody or a monoclonal antibody, and can be prepared by a well-known immunological technique. The antibody may also be a fragment of an antibody (e.g., Fab, F(ab')$_2$), or a recombinant antibody (e.g., single-chain antibody). Furthermore, the nucleic acid that encodes the antibody (one functionally linked to a nucleic acid having promoter activity) is also preferable as the substance that suppresses the expression of target gene Y.

The polyclonal antibody can be acquired by, for example, subcutaneously or intraperitoneally administering target protein Y or a fragment thereof (as required, may be prepared as a complex crosslinked to a carrier protein such as bovine serum albumin or KLH (keyhole limpet hemocyanin)) as the antigen, along with a commercially available adjuvant (e.g., Freund's complete or incomplete adjuvant) to an animal about 2 to 4 times at intervals of 2 to 3 weeks (the antibody titer of partially drawn serum has been determined by a known antigen-antibody reaction and its elevation has been confirmed in advance), collecting whole blood about 3 to about 10 days after final immunization, and purifying the antiserum. As the animal to receive the antigen, mammals such as rats, mice, rabbits, goat, guinea pigs, and hamsters can be mentioned.

The monoclonal antibody can be prepared by a cell fusion method (e.g., Takeshi Watanabe, Saibou Yugouhou No Genri To Monokuronaru Koutai No Sakusei, edited by Akira Taniuchi and Toshitada Takahashi, "Monokuronaru Koutai To Gan-Kiso To Rinsho-", pages 2-14, Science Forum Shuppan, 1985). For example, the factor is administered subcutaneously or intraperitoneally along with a commercially available adjuvant to a mouse 2 to 4 times, and about 3 days after final administration, the spleen or lymph nodes are collected, and leukocytes are collected. These leukocytes and myeloma cells (e.g., NS-1, P3X63Ag8 and the like) are cell-fused to obtain a hybridoma that produces a monoclonal antibody against the factor. This cell fusion may be performed by the PEG method [J. Immunol. Methods, 81(2): 223-228 (1985)], or by the voltage pulse method [Hybridoma, 7(6): 627-633 (1988)]. A hybridoma that produces the desired monoclonal antibody can be selected by detecting an antibody that binds specifically to the antigen from the culture supernatant using a widely known EIA or RIA method and the like. Cultivation of the hybridoma that produces the monoclonal antibody can be performed in vitro, or in vivo such as in mouse or rat ascitic fluid, preferably in mouse ascitic fluid, and the antibody can be acquired from the culture supernatant of the hybridoma and the ascitic fluid of the animal, respectively.

However, in view of therapeutic efficacy and safety in humans, the antibody of the present invention may be a chimeric antibody or a humanized or human type antibody. The chimeric antibody can be prepared with reference to, for example, "Jikken Igaku (extra issue), Vol. 6, No. 10, 1988", Japanese Patent Kokoku Publication No. HEI-3-73280 and the like. The humanized antibody can be prepared with reference to, for example, Japanese Patent Kohyo Publication No. HEI-4-506458, Japanese Patent Kokai Publication No. SHO-62-296890 and the like. The human antibody can be prepared with reference to, for example, "Nature Genetics, Vol. 15, p. 146-156, 1997", "Nature Genetics, Vol. 7, p. 13-21, 1994", Japanese Patent Kohyo Publication No. HEI-4-504365, International Patent Application Publication No. WO94/25585, "Nikkei Science, June issue, pp. 40 to 50, 1995", "Nature, Vol. 368, pp. 856-859, 1994", Japanese Patent Kohyo Publication No. HEI-6-500233 and the like.

The substance that regulates the expression or function of target gene Y can also be a substance that suppresses a function of target gene Y.

Although the substance that suppresses a function of target gene Y is not subject to limitation, as long as it is capable of interfering with an action of target gene Y, it is important that the substance be capable of specifically acting on the target molecule to minimize the adverse effect on other genes and proteins. Examples of the substance that specifically suppresses a function of target gene Y include a dominant negative mutant of target protein Y and a nucleic acid that encodes the mutant (one functionally linked to a nucleic acid having promoter activity).

A dominant negative mutant of target protein Y refers to a mutant having the activity thereof reduced as a result of mutagenesis to target protein Y. The dominant negative mutant can have the activity thereof indirectly inhibited by competing with natural target protein Y. The dominant negative mutant can be prepared by introducing a mutation to a nucleic acid that encodes target gene Y. Examples of the mutation include amino acid mutations in a functional domain that result in a decrease in the function responsible for the domain (e.g., deletion, substitution, and addition of one or more amino acids). The mutation can be introduced by a method known per se using PCR or a commonly known kit.

Provided that the substance that suppresses the expression of target gene Y is a nucleic acid molecule, the regulator of the present invention can have an expression vector that encodes the nucleic acid molecule as the active ingredient thereof. The expression vector is an oligonucleotide or polynucleotide that encodes the above-described nucleic acid molecule, and must be functionally linked to a promoter capable of exhibiting promoter activity in the cells of the recipient mammal. Any promoter capable of functioning in the recipient mammal can be used; examples include viral promoters such as the SV40-derived early promoter, cytomegalovirus LTR, Rous sarcoma virus LTR, MoMuLV-derived LTR, and adenovirus-derived early promoter, and mammalian structural protein gene promoters such as the β-actin gene promoter, PGK gene promoter, and transferrin gene promoter, and the like.

The expression vector preferably comprises a transcription termination signal, that is, a terminator region, downstream of the oligo (poly)nucleotide that encodes the nucleic acid molecule. The expression vector may further comprise a selection marker gene for selecting transformant cells (genes that confer resistance to drugs such as tetracycline, ampicillin, kanamycin, hygromycin, and phosphinothricin, genes that compensate for auxotrophic mutation, and the like).

Although the basic backbone vector used as the expression vector is not subject to limitation, vectors suitable for administration to mammals such as humans include viral vectors such as retrovirus, adenovirus, adeno-associated virus, herpesvirus, vaccinia virus, poxvirus, poliovirus, Sindbis virus, and Sendai virus. Adenovirus has advantageous features, including the very high efficiency of gene introduction and possibility of introduction to non-dividing cells. Because incorporation of the introduced gene to host chromosome is very rare, however, gene expression is transient, usually lasting for about 4 weeks. In view of the sustainability of therapeutic effect, it is also preferable to use adeno-associated virus, which offers relatively high gene transduction efficiency, which can be introduced to non-dividing cells, and which can be incorporated in chromosomes via a inverted terminal repeat sequence (ITR).

The substance that regulates the expression or function of target protein Y can also be cefaclor, ubenimex, aclarubicin, cefadroxil, ursolic acid, dicloxacillin, ketanserin, ampicillin, or a derivative thereof capable of binding to target protein Y (described below), or a salt thereof.

Regulator I, in addition to a substance that regulates the expression or function of target gene Y, can comprise any carrier, for example, a pharmaceutically acceptable carrier.

Examples of the pharmaceutically acceptable carrier include, but are not limited to, excipients such as sucrose, starch, mannitol, sorbitol, lactose, glucose, cellulose, talc, calcium phosphate, and calcium carbonate; binders such as cellulose, methylcellulose, hydroxypropylcellulose, polypropylpyrrolidone, gelatin, gum arabic, polyethylene glycol, sucrose, and starch; disintegrants such as starch, carboxymethylcellulose, hydroxypropylstarch, sodium-glycolstarch, sodium hydrogen carbonate, calcium phosphate, and calcium citrate; lubricants such as magnesium stearate, Aerosil, talc, and sodium lauryl sulfate; flavoring agents such as citric acid, menthol, glycyrrhizin ammonium salt, glycine, and orange powder; preservatives such as sodium benzoate, sodium hydrogen sulfite, methyl paraben, and propyl paraben; stabilizers such as citric acid, sodium citrate, and acetic acid; suspending agents such as methylcellulose, polyvinylpyrrolidone, and aluminum stearate; dispersing agents such as surfactants; diluents such as water, physiological saline, and orange juice; base waxes such as cacao fat, polyethylene glycol, and kerosene, and the like.

Preparations suitable for oral administration include liquids comprising an effective amount of substance dissolved in a diluent such as water, physiological saline, or orange juice, capsules, sachets or tablets comprising an effective amount of substance in the form of solid or granules, suspensions comprising an effective amount of substance suspended in an appropriate dispersant, emulsions comprising a solution of an effective amount of substance dispersed in an appropriate dispersant and the like.

Preparations suitable for parenteral administration (e.g., subcutaneous injection, intramuscular injection, topical injection, intraperitoneal injection, and the like) include aqueous and non-aqueous isotonic sterile injection liquids, which may comprise an antioxidant, a buffer solution, a bacteriostatic agent, an isotonizing agent and the like. Other examples are aqueous and non-aqueous sterile suspensions, which may comprise a suspending agent, a solubilizer, a thickening agent, a stabilizer, an antiseptic and the like. The preparation can be included in a container in a unit dose or multiple doses like an ampoule or vial. It is also possible to lyophilize the active ingredient and a pharmaceutically acceptable carrier and preserve them in a state that only requires dissolving or suspending in a suitable sterile vehicle immediately before use.

The dose of regulator I varies depending on the activity and kind of the active ingredient, severity of the disease, the animal species to be the administration subject, drug acceptability, body weight and age of the administration subject, and the like, it is generally about 0.001 to about 500 mg/kg a day for an adult based on the amount of the active ingredient.

Regulator I enables the regulation, for example, suppression or promotion, of an action associated with bioactive substance X. Hence, regulator I is useful for the prophylaxis and treatment of a disease or condition associated with bioactive substance X, and as an investigational reagent for the disease or the condition, and the like.

3.2. Regulator of Function Associated with Target Gene Y (Regulator II)

The present invention provides a regulator of a function associated with target gene Y, which comprises bioactive substance X.

This regulator is referred to as "regulator II" as required.

Bioactive substance X can be cefaclor, ubenimex, aclarubicin, cefadroxil, ursolic acid, dicloxacillin, ketanserin, ampicillin, or a derivative thereof capable of binding to target protein Y (described below), or a salt thereof.

Regulator II can comprise, in addition to bioactive substance X, any carrier, for example, a pharmaceutically acceptable carrier. The dose of regulator II is the same as that of regulator I.

Regulator II enables the regulation, for example, suppression or promotion, of a function associated with target gene Y. Hence, regulator II is useful for the prophylaxis and treatment of a disease or condition associated with target gene Y, and as an investigational reagent for the disease, and the like.

4. Derivative Production Methods and Products Obtained by the Method

The present invention provides production methods for derivatives of bioactive substances, each of which comprises derivatizing a bioactive substance so that the expression or function of a target gene can be regulated, and products obtained by the method. From the viewpoint of the kind of action or function of the derivative obtained by the production method, the production methods of the present invention can be roughly divided into production methods for derivatives of bioactive substance X capable of regulating an action associated with bioactive substance X, and production methods for derivatives of bioactive substance X capable of regulating a function associated with target gene Y. The individual production methods are hereinafter described in detail.

4.1. Production Method for Derivative of Bioactive Substance X Capable of Regulating Action Associated with Bioactive Substance X (Production Method I)

The present invention provides a production method for a derivative of bioactive substance X capable of regulating an action associated with bioactive substance X, which comprises derivatizing bioactive substance X so that the expression or function of target gene Y can be regulated.

This production method is referred to as "production method I" as required.

This production method is referred to as "production method I" as required.

Derivatization means that a compound obtained by replacing a particular atom or group in a lead compound with another atom or group, or a compound obtained by subjecting a lead compound to an addition reaction, is virtually or actually synthesized.

The derivatization of bioactive substance X can be performed so that the regulatory capability for the expression or function of target gene Y is retained, and as required, in view of other properties of the derivative obtained, such as hydrophilicity/liphophilicity, stability, dynamics, bioavailability, toxicity and the like. The derivatization of bioactive substance X can be performed so that, for example, the regulatory capability for the expression or function of target gene Y can be increased. The derivatization of bioactive substance X can also be performed so that a function associated with target gene Y can be regulated.

The derivatization of bioactive substance X such that the regulatory capability for the expression or function of target gene Y is retained can be performed on the basis of, for example, SBDD (structure-based drug design) and CADD (computer-aided drug design). Examples of the design include virtual screening, de novo design, pharmacophore analysis, QSAR (quantitative structure activity relationship) and the like. If information on the steric structure of the protein itself or the target site of the protein is required during such designing, information on the steric structure is used provided that the steric structure is known by a structural analytical technique such as NMR, X-ray crystallographic analysis, or synchrotron radiation analysis. If the steric structure is unknown, information obtained by a structural predictive method such as the homology method or the threading method is used. In virtual screening, a program known per se is used; examples of the program include DOCK (Kuntz, I. D. et al., Science, 1992, 257, 1078), Gold (Jones, G. et al., J. Mol. Biol., 1995, 245, 43), FlexX (Rarey, M. et al., J. Mol. Biol., 1996, 261, 470), AutoDock (Morris, G. M. et al., J. Comput. Chem., 1998, 19, 1639), ICM (Abagyan, R. A. et al., J. Comput. Chem., 1994, 15, 488) and the like.

The derivatization of bioactive substance X such that the regulatory capacity for the expression or function of target gene Y is retained can also be performed on the basis of, for example, biological verification. In this case, for example, the above-described methodologies I to III can be used. Furthermore, one of the above-described methods such as SBDD and CADD, and biological verification may be used in combination.

The particular atom in bioactive substance X (a lead compound), which is substituted for producing the derivative, may be any atom present in the lead compound, exemplified by a hydrogen atom, a halogen atom (e.g., fluorine atom, chlorine atom, bromine atom, iodine atom), an oxygen atom, a sulfur atom, a nitrogen atom, a carbon atom and the like.

The particular group in bioactive substance X, which is substituted for producing the derivative, may be any group present in bioactive substance X, and can, for example, be a group having a molecular weight of 1 to 500, preferably 1 to 300, more preferably 1 to 200, most preferably 1 to 100. Examples of the particular group include an optionally substituted $C_1$ to $C_8$ hydrocarbon group, an optionally substituted $C_1$ to $C_8$ acyl group, an optionally substituted aromatic or non-aromatic $C_3$ to $C_{14}$ hydrocarbon cyclic group, or an optionally substituted aromatic or non-aromatic $C_3$ to $C_{14}$ heterocyclic group, an amino group, an amino group mono- or di-substituted by an alkyl group having 1 to 4 carbon atoms or an acyl group having 2 to 8 carbon atoms, an amidino group, a carbamoyl group, a carbamoyl group mono- or di-substituted by an alkyl group having 1 to 4 carbon atoms, a sulfamoyl group, a sulfamoyl group mono- or di-substituted by an alkyl group having 1 to 4 carbon atoms, a carboxyl group, an alkoxycarbonyl group having 2 to 8 carbon atoms, a hydroxy group, an alkoxy group having 1 to 6 carbon atoms optionally substituted by 1 to 3 halogen atoms, an alkenyloxy group having 2 to 5 carbon atoms optionally substituted by 1 to 3 halogen atoms, a cycloalkyloxy group having 3 to 7 carbon atoms, an aralkyloxy group having 7 to 9 carbon atoms, an aryloxy group having 6 to 14 carbon atoms, a thiol group, an alkylthio group having 1 to 6 carbon atoms optionally substituted by 1 to 3 halogen atoms, an aralkylthio group having 7 to 9 carbon atoms, an arylthio group having 6 to 14 carbon atoms, a sulfo group, a cyano group, an azido group, a nitro group, a nitroso group and the like.

The optionally substituted $C_1$ to $C_8$ hydrocarbon group can, for example, be an optionally substituted $C_1$ to $C_8$ alkyl group, an optionally substituted $C_2$ to $C_8$ alkenyl group, or an optionally substituted $C_2$ to $C_8$ alkynyl group.

The $C_1$ to $C_8$ alkyl group in the optionally substituted $C_1$ to $C_8$ alkyl group may be linear or branched, preferably having 1 to 6 carbon atoms; examples include methyl, ethyl, propyl, isopropyl, butyl, isobutyl, sec-butyl, tert-butyl and the like.

The $C_2$ to $C_8$ alkenyl group in the optionally substituted $C_2$ to $C_8$ alkenyl group may be linear or branched, preferably having 2 to 6 carbon atoms; examples include ethenyl, 1-propenyl, 2-propenyl, 2-methyl-1-propenyl, 1-butenyl, 2-butenyl, 3-butenyl and the like.

The $C_2$ to $C_8$ alkinyl group in the optionally substituted $C_2$ to $C_8$ alkinyl group may be linear or branched, preferably having 2 to 6 carbon atoms; examples include ethynyl, 1-propynyl, 2-propynyl, 1-buthynyl, 2-buthynyl, 3-buthynyl and the like.

The $C_1$ to $C_8$ acyl group in the optionally substituted $C_1$ to $C_8$ acyl group may be linear or branched, preferably having 2 to 6 carbon atoms; examples include formyl, acetyl, propinoyl, butanoyl, 2-methylpropinoyl and the like.

The aromatic $C_3$ to $C_{14}$ hydrocarbon cyclic group in the optionally substituted aromatic $C_3$ to $C_{14}$ hydrocarbon cyclic group may be monocyclic, bicyclic or tricyclic, preferably having 3 to 12 carbon atoms; examples include phenyl and naphthyl.

The non-aromatic $C_3$ to $C_{14}$ hydrocarbon cyclic group in the optionally substituted non-aromatic $C_3$ to $C_{14}$ hydrocarbon cyclic group may be saturated or unsaturated monocyclic, bicyclic or tricyclic, preferably having 3 to 12 carbon atoms; examples include cycloalkyl groups (e.g., cyclopropyl, cyclobutyl, cyclopentyl, cyclohexyl, cycloheptyl, cyclooctyl), cycloalkenyl groups (e.g., 2-cyclopenten-1-yl, 3-cyclopenten-1-yl, 2-cyclohexen-1-yl, 3-cyclohexen-1-yl), cycloalkadienyl groups (e.g., 2,4-cyclopentadien-1-yl, 2,4-cyclohexadien-1-yl, 2,5-cyclohexadien-1-yl) and the like.

The aromatic $C_3$ to $C_{14}$ heterocyclic group in the optionally substituted aromatic $C_3$ to $C_{14}$ heterocyclic group is a monocyclic, bicyclic or tricyclic aromatic heterocyclic group containing 1 to 5 hetero atoms selected from among oxygen atoms, sulfur atoms and nitrogen atoms, in addition to carbon atoms, as the ring-forming atoms, preferably having 3 to 12 carbon atoms. Examples of the monocyclic aromatic $C_3$ to $C_{14}$ heterocyclic group include furyl, thienyl, pyrrolyl, oxazolyl, isooxazolyl, thiazolyl, isothiazolyl, imidazolyl, pyrazolyl, oxadiazolyl, furazanyl, thiadiazolyl, triazolyl, tetrazolyl, pyridyl, pyrimidinyl, pyridazinyl, pyrazinyl, triazinyl and the like. Examples of the bicyclic or tricyclic aromatic heterocyclic group include benzofuranyl, isobenzofuranyl, benzo[b]thienyl, indolyl, isoindolyl, 1H-indazolyl, benzimidazolyl, benzooxazolyl, benzothiazolyl, 1H-benzotriazolyl, quinolyl, isoquinolyl, cinnolyl, quinazolyl, quinoxalinyl, phthaladinyl, naphthylizinyl, purinyl, pteridinyl, carbazolyl, α-carbonylyl, β-carbonylyl, γ-carbonylyl, acrydinyl, phenoxazinyl, phenothiazinyl, phenadinyl, phenoxathiinyl, thianthrenyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

The non-aromatic $C_3$ to $C_{14}$ heterocyclic group in the optionally substituted non-aromatic $C_3$ to $C_{14}$ heterocyclic group is a monocyclic, bicyclic or tricyclic saturated or unsaturated heterocyclic group containing 1 to 5 hetero atoms selected from among oxygen atoms, sulfur atoms and nitrogen atoms, in addition to carbon atoms, as the ring-forming atoms, preferably having 3 to 12 carbon atoms; examples include oxiranyl, azetidinyl, oxetanyl, thietanyl, pyrrolidinyl, tetrahydrofuryl, tetrahydropyranyl, morpholinyl, thiomorpholinyl, piperazinyl, pyrrolidinyl, piperidino, morpholino, thiomorpholino and the like.

The kind of the substituent in any group optionally substituted can be the same as the particular group in bioactive substance X (described above), which is substituted for producing the derivative.

The number of particular atoms or groups in bioactive substance X, which is substituted for producing the derivative is any one, as long as the derivative produced is capable of regulating the expression or function of the gene Y, for example, as long as it is capable of binding to target protein Y, and can be, for example, 1 to 10, preferably 1 to 5, more preferably 1 to 3, further more preferably 1 to 2, most preferably 1.

The kind of a particular atom or group used for substitution (i.e., an atom or group introduced to the substitution site) can be the same as the particular atom or group in bioactive substance X, which is substituted for producing the derivative.

The atom or group added to bioactive substance X for producing the derivative (i.e., an atom or group used in the addition reaction) is an atom permitting an addition reaction, for example, an atom such as the hydrogen atom or the halogen atom, or a group capable of acting as a nucleophile or electrophile, out of the particular atoms or groups in bioactive substance (described above), which is substituted for producing the derivative.

The number of atoms or groups added to bioactive substance X for producing the derivative is any one, as long as the derivative produced is capable of regulating the expression or function of the gene Y, for example, as long as it is capable of binding to target protein Y, and can be, for example, less than 6, preferably less than 4, more preferably less than 2.

The production method I is useful for, for example, the development of prophylactic or therapeutic agents for diseases or conditions associated with bioactive substance X or investigational reagents for the diseases or the conditions, and the like.

4.2. Production Method for Derivative of Bioactive Substance X Capable of Regulating Function Associated with Target Gene Y (Production Method II)

The present invention provides a production method for a derivative of bioactive substance X capable of regulating a function associated with target gene Y, which comprises derivatizing bioactive substance X so that the bindability thereof to target protein Y or a mutant protein thereof capable of binding to bioactive substance X can be regulated.

This production method is referred to as "production method II" as required.

Derivatization of bioactive substance X can be performed so that the bindability thereof to target protein Y or a mutant protein thereof capable of binding to bioactive substance X is retained, and as required, in view of other properties of the derivative obtained, such as water solubility/oil solubility, stability, disposition, bioavailability, toxicity and the like. Derivatization of bioactive substance X can be performed so that, for example, the binding ability can be increased.

Derivatization of bioactive substance X such that the bindability is retained can be performed on the basis of, for example, SBDD and CADD.

Derivatization of bioactive substance X such that the bindability is retained can also be performed on the basis of, for example, biological verification. In this case, for example, derivatization can be performed in the same manner as the above-described methodology III. Furthermore, one of the above-described methods such as SBDD and CADD, and biological verification may be used in combination.

The choice of a particular atom and group in the lead compound substituted for producing a derivative, and their numbers, can be the same as those described above. The particular atom or group used for the substitution (i.e., atom or group introduced to the substitution site), the atom or group added to bioactive substance X for producing a derivative (i.e., atom or group used for the addition reaction), and their numbers are also the same as those described above.

Production method II is useful for the development of prophylactic/therapeutic agents for diseases or conditions associated with target gene Y, or investigational reagents for the diseases or the conditions, and the like.

4.3. Products Obtained by Derivative Production Method

The present invention provides a product obtained by the above-described methods I, II.

The product provided by the above-described production method can be bioactive substance X derivative obtained by the production method of the present invention, and a bioactivity regulator comprising the derivative (described above).

A product provided by the above-described production method is useful for, for example, the prophylaxis or treatment of a disease or condition associated with bioactive substance X, or a disease or condition associated with target gene Y, or as investigational reagents for the disease or the condition, and the like.

5. Complex and Method of Producing the Same

The present invention provides a complex comprising a bioactive substance and a target protein therefor.

The bioactive substance can be, for example, the above-described bioactive substance X. Specifically, bioactive substance X can be cefaclor, ubenimex, aclarubicin, cefadroxil, ursolic acid, dicloxacillin, ketanserin, and ampicillin, or a derivative thereof capable of binding to target protein Y. The kind of bioactive substance X can be selected as appropriate according to the kind of target protein Y.

The target protein for a bioactive substance can be, for example, the above-described target protein Y. Specifically, target protein Y can be a protein consisting of the amino acid sequence shown by SEQ ID NO:2, SEQ ID NO:4, SEQ ID NO:6, SEQ ID NO:8, SEQ ID NO:10, SEQ ID NO:12, SEQ ID NO:14, SEQ ID NO:16 or SEQ ID NO:18, or a mutant protein thereof capable of binding to the bioactive substance. The mutant protein is as described above. The kind of target protein Y used to form the complex can be chosen as appropriate according to the kind of bioactive substance X.

In one mode of embodiment, the complex of the present invention can be a complex according to a combination of cefaclor, ubenimex, aclarubicin, cefadroxil, ursolic acid, dicloxacillin, ketanserin or ampicillin, or a derivative thereof capable of binding to a target protein, and the target protein.

In another embodiment, the complex of the present invention can be a complex according to a combination of a protein consisting of the amino acid sequence shown by SEQ ID NO:2, SEQ ID NO:4, SEQ ID NO:6, SEQ ID NO:8, SEQ ID NO:10, SEQ ID NO:12, SEQ ID NO:14, SEQ ID NO:16 or SEQ ID NO:18, or a mutant protein thereof capable of binding to the bioactive substance, and a bioactive substance capable of binding to the protein.

Preferably, the complex of the present invention can be a complex according to any of the following combinations (1) to (8):

(1) a combination of cefaclor and a gene corresponding to a protein consisting of the amino acid sequence shown by SEQ ID NO:2, SEQ ID NO:6, SEQ ID NO:8 or SEQ ID NO:12;
(2) a combination of ubenimex and a gene corresponding to a protein consisting of the amino acid sequence shown by SEQ ID NO:2;
(3) a combination of aclarubicin and a gene corresponding to a protein consisting of the amino acid sequence shown by SEQ ID NO:4;
(4) a combination of cefadroxil and a gene corresponding to a protein consisting of the amino acid sequence shown by SEQ ID NO:6;
(5) a combination of ursolic acid and a gene corresponding to a protein consisting of the amino acid sequence shown by SEQ ID NO:10;
(6) a combination of dicloxacillin and a gene corresponding to a protein consisting of the amino acid sequence shown by SEQ ID NO:14;
(7) a combination of ketanserin and a gene corresponding to a protein consisting of the amino acid sequence shown by SEQ ID NO:16;
(8) a combination of ampicillin and a protein consisting of the amino acid sequence shown by SEQ ID NO:18.

The present invention also provides a method of producing a complex comprising a bioactive substance and a target protein therefor, which comprises bringing the bioactive substance and the target protein therefor into contact with each other. This contact can be performed by, for example, mixing the bioactive substance and the target protein in solution.

The complex of the present invention and the production method for the complex can be useful for, for example, performing the screening methods of the present invention and the derivative production methods of the present invention, or in cases where a complex is structurally analyzed to extensively investigate the mode of interaction between a bioactive substance and a target protein therefor, and the like.

6. Kit

The present invention provides a kit comprising a bioactive substance or a salt thereof.

In one embodiment, the kit of the present invention comprises the following (i) and (ii):
(i) a bioactive substance or a salt thereof;
(ii) a target protein for a bioactive substance, a nucleic acid that encodes the protein, an expression vector comprising the nucleic acid, cells enabling a measurement of the expression of a target gene for the bioactive substance, or an expression vector comprising the transcription regulatory region of a target gene for the bioactive substance and a reporter gene functionally linked to the region.

Provided that the kit of the present invention comprises a target protein for a bioactive substance, the protein is not in the form of a complex with the bioactive substance.

The bioactive substance, the target protein and target gene therefor, and the combination of bioactive substance and target protein therefor are the same as those described above (see, e.g., "5. Complex, and a method of producing the same"). The expression vector, the cells enabling a measurement of the expression of a target gene for a bioactive substance, the transcription regulatory region of the target gene for the bioactive substance, and the reporter gene functionally linked to the region, are the same as those described above (see, e.g., "2. Screening method, and product obtained by the method").

The above-described kit of the present invention can be useful in, for example, performing the screening methods of the present invention, the derivative production method of the present invention, and the complex production method of the present invention and the like.

7. Determination Methods and Determination Kits for Onset or Risk of Onset of Disease or Condition The present invention provides determination methods and determination kits for the onset or risk of onset of a specified disease or condition. From the aspect of the subjects to be measured, the determination methods and determination kits of the present invention can be roughly divided into determination methods and determination kits based on measurement of the expression level, and determination methods and determination kits based on identification of the polymorphism. Furthermore, they can be classified into determination methods and determination kits for the onset or risk of onset of a disease or condition associated with bioactive substance X, and determination methods and determination kits for the onset or risk of onset of a disease or condition associated with target gene Y, from the viewpoint of the disease or condition for which a determination of the onset or risk of onset is desired. The individual determination methods and determination kits are hereinafter described in detail.

7.1. Determination Methods and Determination Kits for Onset or Risk of Onset of Disease or Condition on the Basis of Measurement of Expression Level of Target Gene Y 7.1.1. Determination Method for Onset or Risk of Onset of Disease or Condition Associated with Bioactive Substance X on the Basis of Measurement of Expression Level of Target Gene Y (Determination Method I)

The present invention provides a determination method for the onset or risk of onset of a disease or condition associated with bioactive substance X, which comprises measuring the expression level of target gene Y.

This determination method is referred to as "determination method I" as required.

In one embodiment, determination method I comprises the following steps (a) and (b):
(a) a step for measuring the expression level of target gene Y in a biological sample collected from an animal;
(b) a step for evaluating the onset or likelihood of onset of a disease or condition associated with bioactive substance X on the basis of the expression level of target gene Y.

The methodology comprising the above-described steps (a) and (b) is referred to as "methodology V" as required.

In step (a) of methodology V, the expression level of target gene Y in a biological sample collected from an animal is measured. While the animal is not particularly limited, mammal including laboratory animals such as mice, rats, hamsters, guinea pigs, rabbits etc., domestic animals such as swine, bovine, goat, horses, sheep etc., companion animals such as dogs, cats etc., and primates such as monkeys, orangutans, chimpanzees, humans etc.

The biological sample may be any sample containing a tissue expressing target gene Y. The tissue expressing target gene Y can be examined using, for example, H-Inv DB.

The expression level of target gene Y can be measured by a method known per se with a product, for example, a transcription product or translation product, of target gene Y, as the subject.

In step (b) of methodology V, a determination is made whether or not the animal is suffering from a disease or condition associated with bioactive substance X on the basis of the expression level of target gene Y. Specifically, first, the measured expression level of target gene Y is compared with the expression level of target gene Y in an animal that has not contracted the disease or condition associated with bioactive substance X (e.g., a normal animal). This comparison of expression level is preferably performed on the basis of the presence or absence of a significant difference. The expression level of target gene Y in an animal that has not contracted the disease or condition associated with bioactive substance X can be determined by a method known per se.

Next, on the basis of the result of the comparison of the expression level of target gene Y, a judgment is made whether or not the animal is possibly suffering from a disease or condition associated with bioactive substance X, or is likely or unlikely to suffer from the same in the future. The combination of a disease or condition associated with bioactive substance X and target gene Y is the same as described above. It is known that in animals that have contracted a particular disease, a change in the expression of the gene associated with the disease is often observed. It is also known that prior to the onset of a particular disease, a change in the expression of the particular gene is often observed. Hence, by analyzing the expression level of target gene Y, it is possible to determine the onset or likelihood of onset of the disease or condition associated with bioactive substance X.

Determination method I enables a determination of the presence or absence of a disease or condition associated with bioactive substance X, or the likelihood of contracting the disease or condition. Hence, determination method I is useful for, for example, the easy and early detection of the disease or condition and the like.

7.1.2. Determination Kit for Onset or Risk of Onset of Disease or Condition Associated with Bioactive Substance X on the Basis of Measurement of Expression Level of Target Gene Y (Determination Kit I)

The present invention provides a determination kit that enables the easy conduct of determination method I.

This determination kit is referred to as "determination kit I" as required.

In one embodiment, determination kit I comprises the following (i) and (ii):
(i) a means capable of measuring the expression level of target gene Y;
(ii) a medium recording the relationship between a disease or condition associated with bioactive substance X and the expression level of target gene Y.

The means capable of measuring the expression level of target gene Y is not subject to limitation, as long as it allows a quantitation of the expression level of target gene Y; for example, such means are roughly divided into means capable of quantifying target protein Y (e.g., antibody, bioactive substance X), and means capable of quantifying a transcript of target gene Y (e.g., nucleic acid probe, a pair of primers). The means may be labeled with a labeling substance. Provided that the means is not labeled with a labeling substance, the determination kit of the present invention may further comprise the labeling substance. The labeling substance is the same as described above.

Determination kit I enables a determination of the presence or absence of a disease or condition associated with bioactive substance X, or the likelihood of contracting the disease or condition. Hence, determination kit I is useful for, for example, the easy and early detection of the disease or condition and the like.

7.2. Determination Methods and Determination Kits for Risk of Onset of Disease or Condition on the Basis of Identification of Polymorphism of Target Gene Y 7.2.1. Determination Method for Risk of Onset of Disease or Condition Associated with Bioactive Substance X on the Basis of Identification of Polymorphism of Target Gene Y (Determination Method II)

The present invention provides a determination method for the risk of onset of a disease or condition associated with bioactive substance X, which comprises identifying the polymorphism of target gene Y.

This determination method is referred to as "determination method II" as required.

In one embodiment, determination method II comprises the following steps (a) and (b):
(a) a step for identifying the polymorphism of target gene Y in a biological sample collected from an animal;
(b) a step for evaluating the likelihood of the onset of a disease or condition associated with bioactive substance X on the basis of the type of polymorphism.

The methodology comprising the above-described steps (a) and (b) is referred to as "methodology VI" as required.

In step (a) of methodology VI, the type of polymorphism of target gene Y in a biological sample collected from an animal is identified. The animal is the same as described above.

Although the biological sample used may be one described with respect to methodology V above, this methodology VI enables the use of any tissue containing genomic DNA such as hair, nails, skin or mucosa as the biological sample. In view of the ease of procurement, burden on the human body and the like, the biological sample is preferably a sample of hair, nails, skin, mucosa, blood, plasma, serum, saliva and the like.

A polymorphism of target gene Y means a mutation found at a frequency in the nucleotide sequence of the genomic DNA comprising target gene Y in a certain population, and can be one or more DNA substitutions, deletions, or additions (e.g., SNP, haplotype) in the genomic DNA comprising target gene Y, and a repeat, inversion, translocation and the like of the genomic DNA. Various types of polymorphism of target gene Y are registered with known databases, for example, H-Inv DB and the like. The type of polymorphism of target gene Y used in this determination method is a mutation in a nucleotide sequence whose frequency differs between animals suffering from a disease or condition associated with bioactive substance X and non-suffering animals out of all types of polymorphism in target gene Y, and can be, for example, one that alters the expression of target gene Y or alters a function associated with target gene Y (e.g., the ability of target protein Y to bind to bioactive substance X). Such types of polymorphism can be determined by a method known per se such as linkage analysis.

A determination of the type of polymorphism can be performed by a method known per se. For example, the RFLP (restriction fragment length polymorphism) method, the PCR-SSCP (single-stranded DNA conformation polymorphism) analysis method, the ASO (allele specific oligonucleotide) hybridization method, the TaqMan PCR method, the invader method and the like can be used.

In step (b) of methodology VI, a determination of the likelihood of contracting a disease or condition associated with bioactive substance X in an animal is made on the basis of the type of polymorphism. The combination of a disease or condition associated with bioactive substance X and target gene Y is the same as described above. It is known that animals susceptible to a particular disease often have a particular type of polymorphism in the gene associated with the disease. Hence, it is possible to determine the likelihood of the onset of a disease or condition associated with bioactive substance X by polymorphism analysis.

Determination method II enables a determination of the likelihood of contracting a disease or condition associated with bioactive substance X. Hence, determination method II is useful for the provision of an incentive for improving one's lifestyle for the purpose of preventing the disease or condition and the like.

7.2.2. Determination Kit for Risk of Onset of Disease or Condition Associated with Bioactive Substance X on the Basis of Identification of Polymorphism of Target Gene Y (Determination Kit II)

The present invention also provides a determination kit that enables the easy conduct of determination method II.

This determination kit is referred to as "determination kit II" as required.

In one embodiment, determination kit II comprises the following (i) and (ii):
(i) a means capable of identifying the polymorphism of target gene Y (e.g., nucleic acid probe, a pair of primers);
(ii) a medium recording the relationship between a disease or condition relating to bioactive substance X and polymorphism of target gene Y.

Determination kit II enables a determination of the likelihood of contracting a disease or condition associated with bioactive substance X. Hence, determination kit II is useful for the provision of an incentive for improving one's lifestyle for the purpose of preventing the disease or condition and the like.

7.2.3. Method of Determining Risk of Onset of Disease or Condition Associated with Target Gene Y on the Basis of Identification of Polymorphism of Target Gene Y (Determination Method III)

The present invention provides a determination method for the risk of onset of a disease or condition associated with target gene Y, which comprises identifying the polymorphism of target gene Y.

This determination method is referred to as "determination method III" as required.

In one embodiment, determination method III comprises the following steps (a) and (b):
(a) a step for determining the type of the polymorphism of target gene Y in a biological sample collected from an animal;
(b) a step for evaluating the likelihood of the onset of a disease or condition associated with target gene Y on the basis of the type of polymorphism.

In determination method III, the type of polymorphism used to determine the risk of onset alters the ability of target protein Y to bind to bioactive substance X. The type of polymorphism can be determined by a method known per se such as binding assay.

The methodology comprising steps (a) and (b) above in determination method III is the same as methodology VI except for the type of polymorphism of target gene Y to be identified.

Determination method III enables a determination of the likelihood of contracting a disease or condition associated with target gene Y. Hence, determination method III is useful for the provision of an incentive for improving one's lifestyle for the purpose of preventing the disease or condition and the like.

7.2.4. Determination Kit for Risk of Onset of Disease or Condition Associated with Target Gene Y on the Basis of Identification of Polymorphism of Target Gene Y (Determination Kit III)

The present invention also provides a determination kit that enables the easy conduct of determination method III.

This determination kit is referred to as "determination kit III" as required.

In one embodiment, determination kit III comprises the following (i) and (ii):
(i) a means capable of identifying the polymorphism of target gene Y;
(ii) a medium recording the relationship between a disease or condition associated with target gene Y and the polymorphism of target gene Y.

In determination kit III, the type of polymorphism used to determine the risk of onset is one that alters the ability of target protein Y to bind to bioactive substance X. The type of polymorphism can be determined by a method known per se such as binding assay.

The constituents of determination kit III are the same as those of determination kit II except for the type of polymorphism of target gene Y to be identified.

Determination kit III enables a determination of the likelihood of contracting a disease or condition associated with target gene Y. Hence, determination kit III is useful for the provision of an incentive for improving one's lifestyle for the purpose of preventing the disease or condition and the like.

8. Determination Methods and Determination Kits for Susceptibility to Bioactive Substances The present invention provides determination methods and determination kits for susceptibility to a bioactive substance. The determination methods and determination kits of the present invention can be roughly divided into determination methods and determination kits based on measurement of expression level, and determination methods and determination kits based on identification of polymorphism. Furthermore, they are classified into determination methods and determination kits for a disease or condition associated with bioactive substance X, and determination methods and determination kits for a disease or condition associated with target gene Y, from the viewpoint of a disease or condition for which a determination of susceptibility is desired. The individual determination methods and determination kits are hereinafter described in detail.

8.1. Determination Methods and Determination Kits for Susceptibility to Bioactive Substances on the Basis of Measurement of Expression Level of Target Gene Y

8.1.1. Determination Method for Susceptibility to Bioactive Substance X in Disease or Condition Associated with Bioactive Substance X on the Basis of Measurement of Expression Level of Target Gene Y (Determination Method IV)

The present invention provides a determination method for susceptibility to bioactive substance X in a disease or condition associated with bioactive substance X, which comprises measuring the expression level of target gene Y.

This determination method is referred to as "determination method IV" as required.

In one embodiment, determination method IV comprises the following steps (a) and (b):
(a) a step for measuring the expression level of target gene Y in a biological sample collected from an animal;
(b) a step for predicting the effect of bioactive substance X on the basis of the expression level of target gene Y.

The methodology comprising the above-described steps (a) to (b) is referred to as "methodology VII" as required.

Step (a) of methodology VII is the same as step (a) of methodology IV.

In step (b) of methodology VII, the possible effect of bioactive substance X on animals is evaluated on the basis of the expression level of target gene Y. Specifically, first, the measured expression level of target gene Y is checked against data on the correlation of the expression level of target gene Y and susceptibility to bioactive substance X. The correlation between the expression level of target gene Y and susceptibility to bioactive substance X can be determined by a method known per se.

Next, from the result of the comparison, susceptibility to bioactive substance X is estimated. The combination of bioactive substance X and target gene Y are the same as described above. It is considered that in animals expressing a target gene for a bioactive substance at high levels, their susceptibility to the bioactive substance is high (or low), and that in animals expressing the same at low levels, their susceptibility is low (or high). Hence, it is possible to determine the susceptibility of an animal to bioactive substance X by analyzing the expression level of target gene Y. For example, provided that bioactive substance X is a drug, the likelihood or unlikelihood of obtainment of desired effect of the drug, or the probability of onset of adverse effect of a drug, can be determined.

Determination method IV enables a determination of susceptibility to bioactive substance X. Hence, determination method IV is useful for, for example, the evaluation of an action of bioactive substance X on a particular animal, and the like.

8.1.2. Determination Kit for Susceptibility to Bioactive Substance X in Disease or Condition Associated with Bioactive Substance X on the Basis of Measurement of Expression Level of Target Gene Y (Determination Kit IV)

The present invention provides a determination kit that enables the easy conduct of determination method IV.

This determination kit is referred to as "determination kit IV" as required.

In one embodiment, determination kit IV comprises the following (i) and (ii):
(i) a means capable of measuring the expression level of target gene Y;
(ii) a medium recording the relationship between the effect of bioactive substance X and the expression level of target gene Y.

The constituents of determination kit IV are the same as those of determination kit I except medium (ii).

Determination kit IV enables the easy determination of susceptibility to bioactive substance X. Hence, determination kit IV is useful for, for example, the evaluation of an action of bioactive substance X on a particular animal and the like.

8.2. Determination Methods and Determination Kits for Susceptibility to Bioactive Substance X on the Basis of Identification of Polymorphism of Target Gene Y

8.2.1. Determination Method for Susceptibility to Bioactive Substance X in Disease or Condition Associated with Bioactive Substance X on the Basis of Identification of Polymorphism of Target Gene Y (Determination Method V)

The present invention provides a determination method for susceptibility to bioactive substance X in a disease or condition associated with bioactive substance X, which comprises identifying the polymorphism of target gene Y.

This determination method is referred to as "determination method V" as required.

In one embodiment, determination method V comprises the following steps (a) and (b):
(a) a step for identifying the polymorphism of target gene Y in a biological sample collected from an animal;
(b) a step for predicting the effect of bioactive substance X in a disease or condition associated with target gene Y on the basis of the presence or absence of a particular type of polymorphism.

The methodology comprising the above-described steps (a) to (b) is referred to as "methodology VIII" as required.

Step (a) of methodology VIII is the same as step (a) of methodology VII.

In step (b) of methodology VIII, the effect of bioactive substance X in a disease or condition associated with bioactive substance X is evaluated on the basis of the type of polymorphism of target gene Y. Specifically, first, the identified type of polymorphism of target gene Y is checked against data on the correlation of the type of polymorphism of target gene Y and susceptibility to bioactive substance X in a disease or condition associated with bioactive substance X. This correlation can be determined by a method known per se.

Next, from the result of the comparison, susceptibility to bioactive substance X in a disease or condition associated with bioactive substance X is estimated. The combination of bioactive substance X and target gene Y are the same as described above. It is known that in animals that are highly susceptible to a bioactive substance, a particular type of polymorphism is often observed in a target gene for the bioactive substance. Hence, it is possible to determine the susceptibility of an animal to bioactive substance X by analyzing polymorphism. For example, provided that bioactive substance X is a drug, the likelihood or unlikelihood of obtainment of desired effect of the drug, or the probability of onset of adverse reaction of a drug, can be determined.

Determination method V enables the easy determination of susceptibility to bioactive substance X in a disease or condition associated with bioactive substance X. Hence, determination method V is useful for, for example, the evaluation of an action of bioactive substance X in a disease or condition associated with bioactive substance X and the like.

8.2.2. Determination Kit for Susceptibility to Bioactive Substance X in Disease or Condition Associated with Bioactive Substance X on the Basis of Identification of Polymorphism of Target Gene Y (Determination Kit V)

The present invention also provides a determination kit that enables the easy conduct of determination method V.

This determination kit is referred to as "determination kit V" as required.

In one embodiment, determination kit V comprises the following (i) and (ii):
(i) a means capable of identifying the polymorphism of target gene Y;
(ii) a medium recording the relationship between the effect of bioactive substance X and the polymorphism of gene Y.

The constituents of determination kit V are the same as those of determination kit II except medium (ii).

Determination kit V enables a determination of susceptibility to bioactive substance X in a disease or condition associated with bioactive substance X. Hence, determination kit V is useful for, for example, the evaluation of an action of bioactive substance X in a disease or condition associated with bioactive substance X and the like.

8.2.3. Determination Method for Susceptibility to Bioactive Substance X in Disease or Condition Associated with Target Gene Y on the Basis of Identification of Polymorphism of Target Gene Y (Determination Method VI)

The present invention provides a determination method for susceptibility to bioactive substance X in a disease or condition associated with target gene Y, which comprises identifying the polymorphism of target gene Y.

This determination method is referred to as "determination method VI" as required.

In one embodiment, determination method VI comprises the following steps (a) and (b):
(a) a step for determining the type of polymorphism of target gene Y in a biological sample collected from an animal;
(b) a step for predicting the effect of bioactive substance X in a disease or condition associated with target gene Y on the basis of the presence or absence of a particular type of polymorphism.

In this determination method, the type of polymorphism used to determine the susceptibility is one that alters the ability of target protein Y to bind to bioactive substance X. The type of polymorphism can be determined by a method known per se such as binding assay. Animals having a target gene comprising the type of polymorphism that potentiates or reduces the binding ability to the bioactive substance are thought to be highly (or poorly) susceptible to the bioactive substance; animals having a target gene comprising a type of polymorphism that reduces the binding ability are considered to be less (or more) susceptible. Hence, the susceptibility of an animal to bioactive substance X can be determined by analyzing the type of polymorphism.

The methodology comprising steps (a) and (b) above in determination method VI is the same as methodology VIII except for the type of polymorphism of target gene Y to be identified.

Determination method VI enables the easy determination of susceptibility to bioactive substance X in a disease or condition associated with bioactive substance X. Hence, determination method VI is useful for, for example, the evaluation of an action of bioactive substance X in a disease or condition associated with bioactive substance X and the like.

8.2.4. Determination Kit for Susceptibility to Bioactive Substance X in Disease or Condition Associated with Target Gene Y on the Basis of Identification of Polymorphism of Target Gene Y (Determination Kit VI)

The present invention also provides a determination kit that enables the easy conduct of determination method VI.

This determination kit is referred to as "determination kit VI" as required.

In one embodiment, determination kit VI comprises the following (i) and (ii):
(i) a means capable of identifying the polymorphism of target gene Y;
(ii) a medium recording the relationship between a disease or condition associated with target gene Y and the polymorphism of target gene Y.

In determination kit VI, the type of polymorphism used to determine the risk of onset is one that alters the ability of target protein Y to bind to bioactive substance X. The type of polymorphism can be determined by a method known per se such as binding assay.

The constituents of determination kit VI are the same as those of determination kit V except for the type of polymorphism of target gene Y to be identified.

Determination kit VI enables a determination of susceptibility to bioactive substance X in a disease or condition associated with bioactive substance X. Hence, determination kit VI is useful for, for example, the evaluation of an action of bioactive substance X in a disease or condition associated with bioactive substance X and the like.

The disclosures in all publications mentioned herein, including patents and patent application specifications, are incorporated by reference herein to the extent that all of them have been given expressly.

The present invention is hereinafter described in more detail by means of the following examples, which, however, are not to be construed as limiting the present invention.

EXAMPLES

The present invention is hereinafter described in more detail by means of the following examples, which, however, are not to be construed as limiting the present invention.

Reference Example 1

Method of Expressing Protein from Human Full-Length cDNA Clone

1. Preparation of Expression Plasmid

A desired gene of a human full-length cDNA clone was BP-reacted with the PCR cloning vector Gateway pDONR201 using the Invitrogen Gateway system per the kit protocol to yield an entry vector. As the destination vector for the Gateway system, a Gateway cassette having a Gateway recombinant sequence was introduced to allow the utilization of the Gateway system on the basis of pEU3-NII (Toyobo), which matches with a cell-free protein synthesis system (PROTEIOS) of Toyobo Co., Ltd., which employs a wheat germ extract, and a double tag destination vector modified using the PCR method to allow the expression of a peptide having a histidine tag and a FLAG tag sequence in the N-terminal region of the expressed protein was prepared.

The prepared double tag destination vector and entry vector were BP-reacted using the Invitrogen Gateway system per the protocol and the *Escherichia coli* competent cell DH5α was transformed therewith; a clone incorporating the expression vector was selected. A plasmid was prepared from the obtained clone using the QIAfilter Midi kit (QUIAGEN) per the kit protocol. The plasmid obtained was subjected to phenol/chloroform treatment per the protocol for PROTEIOS (Toyobo) to inactivate the RNase to yield a purified expression plasmid.

2. Acquisition of Purified Protein

A recombinant protein was synthesized using a cell-free protein synthesis system (PROTEIOS) of Toyobo Co., Ltd., which employs a wheat germ extract. Subsequently, mRNA was prepared from the expression plasmid acquired by the method described in section 1 above per the protocol for PROTEIOS. With 20 μg of the mRNA acquired, a protein was synthesized per the protocol for PROTEIOS using two wells of a 96-well microtiter plate. The protein synthesized was subjected to high-speed centrifugation, the precipitate was removed, and the resulting soluble fraction was purified using ANTI-FLAG M2 Affinity Gel (SIGMA Company) having an anti-FLAG tag antibody immobilized hereto per the protocol, to yield a purified protein.

Reference Example 2

Determination of Binding Dissociation Constant for Human Protein-Drug Interactions Using Biacore The surface of the CM5 sensor chip for S51 commercially available from Biacore Company was subjected to an NTA treatment with 1 M EDC, 1.33 M NHS and 16 mg/ml AB-NTA (pH 9.2) to prepare an NTA sensor chip for S51. A protein expressed in a wheat germ system, and purified using a FLAG tag, was immobilized to the chip. This immobilization was achieved by sequentially injecting 0.5 M $NiCl_2$, 0.4 M EDC, 0.1 M EDC, ligand solution (protein), and 1 M ethanolamine, pH 8.5, into the flow system of Biacore S51. The running buffer used in the immobilization was PBS (pH 7.4). The assay described below was performed using the ligand-immobilized sensor chip. The running buffer used was prepared by adding DMSO at a final concentration of 5% to a mixture of HBS (10 mM HEPES, 150 mM NaCl, pH 7.6), 0.005% $P_2O$, and 100 μM mineral ion cocktail ($Ca(OAc)_2$, $Zn(OAc)_2.2H_2O$, $Cu(OAc)_2.H_2O$, $Co(OAc)_2.4H_2O$, $Mn(OAc)_2.4H_2O$, $Mg(OAc)_2.4H_2O$, $FeCl_3.6H_2O$). A series of solutions of the analyte compound were prepared by two-fold dilution at 9 points from 62.5 μM to 0.244 μM. Separately, a blank liquid consisting of the solvent alone (no analyte compound contained) was prepared for a 0-concentration determination with the same solvent composition as that for the running buffer. A correction for the effect of DMSO contained in the compound solutions and running buffer (solvent correction) was performed on the basis of measured results from separately prepared solutions mimicking the running buffer, and containing 3.8 to 5.1% of DMSO (8 points). The compound characterization assay program for Biacore S51 was performed to measure the interactions between immobilized ligands (proteins) and analytes (compounds; 62.5 μM to 0.244 μM), and the results were analyzed using a dedicated software program.

Example 1

Analysis of Interaction Between FLJ10335-Derived Protein and Cefaclor

A protein was expressed and purified from FLJ10335 according to the method of Reference Example 1, and the interaction between cefaclor and the protein expressed and purified from FLJ10335 was analyzed according to the method of Reference Example 2. As a result, the binding level increased proportionally to the dose of cefaclor, with the binding saturated at high doses; cefaclor was confirmed to interact specifically with the FLJ10335-derived protein. Using a dedicated software program for Biacore S51, the binding dissociation constant was calculated to be Kd=$5.493 \times 10^{-6}$ M.

Thus, it was found that cefaclor and the FLJ10335-derived protein interacted with each other. Hence, the FLJ10335-derived protein was found to be a target protein for cefaclor. Therefore, a new drug can be screened by reacting screening candidate substances and the FLJ10335-derived protein. Specifically, a new drug can be screened by, for example, constructing a system which detects the interaction between the FLJ10335-derived protein and a candidate substance according to the method of Reference Example 2.

Example 2

Analysis of Interaction Between FLJ10335-Derived Protein and Ubenimex

A protein was expressed and purified from FLJ10335 according to the method of Reference Example 1, and the interaction between the protein expressed and purified from FLJ10335 and Ubenimex was analyzed according to the method of Reference Example 2. As a result, the binding level increased proportionally to the dose of ubenimex, with the binding saturated at high doses; ubenimex was confirmed to interact specifically with the FLJ10335-derived protein. Using a dedicated software program for Biacore S51, the binding dissociation constant was calculated to be Kd=$6.430 \times 10^{-6}$ M.

From the above, it was found that Ubenimex and a protein derived from FLJ10335 interact with each other. Hence, the FLJ10335-derived protein was found to be a target protein for Ubenimex. Therefore, a new drug can be screened by reacting screening candidate substances and the FLJ10335-derived protein. Specifically, a new drug can be screened by, for example, constructing a system which detects the interaction between the FLJ10335-derived protein and a candidate substance according to the method of Reference Example 2.

Example 3

Analysis of Interaction Between FLJ10889-Derived Protein and Aclarubicin

A protein was expressed and purified from FLJ10889 according to the method of Reference Example 1, and the interaction between aclarubicin and the protein expressed and purified from FLJ10889 was analyzed according to the method of Reference Example 2. As a result, the binding level increased proportionally to the dose of aclarubicin, with the binding saturated at high doses; aclarubicin was confirmed to interact specifically with the FLJ10889-derived protein. Using a dedicated software program for Biacore S51, the binding dissociation constant was calculated to be Kd=$1.641 \times 10^{-6}$ M.

Thus, it was found that aclarubicin and the FLJ10889-derived protein interacted with each other. Hence, the FLJ10889-derived protein was found to be a target protein for aclarubicin. This demonstrates the possibility of screening for a new drug by reacting the FLJ10889-derived protein and a screening candidate substance. Hence, new drug screening can be performed by constructing a system that comprises detecting the interaction between the FLJ10889-derived protein and a candidate substance by, for example, the method of Reference Example 2.

Example 4

Analysis of Interaction Between FLJ11045-Derived Protein and Cefaclor

A protein was expressed and purified from FLJ11045 according to the method of Reference Example 1, and the interaction between cefaclor and the protein expressed and purified from FLJ11045 was analyzed according to the method of Reference Example 2. As a result, the binding level increased proportionally to the dose of cefaclor, with the binding saturated at high doses; cefaclor was confirmed to interact specifically with the FLJ11045-derived protein. Using a dedicated software program for Biacore S51, the binding dissociation constant was calculated to be Kd=$1.244 \times 10^{-5}$ M.

Thus, it was found that cefaclor and the FLJ11045-derived protein interacted with each other. Hence, the FLJ11045-derived protein was found to be a target protein for cefaclor. This demonstrates the possibility of screening for a new drug by reacting the FLJ11045-derived protein and a screening candidate substance. Hence, new drug screening can be performed by constructing a system that comprises detecting the interaction between the FLJ11045-derived protein and a candidate substance by, for example, the method of Reference Example 2.

Example 5

Analysis of Interaction Between FLJ11045-Derived Protein and Cefadroxil

A protein was expressed and purified from FLJ11045 according to the method of Reference Example 1, and the interaction between cefadroxil and the protein expressed and purified from FLJ11045 was analyzed according to the method of Reference Example 2. As a result, the binding level increased proportionally to the dose of cefadroxil, with the binding saturated at high doses; cefadroxil was confirmed to interact specifically with the FLJ11045-derived protein. Using a dedicated software program for Biacore S51, the binding dissociation constant was calculated to be Kd=$1.153 \times 10^{-5}$ M.

Thus, it was found that cefadroxil and the FLJ11045-derived protein interacted with each other. Hence, the FLJ11045-derived protein was found to be a target protein for cefadroxil. This demonstrates the possibility of screening for a new drug by reacting the FLJ11045-derived protein and a screening candidate substance. Hence, new drug screening can be performed by constructing a system that comprises detecting the interaction between the FLJ11045-derived protein and a candidate substance by, for example, the method of Reference Example 2.

Example 6

Analysis of Interaction Between FLJ11474-Derived Protein and Cefaclor

A protein was expressed and purified from FLJ11474 according to the method of Reference Example 1, and the interaction between cefaclor and the protein expressed and purified from FLJ11474 was analyzed according to the method of Reference Example 2. As a result, the binding level increased proportionally to the dose of cefaclor, with the binding saturated at high doses; cefaclor was confirmed to interact specifically with the FLJ11474-derived protein. Using a dedicated software program for Biacore S51, the binding dissociation constant was calculated to be Kd=$7.554 \times 10^{-6}$ M.

Thus, it was found that cefaclor and the FLJ11474-derived protein interacted with each other. Hence, the FLJ11474-derived protein was found to be a target protein for cefaclor. This demonstrates the possibility of screening for a new drug by reacting the FLJ11474-derived protein and a screening candidate substance. Hence, new drug screening can be performed by constructing a system that comprises detecting the interaction between the FLJ11474-derived protein and a candidate substance by, for example, the method of Reference Example 2.

Example 7

Analysis of Interaction Between FLJ12502-Derived Protein and Ursolic Acid

A protein was expressed and purified from FLJ12502 according to the method of Reference Example 1, and the interaction between ursolic acid and the protein expressed and purified from FLJ12502 was analyzed according to the method of Reference Example 2. As a result, the binding level increased proportionally to the dose of ursolic acid, with the binding saturated at high doses; ursolic acid was confirmed to interact specifically with the FLJ12502-derived protein. Using a dedicated software program for Biacore S51, the binding dissociation constant was calculated to be Kd=$8.101 \times 10^{-6}$ M.

Thus, it was found that ursolic acid and the FLJ12502-derived protein interacted with each other. Hence, the FLJ12502-derived protein was found to be a target protein for ursolic acid. Therefore, a new drug can be screened by reacting the FLJ12502-derived protein and screening candidate substances. Specifically, a new drug can be screened by, for example, constructing a system which detects the interaction between the FLJ12502-derived protein and a candidate substance according to the method of Reference Example 2.

Example 8

Analysis of Interaction Between FLJ14467-Derived Protein and Cefaclor

A protein was expressed and purified from FLJ14467 according to the method of Reference Example 1, and the interaction between cefaclor and the protein expressed and purified from FLJ14467 was analyzed according to the method of Reference Example 2. As a result, the binding level increased proportionally to the dose of cefaclor, with the binding saturated at high doses; cefaclor was confirmed to interact specifically with the FLJ14467-derived protein. Using a dedicated software program for Biacore S51, the binding dissociation constant was calculated to be Kd=4.005×10$^{-6}$ M.

Thus, it was found that cefaclor and the FLJ14467-derived protein interacted with each other. Hence, the FLJ14467-derived protein was found to be a target protein for cefaclor. Therefore, a new drug can be screened by reacting the FLJ14467-derived protein and screening candidate substances. Specifically, a new drug can be screened by, for example, constructing a system which detects the interaction between the FLJ14467-derived protein and a candidate substance according to the method of Reference Example 2.

Example 9

Analysis of Interaction Between FLJ14583-Derived Protein and Dicloxacillin

A protein was expressed and purified from FLJ14583 according to the method of Reference Example 1, and the interaction between dicloxacillin and the protein expressed and purified from FLJ14583 was analyzed according to the method of Reference Example 2. As a result, the binding level increased proportionally to the dose of dicloxacillin, with the binding saturated at high doses; dicloxacillin was confirmed to interact specifically with the FLJ14583-derived protein. Using a dedicated software program for Biacore S51, the binding dissociation constant was calculated to be Kd=2.300×10$^{-5}$ M.

From the above, it was found that dicloxacillin and a protein derived from FLJ14583 interact with each other. Hence, the FLJ14583-derived protein was found to be a target protein for dicloxacillin. Therefore, a new drug can be screened by reacting the FLJ14583-derived protein and screening candidate substances. Specifically, a new drug can be screened by, for example, constructing a system which detects the interaction between the FLJ14583-derived protein and a candidate substance according to the method of Reference Example 2.

Example 10

Analysis of Interaction Between FLJ14797-Derived Protein and Ketanserin

A protein was expressed and purified from FLJ14797 according to the method of Reference Example 1, and the interaction between ketanserin and the protein expressed and purified from FLJ14797 was analyzed according to the method of Reference Example 2. As a result, the binding level increased proportionally to the dose of ketanserin, with the binding saturated at high doses; ketanserin was confirmed to interact specifically with the FLJ14797-derived protein. Using a dedicated software program for Biacore S51, the binding dissociation constant was calculated to be Kd=5.941×10$^{-6}$ M.

Thus, it was found that ketanserin and the FLJ14797-derived protein interacted with each other. Hence, the FLJ14797-derived protein was found to be a target protein for ketanserin. Therefore, a new drug can be screened by reacting the FLJ14797-derived protein and screening candidate substances. Specifically, a new drug can be screened by, for example, constructing a system which detects the interaction between the FLJ14797-derived protein and a candidate substance according to the method of Reference Example 2.

Example 11

Analysis of Interaction Between FLJ31146-Derived Protein and Ampicillin

A protein was expressed and purified from FLJ31146 according to the method of Reference Example 1, and the interaction between ampicillin and the protein expressed and purified from FLJ31146 was analyzed according to the method of Reference Example 2. As a result, the binding level increased proportionally to the dose of ampicillin, with the binding saturated at high doses; ampicillin was confirmed to interact specifically with the FLJ31146-derived protein. Using a dedicated software program for Biacore S51, the binding dissociation constant was calculated to be Kd=8.207×10$^{-6}$ M.

Thus, it was found that ampicillin and the FLJ31146-derived protein interacted with each other. Hence, the FLJ31146-derived protein was found to be a target protein for ampicillin. This demonstrates the possibility of screening for a new drug by reacting the FLJ31146-derived protein and a screening candidate substance. Hence, new drug screening can be performed by constructing a system that comprises detecting the interaction between the FLJ31146-derived protein and a candidate substance by, for example, the method of Reference Example 2.

Data on binding strength (Kd value) concerning the specific interactions between drugs and proteins observed in the Examples above are shown in Table 8.

TABLE 8

| FLJ No. | Drug to be bound with | Kd value |
|---------|----------------------|----------|
| FLJ10335 | cefaclor | 5.493 × 10$^{-5}$ M |
|  | ubenimex | 6.430 × 10$^{-5}$ M |
| FLJ10889 | aclarubicin | 1.641 × 10$^{-5}$ M |
| FLJ11045 | cefaclor | 1.244 × 10$^{-5}$ M |
|  | cefadroxil | 1.153 × 10$^{-5}$ M |
| FLJ11474 | cefaclor | 7.554 × 10$^{-5}$ M |
| FLJ12502 | ursolic acid | 8.101 × 10$^{-5}$ M |
| FLJ14467 | cefaclor | 4.005 × 10$^{-5}$ M |
| FLJ14583 | dicloxacillin | 2.300 × 10$^{-5}$ M |
| FLJ14797 | ketanserin | 5.941 × 10$^{-5}$ M |
| FLJ31146 | ampicillin | 8.207 × 10$^{-5}$ M |

According to a most recent report of Rothstein et al. (Nature, (2005), 433, 73-77), when 1,040 kinds of pharmaceutical products and nutritional foods approved by FDA were screened with an increased expression of glutamic acid transporter GLT1 as an index, 15 compounds of β lactam antibiotics were found. It was confirmed that the GLT1 transport ability was enhanced by β lactam antibiotic and showed a suppressive action on the neuronal cell death due to glutamic acid toxicity. Moreover, when a β lactam antibiotic, ceftriaxone, was intraperitoneally administered to a mutant SOD-transgenic mouse showing ALS-like symptoms, expression of GLT1 in the spinal cord increased, and recovery of neuron number and increase in the muscle strength were observed. Based thereon, the neuroprotective action of β lactam antibiotics is drawing attention, and clinical trials of ALS have been started (Science, (2005), 307, 361-362).

The interactive pairs of this application include 4 kinds of β lactam antibiotics (Ampicillin, Cefaclor, Cefadroxil, Dicloxacillin). In the present application, since these compounds were found to specifically bind with human proteins, the drug target protein of the present application is considered to be involved in the neuroprotective action of β lactam antibiotics. Moreover, annotation analysis clearly revealed that, of the proteins with which β lactam antibiotics were bound, FLJ10335 and FLJ31146 are proteins having a ubiquitin-related domain, and FLJ11474 is a protein having a G protein-like structure. Therefrom it is considered that the neuroprotective action of β lactam antibiotics is derived from a proteolysis system via ubiquitin or intracellular signal transduction via G protein.

INDUSTRIAL APPLICABILITY

The target proteins and target genes of the present invention enable the development of bioactive substances, for example, drug discovery and the like. The screening methods of the present invention and the derivative production method of the present invention enable the development of prophylactic or therapeutic agents for various diseases or conditions, and investigational reagents for the diseases or the conditions, and the like. The regulators and derivatives of the present invention enable the prophylaxis and treatment of various diseases or conditions, and the development of investigational reagents for the diseases or the conditions, and the like. The complexes and kits of the present invention enable the implementation of the screening methods of the present invention, the derivative production methods of the present invention and the like. The determination methods and determination kits of the present invention enable the evaluation of the onset or likelihood of onset of various diseases or conditions in animals, and the evaluation of the susceptibility of animals to bioactive substances and the like.

The target proteins and target genes of the present invention are useful for the development of bioactive substances, for example, drug discovery and the like. The screening methods of the present invention and the derivative production methods of the present invention are useful for the development of prophylactic or therapeutic agents for various diseases or conditions, and investigational reagents for the diseases or the conditions and the like. The regulators and derivatives of the present invention are useful for the prevention and treatment of various diseases or conditions, and as investigational reagents for the diseases or the conditions and the like. The complexes and kits of the present invention are useful for the screening methods of the present invention, the derivative production methods of the present invention and the like. The determination methods and determination kits of the present invention are useful for the evaluation of the onset or likelihood of onset of various diseases or conditions, evaluation of susceptibility to bioactive substances, and the like in animals.

This application is based on application No. 2004-325537 filed on Nov. 9, 2004 in Japan, the contents of which are incorporated hereinto by reference.

The invention claimed is:

1. A screening method for a substance that regulates a function associated with target protein Y, which method comprises the following steps (a) to (c):
   (a) a step for bringing a test substance and bioactive substance X into contact with target protein Y;
   (b) a step for measuring the binding level of bioactive substance X to the protein in the presence of the test substance, and comparing this binding level with the binding level of bioactive substance X to the protein in the absence of the test substance; and
   (c) a step for selecting a test substance that alters the binding level of bioactive substance X to the protein on the basis of the results of the comparison in step (b) above,
   wherein bioactive substance X is cefaclor and target protein Y is a protein containing the amino acid sequence of SEQ ID NO. 2.

2. A method of producing a derivative of bioactive substance X, which method comprises the derivatizing bioactive substance X so as to be able to regulate the function of target protein Y, wherein bioactive substance X is cefaclor and target protein Y is a protein containing the amino acid sequence of SEQ ID NO: 2.

3. A method of producing a derivative of a substance that regulates a function associated with target protein Y, which method comprises derivatizing bioactive substance X so that the bindability thereof to target protein Y can be regulated, wherein target protein Y is a protein containing the amino acid sequence shown by SEQ ID NO: 2 and bioactive substance X is cefaclor.

4. A kit comprising the following (i) and (ii):
   (i) bioactive substance X or a salt thereof;
   (ii) target protein Y, a nucleic acid that encodes the protein, an expression vector comprising the nucleic acid, cells that enable a measurement of the expression of the target protein Y, or an expression vector comprising the transcription regulatory region of a gene that encodes the target protein Y and a reporter gene functionally linked thereto,
   wherein the bioactive substance X is cefaclor and the target protein Y is a protein containing the amino acid sequence of SEQ ID NO: 2.

* * * * *

SEQUENCE LISTING

```
<160> NUMBER OF SEQ ID NOS: 18

<210> SEQ ID NO 1
<211> LENGTH: 1678
<212> TYPE: DNA
<213> ORGANISM: Homo sapiens

<400> SEQUENCE: 1
agagcttttc tgtgtttctc cggacttcga gccatggcgg tgacggaagc gagcctgttg      60
cgccagtgcc ccctgcttct gccccagaac cggtcgaaaa ccgtgtatga gggattcatc     120
tcggctcagg gaagagactt ccaccttagg atagtgttgc ctgaagattt acaactgaag     180
aatgcaagat tattatgtag ttggcagctg agaacaatac ttagtggata ccatcgaata     240
gtacaacaga gaatgcagca ccctcctgat ctaatgagct ttatgatgga gttgaagatg     300
cttttggaag ttgccttaaa gaatagacaa gagctgtatg cactacctcc tcctccccag     360
ttctactcaa gccttattga agagatagga actcttggtt gggataaact tgtgtatgcg     420
gatacctgct tcagtaccat caagttaaaa gcagaagatg cttctggtag agagcattta     480
atcactctca agttgaaggc aaagtatcct gcagaatcac cagattattt tgtggatttt     540
cctgttccat tttgtgcctc ctggacacct cagagctcct taataagcat ttatagtcag     600
tttttggcag caatagaatc actaaaggca ttctgggatt ttatggatga aatcgatgag     660
aagacctggg tacttgagcc agaaaaacct ccacggagtg caacagcacg cagaattgca     720
ttaggtaata atgtttccat aaatatagag gtagacccca ggcatcctac tatgcttcct     780
gagtgcttct ttcttggagc tgaccatgtg gtaaaacccc tgggaattaa gctgagcagg     840
aacatacatt tgtgggatcc agaaaatagt gtgttacaaa atttgaaaga tgttttagaa     900
attgattttc cagctcgtgc tatcctggaa aaatctgatt ttactatgga ttgtggaatt     960
tgttatgctt atcaacttga cggtaccatt cctgatcaag tgtgtgataa ttctcagtgt    1020
```

-continued

```
ggacaacctt tccatcaaat atgcttatat gagtggctga gaggactact aactagtaga    1080
cagagtttta acatcatatt tggtgaatgt ccatattgta gtaagccaat taccttaaaa    1140
atgtctggaa ggaaacactg aataagaat acaacatttc ggtgaagagc tggaaactta    1200
aaaaattatc aaaaggaatt ttggtatcat cttcagagaa aaaataaagc aagaaatact    1260
aacatcaaaa ggacaggtat gatgatgcga taataataaa catctgcgtt tgtctcttca    1320
ctaagagtaa actgggaaat gtaggccaa agtccagttg aactttctaa gtctgtgatc    1380
cccgtgctga ctgtggaagt gtatttatac caagatggag atcttgactt cttgaatata    1440
tctggactgg taaatcttg atgaggctca taaaatgagt ttgggaattg tgtatagctg    1500 atttttgtg ggaaactgtt tacttcattc aaaggttctt gagactcttg atatttctgt    1560
cttctccttg tgctttccta tggaaaaaat acatatatag tttagtttgt tagacgtgag    1620
ttatccaagt atttattttg tgtagtgtgt aagaatgcta aataaaatgt tatacaag     1678
```

<210> SEQ ID NO 2
<211> LENGTH: 375
<212> TYPE: PRT
<213> ORGANISM: Homo sapiens

<400> SEQUENCE: 2

```
Met Ala Val Thr Glu Ala Ser Leu Leu Arg Gln Cys Pro Leu Leu Leu
1               5                   10                  15

Pro Gln Asn Arg Ser Lys Thr Val Tyr Glu Gly Phe Ile Ser Ala Gln
            20                  25                  30

Gly Arg Asp Phe His Leu Arg Ile Val Leu Pro Glu Asp Leu Gln Leu
        35                  40                  45

Lys Asn Ala Arg Leu Leu Cys Ser Trp Gln Leu Arg Thr Ile Leu Ser
    50                  55                  60

Gly Tyr His Arg Ile Val Gln Gln Arg Met Gln His Pro Pro Asp Leu
65                  70                  75                  80

Met Ser Phe Met Met Glu Leu Lys Met Leu Leu Glu Val Ala Leu Lys
                85                  90                  95

Asn Arg Gln Glu Leu Tyr Ala Leu Pro Pro Pro Gln Phe Tyr Ser
            100                 105                 110

Ser Leu Ile Glu Glu Ile Gly Thr Leu Gly Trp Asp Lys Leu Val Tyr
        115                 120                 125

Ala Asp Thr Cys Phe Ser Thr Ile Lys Leu Lys Ala Glu Asp Ala Ser
    130                 135                 140

Gly Arg Glu His Leu Ile Thr Leu Lys Leu Lys Ala Lys Tyr Pro Ala
145                 150                 155                 160

Glu Ser Pro Asp Tyr Phe Val Asp Phe Pro Val Pro Phe Cys Ala Ser
                165                 170                 175

Trp Thr Pro Gln Ser Ser Leu Ile Ser Ile Tyr Ser Gln Phe Leu Ala
            180                 185                 190

Ala Ile Glu Ser Leu Lys Ala Phe Trp Asp Val Met Asp Glu Ile Asp
        195                 200                 205

Glu Lys Thr Trp Val Leu Glu Pro Glu Lys Pro Arg Ser Ala Thr
    210                 215                 220

Ala Arg Arg Ile Ala Leu Gly Asn Asn Val Ser Ile Asn Ile Glu Val
225                 230                 235                 240

Asp Pro Arg His Pro Thr Met Leu Pro Glu Cys Phe Phe Leu Gly Ala
                245                 250                 255

Asp His Val Val Lys Pro Leu Gly Ile Lys Leu Ser Arg Asn Ile His
            260                 265                 270
```

```
Leu Trp Asp Pro Glu Asn Ser Val Leu Gln Asn Leu Lys Asp Val Leu
        275                 280                 285

Glu Ile Asp Phe Pro Ala Arg Ala Ile Leu Glu Lys Ser Asp Phe Thr
        290                 295                 300

Met Asp Cys Gly Ile Cys Tyr Ala Tyr Gln Leu Asp Gly Thr Ile Pro
305                 310                 315                 320

Asp Gln Val Cys Asp Asn Ser Gln Cys Gly Gln Pro Phe His Gln Ile
                325                 330                 335

Cys Leu Tyr Glu Trp Leu Arg Gly Leu Leu Thr Ser Arg Gln Ser Phe
                340                 345                 350

Asn Ile Ile Phe Gly Glu Cys Pro Tyr Cys Ser Lys Pro Ile Thr Leu
            355                 360                 365

Lys Met Ser Gly Arg Lys His
        370                 375

<210> SEQ ID NO 3
<211> LENGTH: 3043
<212> TYPE: DNA
<213> ORGANISM: Homo sapiens

<400> SEQUENCE: 3
ggattttttc tgaaccagcc aggaaatacc ggaacccacc aaactttaaa caccagccta      60
aattattcct gttctttaa gcaggcagca gaaatgacag aaacccgtta acagaaaaaa     120
aaaaaataat gcttttcatt tgaactcctg tgcattttct ttttaactta tatgtgttcc     180
taattttcct tactcttttt gtttgtttgt ttcttagtgt ggtttattga caatcattta     240
caatgccgaa gagtgctgta gtgagccagc acagtgggta acacagcaac ggagaacaga     300
tgcaggtttg aggaatttaa cttgctaaaa ccttgaactg aagtcttaga gattggaaca     360
tacgggtttg tataaatagg cttttaagcc ctgtttgcaa tgggttactg ataggagaaa     420
cttgcttgtg aatgtcagc tgcgtgagct cactgtcaga caagatggaa gaagaagggc     480
tggagtgtcc aaactcttcc tctgaaaaac gctattttcc tgaatccctg gattccagcg     540
atggggatga ggaagaggtt ttggcctgtg aggatttgga acttaacccc tttgatggat     600
tgccatattc atcacgttat tataaacttc tgaaagaaag agaagatctt cctatatgga     660
aagaaaaata ctcctttatg gagaacctgc ttcaaaatca aatcgtgatt gtttcaggag     720
atgctaaatg tggtaagagc gctcaggttc ctcagtggtg tgctgaatat tgtcttttcca     780 tccactacca gcacgggggc gtgatatgca cacaggtcca caagcagact atggtccagc     840
tcgccctgcg ggtggcggat gaaatggatg ttaacattgg tcatgaggtt ggctacgtga     900
tccctttcga gaactgctgt accaacgaaa caatcctgag gtattgtact gatgatatgc     960
tgcaaagaga aatgatgtcc aatccttttt tgggtagcta tggggtcatc atcttagatg    1020
atattcatga aagaagcatt gcaaccgatg tgttacttgg acttcttaaa gatgttttac    1080
tagcaagacc agaactgaag ctcataatta actcctcacc tcacctgatc agcaaactca    1140
attcttatta tggaaacgtg cctgtcatag aagtgaaaaa taaacaccct gtggaggttg    1200
tgtaccttag tgaggctcaa aaggattctt ttgagtctat tttacgcctt atctttgaaa    1260
ttcaccactc gggtgagaaa ggtgacattg tagtctttct ggcctgtgaa caagatattg    1320
agaaagtctg tgaaactgtc tatcaaggat ctaacctaaa cccagatctt ggagaactgg    1380
tggttgttcc tttgtatcca aaagagaaat gttcattgtt caagccactc gatgaaacag    1440
aaaaaagatg ccaagtttat caagaagag tggtgttaac tactagctct ggagagtttt    1500
tgatctggag caactcagtc agatttgtta tcgatgtggg tgtggaaaga agaaaggtgt    1560
```

```
acaacccgag aataagagca aactcgctcg tcatgcagcc catcagccag agccaggcag    1620
agatacgcaa gcagattctt ggctcatctt cttcaggaaa attttctgc ctgtacactg    1680 aagaatttgc ctccaaagac atgacgccac tgaagccagc agaaatgcag gaagccaacc    1740
taacaagcat ggtgcttttt atgaagagga tagacattgc gggcctaggc cactgtgact    1800
tcatgaacag accagcacca gaaagtttga tgcaggcatc ggaagactta gattatctgg    1860
cagcactgga taatgatgga aatctttctg aatttggaat catcatgtca gagttttcctc   1920 ttgatccaca actctcgaag tctatcttag ggtcctgtga atttgactgt gtggatgaag    1980
tgctaacaat cgcggccatg gtaacagctc caaattgctt ttcacatgtg ccacatggag    2040
ctgaagaggc tgccttgact tgttggaaga catttttaca tcccgaagga gatcacttta    2100
ccctcatcag catttacaag gcttaccaag acacaactct gaattctagc agtgagtact    2160
gtgtggaaaa gtggtgtcgt gattacttcc tcaactgttc agcactcaga atggcagatg    2220
ttattcgagc tgaactctta gaaattatca agcgaatcga gcttccctat gcagaacctg    2280
cttttggctc caaggaaaac actctaaaca taaagaaagc tcttctgtcc ggttacttta    2340
tgcagattgc tcgggatgtt gatggatcag gtaactactt aatgctgaca cataagcagg    2400
ttgctcagct gcatccctg tctggttact caatcaccaa gaagatgcca gagtgggtcc     2460
tcttccataa attcagcatt tctgagaaca actacatcag gattacctca gaaatctctc    2520
ttgaactatt tatgcagctg gtaccacaat actatttcag taatctgcct cctagtgaaa    2580
gtaaggacat tctacagcaa gtagtggatc acctatcccc tgtgtcaaca atgaataagg    2640
aacagcaaat gtgtgagacg tgccctgaaa ctgaacagag atgcactctc cagtgactcc    2700
ccagcaaaca caaggtgcag cagggtccca aaggtagctg gatggctgaa ctgctggata    2760
tgggagatac atgacgcgaa gacggatttc acatccacag gacggtcttg aagaaaataa    2820
cactgtgtat attattttaa aataaaaaat agaagttttt attgagttct ttaaattacg    2880
actccatgct tttcttcttc ttggaaaagt ttttaaatca accactcata atttgaccaa    2940
aattttaaaa aactggtatt ttgtaaatgt gtcagagaca catgggacag aaccctactt    3000
tttgtagagg aacttaatct gaataaagtc tgagttttc agt                       3043
```

<210> SEQ ID NO 4
<211> LENGTH: 743
<212> TYPE: PRT
<213> ORGANISM: Homo sapiens

<400> SEQUENCE: 4

```
Met Glu Glu Glu Gly Leu Glu Cys Pro Asn Ser Ser Glu Lys Arg
1               5                   10                  15

Tyr Phe Pro Glu Ser Leu Asp Ser Ser Asp Gly Asp Glu Glu Val
                20                  25                  30

Leu Ala Cys Glu Asp Leu Glu Leu Asn Pro Phe Asp Gly Leu Pro Tyr
            35                  40                  45

Ser Ser Arg Tyr Tyr Lys Leu Leu Lys Glu Arg Glu Asp Leu Pro Ile
        50                  55                  60

Trp Lys Glu Lys Tyr Ser Phe Met Glu Asn Leu Leu Gln Asn Gln Ile
65                  70                  75                  80

Val Ile Val Ser Gly Asp Ala Lys Cys Gly Lys Ser Ala Gln Val Pro
                85                  90                  95

Gln Trp Cys Ala Glu Tyr Cys Leu Ser Ile His Tyr Gln His Gly Gly
                100                 105                 110
```

```
Val Ile Cys Thr Gln Val His Lys Gln Thr Met Val Gln Leu Ala Leu
        115                 120                 125

Arg Val Ala Asp Glu Met Asp Val Asn Ile Gly His Glu Val Gly Tyr
130                 135                 140

Val Ile Pro Phe Glu Asn Cys Cys Thr Asn Glu Thr Ile Leu Arg Tyr
145                 150                 155                 160

Cys Thr Asp Asp Met Leu Gln Arg Glu Met Met Ser Asn Pro Phe Leu
                165                 170                 175

Gly Ser Tyr Gly Val Ile Ile Leu Asp Asp Ile His Glu Arg Ser Ile
            180                 185                 190

Ala Thr Asp Val Leu Leu Gly Leu Leu Lys Asp Val Leu Leu Ala Arg
        195                 200                 205

Pro Glu Leu Lys Leu Ile Ile Asn Ser Ser Pro His Leu Ile Ser Lys
    210                 215                 220

Leu Asn Ser Tyr Tyr Gly Asn Val Pro Val Ile Glu Val Lys Asn Lys
225                 230                 235                 240

His Pro Val Glu Val Val Tyr Leu Ser Glu Ala Gln Lys Asp Ser Phe
                245                 250                 255

Glu Ser Ile Leu Arg Leu Ile Phe Glu Ile His His Ser Gly Glu Lys
            260                 265                 270

Gly Asp Ile Val Val Phe Leu Ala Cys Glu Gln Asp Ile Glu Lys Val
        275                 280                 285

Cys Glu Thr Val Tyr Gln Gly Ser Asn Leu Asn Pro Asp Leu Gly Glu
    290                 295                 300

Leu Val Val Val Pro Leu Tyr Pro Lys Leu Lys Cys Ser Leu Phe Lys
305                 310                 315                 320

Pro Leu Asp Glu Thr Glu Lys Arg Cys Gln Val Tyr Gln Arg Arg Val
                325                 330                 335

Val Leu Thr Thr Ser Ser Gly Glu Phe Leu Ile Trp Ser Asn Ser Val
            340                 345                 350

Arg Phe Val Ile Asp Val Gly Val Glu Arg Arg Lys Val Tyr Asn Pro
        355                 360                 365

Arg Ile Arg Ala Asn Ser Leu Val Met Gln Pro Ile Ser Gln Ser Gln
    370                 375                 380

Ala Glu Ile Arg Lys Gln Ile Leu Gly Ser Ser Ser Gly Lys Phe
385                 390                 395                 400

Phe Cys Leu Tyr Thr Glu Glu Phe Ala Ser Lys Asp Met Thr Pro Leu
                405                 410                 415

Lys Pro Ala Glu Met Gln Glu Ala Asn Leu Thr Ser Met Val Leu Phe
            420                 425                 430

Met Lys Arg Ile Asp Ile Ala Gly Leu Gly His Cys Asp Phe Met Asn
        435                 440                 445

Arg Pro Ala Pro Glu Ser Leu Met Gln Ala Ser Glu Asp Leu Asp Tyr
    450                 455                 460

Leu Ala Ala Leu Asp Asn Asp Gly Asn Leu Ser Glu Phe Gly Ile Ile
465                 470                 475                 480

Met Ser Glu Phe Pro Leu Asp Pro Gln Leu Ser Lys Ser Ile Leu Gly
                485                 490                 495

Ser Cys Glu Phe Asp Cys Val Asp Glu Val Leu Thr Ile Ala Ala Met
            500                 505                 510

Val Thr Ala Pro Asn Cys Phe Ser His Val Pro His Gly Ala Glu Glu
        515                 520                 525

Ala Ala Leu Thr Cys Trp Lys Thr Phe Leu His Pro Glu Gly Asp His
    530                 535                 540
```

```
Phe Thr Leu Ile Ser Ile Tyr Lys Ala Tyr Gln Asp Thr Thr Leu Asn
545                 550                 555                 560

Ser Ser Ser Glu Tyr Cys Val Glu Lys Trp Cys Arg Asp Tyr Phe Leu
                565                 570                 575

Asn Cys Ser Ala Leu Arg Met Ala Asp Val Ile Arg Ala Glu Leu Leu
            580                 585                 590

Glu Ile Ile Lys Arg Ile Glu Leu Pro Tyr Ala Glu Pro Ala Phe Gly
            595                 600                 605

Ser Lys Glu Asn Thr Leu Asn Ile Lys Lys Ala Leu Leu Ser Gly Tyr
        610                 615                 620

Phe Met Gln Ile Ala Arg Asp Val Asp Gly Ser Gly Asn Tyr Leu Met
625                 630                 635                 640

Leu Thr His Lys Gln Val Ala Gln Leu His Pro Leu Ser Gly Tyr Ser
                645                 650                 655

Ile Thr Lys Lys Met Pro Glu Trp Val Leu Phe His Lys Phe Ser Ile
            660                 665                 670

Ser Glu Asn Asn Tyr Ile Arg Ile Thr Ser Glu Ile Ser Leu Glu Leu
        675                 680                 685

Phe Met Gln Leu Val Pro Gln Tyr Tyr Phe Ser Asn Leu Pro Pro Ser
690                 695                 700

Glu Ser Lys Asp Ile Leu Gln Gln Val Val Asp His Leu Ser Pro Val
705                 710                 715                 720

Ser Thr Met Asn Lys Glu Gln Met Cys Glu Thr Cys Pro Glu Thr
                725                 730                 735

Glu Gln Arg Cys Thr Leu Gln
            740

<210> SEQ ID NO 5
<211> LENGTH: 2200
<212> TYPE: DNA
<213> ORGANISM: Homo sapiens

<400> SEQUENCE: 5
ttataataag gaattgcctg tgcatatctg taatgtaata tctcctgaga agatttatgt      60
tcagtggttg ttaactgaaa acttacttaa tagtttagaa gaaagatga tagctgctta      120 tgaaaactca aaatgggaac ctgttaaatg ggaaaatgat atgcactgtg ctgttaagat      180
ccaagataaa aatcagtggc gaagaggcca gatcatcaga atggttacag acacattggt      240
agaggtcttg ctgtatgatg tgggtgttga actagtagtg aatgttgact gtttaagaaa      300
acttgaagaa atctaaaga cgatgggaag actctctttg gaatgttctc tggttgacat      360
aagaccagct ggtgggagtg acaagtggac agcaacagct tgtgactgtc tttcattgta      420
cctgactgga gctgtagcaa ctataatctt acaggtggat agtgaggaaa acaacacaac      480
atggccatta cctgtgaaaa ttttctgcag agatgaaaaa ggagagcgtg ttgatgtttc      540
taaatatttg attaaaaagg gtttggcttt gagagaaagg agaattaata acttagataa      600
cagccattca ttatctgaga agtctctgga agtccccctg gaacaggaag attcagtagt      660
tactaactgt attaaaacta actttgaccc tgacaagaaa actgctgaca taatcagtga      720
acagaaagtg tctgaatttc aggagaaaat tctagaacca gaaccacta gagggtataa      780 gccaccagct attcctaaca tgaacgtatt tgaggcaaca gtcagctgtg ttggtgatga      840
tggaactata tttgtagtac ctaaactatc agaatttgag ctaataaaaa tgacaaatga      900
aattcaaagt aatttaaaat gccttggtct tttggagcct tatttctgga aaaaggaga      960 agcatgtgca gtaagaggat ccgatactct gtggtatcgt ggcaaggtga tggaggttgt    1020
```

```
aggtggcgct gtcagagtac aatatttaga tcatggattc actgaaaaga ttccgcagtg    1080
ccatctttac cctatttgc tgtatcctga tataccccag ttttgtattc cttgtcagct     1140
ccataatacc acacctgttg ggaatgtctg gcaaccagac gcaatagaag ttcttcaaca    1200
actgctttca aagagacagg tggacattca cattatgaaa ccaagatcag atcatgataa    1260
aaagtatgaa gagaaacaat gggaaataag gtttgaggaa ttgctttcgg ctgaaacaga    1320
cactcctctt ttaccaccat atttgtcttc atctctgcct tccccaggag aactctatgc    1380
tgttcaagtt aagcacgttg tctcacctaa tgaagtgtat atttgccttg attctataga    1440
aacttctaac cagtctaacc agcatagtga cacagatgat agtggagtca gcggggaatc    1500
agaatccgag agccttgatg aagcactgca gagggttaat aagaaggtag aggcgcttcc    1560
tcctctgacg gattttagaa cagaaatgcc ttgccttgca gaatatgatg atggcttatg    1620
gtatagagcg aagattgttg ccattaaaga atttaatcct ttatctatct tagtacaatt    1680
tgttgattat ggatcaactg caaagctgac attaaacaga ctgtgccaaa ttccttctca    1740
tcttatgcgg tatccagctc gagccataaa ggttctcttg cagggttta aacctccctt     1800 aagggatcta ggggagacaa gaataccata ttgtcccaaa tggagcatgg aggcactgtg    1860
ggctatgata gactgtcttc aaggaaaaca actctatgct gtgtccatgg ctccagcacc    1920
agaacagata gtgacattat atgacgatga acagcatcca gttcatatgc cgttggtaga    1980
aatggggctt gcagataaag atgaataagt gcctaagtgt atacagtgag agcatctata    2040
gaagcctaga agaattctgt tatgtttaga ctatgtctta tctttagact atttcaggct    2100
taattttcct aacttgttca gccctagtgc tttacctctc atttttaatt gaactgttag    2160
gaattgtgtg gggaaaaaaa gtaaataaat gttcgcttcc                          2200
```

<210> SEQ ID NO 6
<211> LENGTH: 633
<212> TYPE: PRT
<213> ORGANISM: Homo sapiens

<400> SEQUENCE: 6

```
Met Ile Ala Ala Tyr Glu Asn Ser Lys Trp Glu Pro Val Lys Trp Glu
1               5                   10                  15

Asn Asp Met His Cys Ala Val Lys Ile Gln Asp Lys Asn Gln Trp Arg
            20                  25                  30

Arg Gly Gln Ile Ile Arg Met Val Thr Asp Thr Leu Val Glu Val Leu
        35                  40                  45

Leu Tyr Asp Val Gly Val Glu Leu Val Val Asn Val Asp Cys Leu Arg
    50                  55                  60

Lys Leu Glu Glu Asn Leu Lys Thr Met Gly Arg Leu Ser Leu Glu Cys
65                  70                  75                  80

Ser Leu Val Asp Ile Arg Pro Ala Gly Gly Ser Asp Lys Trp Thr Ala
                85                  90                  95

Thr Ala Cys Asp Cys Leu Ser Leu Tyr Leu Thr Gly Ala Val Ala Thr
            100                 105                 110

Ile Ile Leu Gln Val Asp Ser Glu Glu Asn Asn Thr Thr Trp Pro Leu
        115                 120                 125

Pro Val Lys Ile Phe Cys Arg Asp Glu Lys Gly Glu Arg Val Asp Val
    130                 135                 140

Ser Lys Tyr Leu Ile Lys Lys Gly Leu Ala Leu Arg Glu Arg Arg Ile
145                 150                 155                 160

Asn Asn Leu Asp Asn Ser His Ser Leu Ser Glu Lys Ser Leu Glu Val
                165                 170                 175
```

```
Pro Leu Glu Gln Glu Asp Ser Val Val Thr Asn Cys Ile Lys Thr Asn
            180                 185                 190

Phe Asp Pro Asp Lys Lys Thr Ala Asp Ile Ile Ser Glu Gln Lys Val
        195                 200                 205

Ser Glu Phe Gln Glu Lys Ile Leu Glu Pro Arg Thr Thr Arg Gly Tyr
    210                 215                 220

Lys Pro Pro Ala Ile Pro Asn Met Asn Val Phe Glu Ala Thr Val Ser
225                 230                 235                 240

Cys Val Gly Asp Asp Gly Thr Ile Phe Val Val Pro Lys Leu Ser Glu
                245                 250                 255

Phe Glu Leu Ile Lys Met Thr Asn Glu Ile Gln Ser Asn Leu Lys Cys
            260                 265                 270

Leu Gly Leu Leu Glu Pro Tyr Phe Trp Lys Lys Gly Glu Ala Cys Ala
        275                 280                 285

Val Arg Gly Ser Asp Thr Leu Trp Tyr Arg Gly Lys Val Met Glu Val
    290                 295                 300

Val Gly Gly Ala Val Arg Val Gln Tyr Leu Asp His Gly Phe Thr Glu
305                 310                 315                 320

Lys Ile Pro Gln Cys His Leu Tyr Pro Ile Leu Leu Tyr Pro Asp Ile
                325                 330                 335

Pro Gln Phe Cys Ile Pro Cys Gln Leu His Asn Thr Thr Pro Val Gly
            340                 345                 350

Asn Val Trp Gln Pro Asp Ala Ile Glu Val Leu Gln Gln Leu Leu Ser
        355                 360                 365

Lys Arg Gln Val Asp Ile His Ile Met Lys Pro Arg Ser Asp His Asp
    370                 375                 380

Lys Lys Tyr Glu Glu Lys Gln Trp Glu Ile Arg Phe Glu Glu Leu Leu
385                 390                 395                 400

Ser Ala Glu Thr Asp Thr Pro Leu Leu Pro Pro Tyr Leu Ser Ser Ser
                405                 410                 415

Leu Pro Ser Pro Gly Glu Leu Tyr Ala Val Gln Val Lys His Val Val
            420                 425                 430

Ser Pro Asn Glu Val Tyr Ile Cys Leu Asp Ser Ile Glu Thr Ser Asn
        435                 440                 445

Gln Ser Asn Gln His Ser Asp Thr Asp Ser Gly Val Ser Gly Glu
    450                 455                 460

Ser Glu Ser Glu Ser Leu Asp Glu Ala Leu Gln Arg Val Asn Lys Lys
465                 470                 475                 480

Val Glu Ala Leu Pro Pro Leu Thr Asp Phe Arg Thr Glu Met Pro Cys
                485                 490                 495

Leu Ala Glu Tyr Asp Asp Gly Leu Trp Tyr Arg Ala Lys Ile Val Ala
            500                 505                 510

Ile Lys Glu Phe Asn Pro Leu Ser Ile Leu Val Gln Phe Val Asp Tyr
        515                 520                 525

Gly Ser Thr Ala Lys Leu Thr Leu Asn Arg Leu Cys Gln Ile Pro Ser
    530                 535                 540

His Leu Met Arg Tyr Pro Ala Arg Ala Ile Lys Val Leu Leu Ala Gly
545                 550                 555                 560

Phe Lys Pro Pro Leu Arg Asp Leu Gly Glu Thr Arg Ile Pro Tyr Cys
                565                 570                 575

Pro Lys Trp Ser Met Glu Ala Leu Trp Ala Met Ile Asp Cys Leu Gln
            580                 585                 590

Gly Lys Gln Leu Tyr Ala Val Ser Met Ala Pro Ala Pro Glu Gln Ile
        595                 600                 605
```

-continued

Val Thr Leu Tyr Asp Asp Glu Gln His Pro Val His Met Pro Leu Val
    610                 615                 620

Glu Met Gly Leu Ala Asp Lys Asp Glu
625                 630

<210> SEQ ID NO 7
<211> LENGTH: 1860
<212> TYPE: DNA
<213> ORGANISM: Homo sapiens

<400> SEQUENCE: 7

| | | | | | | |
|---|---|---|---|---|---|---|
| agcgcgaccc | gacagcctgg | gaaacggaca | gccgtgtcag | aagggcaggt | gccagtgggc | 60 |
| aggaggccgg | agagaaagcc | gcagcttcct | tccacctcgc | gccgggcccg | cggccgcgca | 120 |
| cggggaccgc | tccgagttcc | tcccggcggg | aaccccccgc | cccagaactt | tggtctcgtc | 180 |
| ccacccaccc | ccgcccgcgc | catggtctcg | ccctagggag | ccatcgataa | ctctacgctc | 240 |
| ggcctcgatc | gactcgctcc | ggctccccte | gccgtcctgg | acggcggga | gtgcggagcc | 300 |
| gcccgtaaga | tgctctgacc | tttgaccctg | ccgttcagct | ctagggcccg | tgcaggccac | 360 |
| accatgaaca | cctccccagg | cacggtgggc | agtgacccgg | tcatcctggc | cactgcaggc | 420 |
| tacgaccaca | ccgtgcgctt | ctggcaggcc | cacagcggca | tctgcacccg | gacggtgcag | 480 |
| caccaggact | ccgtgaatgc | cttggaggtc | acaccggacc | gcagcatgat | tgctgctgca | 540 |
| ggttaccagc | acatccgcat | gtatgatctc | aactccaata | accctaaccc | catcatcagc | 600 |
| tacgacggcg | tcaacaagaa | catcgcgtct | gtgggcttcc | acgaagacgg | ccgctggatg | 660 |
| tacacgggcg | gcgaggactg | cacagccagg | atctgggacc | tcaggtcccg | gaacctgcag | 720 |
| tgccagcgga | tcttccaggt | gaacgcaccc | attaactgcg | tgtgcctgca | cccgaaccag | 780 |
| gcagagctca | tcgtgggtga | ccagagcggg | gctatccaca | tctgggactt | gaaaacagac | 840 |
| cacaacgagc | agctgatccc | tgagcccgag | gtctccatca | cgtccgccca | catcgatccc | 900 |
| gacgccagct | acatggcagc | tgtcaatagc | accggaaact | gctatgtctg | gaatctgacg | 960 |
| gggggcattg | gtgacgaggt | gacccagctc | atccccaaga | ctaagatccc | tgcccacacg | 1020 |
| cgctacgccc | tgcagtgtcg | cttcagcccc | gactccacgc | tcctcgccac | ctgctcggct | 1080 |
| gatcagacgt | gcaagatctg | gaggacgtcc | aacttctccc | tgatgacgga | gctgagcatc | 1140 |
| aagagcggca | accccgggga | gtcctcccgc | ggctggatgt | ggggctgcgc | cttctcgggg | 1200 |
| gactcccagt | acatcgtcac | tgcttcctcg | gacaacctgg | cccggctctg | gtgtgtggag | 1260 |
| actggagaga | tcaagagaga | gtatggcggc | caccagaagg | ctgttgtctg | cctggccttc | 1320 |
| aatgacagtg | tgctgggcta | gcctgtgacc | cctcgggact | gcctggtgca | ggtggtggca | 1380 |
| gctggaggga | cccatgcagc | acccaggtca | gagcagaccc | tccccctgccg | gcctgcgcca | 1440 |
| gctggacctg | atggcccct | gtggcgcctt | gacctgctgg | gccaggctgc | cctgggactc | 1500 |
| tcagcccca | gttgcttatc | cagatgtgac | agagctcgac | ccaagccagg | ctgcacactc | 1560 |
| ctggactggg | ctagcctgca | ctgcctggga | aagtcggccg | agggcccaaa | gctgctgagg | 1620 |
| ggtctgaggc | tggtgcccac | cccaagcta | gtgtgttctc | tgcccctccc | tgcccgcgtt | 1680 |
| tcagggcctc | ggtccataga | gaacaccacc | accatggcca | ggtggaaggg | tttattagtc | 1740 |
| cctgccagca | gctgtcctcc | ctggtgcagg | tggcctggcc | agcccactgg | attggggacg | 1800 |
| ggccaggctg | ggccaggtcg | ggggctcagt | ctgggaggta | ataaaagcag | accgacacgc | 1860 |

```
<210> SEQ ID NO 8
<211> LENGTH: 325
<212> TYPE: PRT
<213> ORGANISM: Homo sapiens

<400> SEQUENCE: 8

Met Asn Thr Ser Pro Gly Thr Val Gly Ser Asp Pro Val Ile Leu Ala
1               5                   10                  15

Thr Ala Gly Tyr Asp His Thr Val Arg Phe Trp Gln Ala His Ser Gly
            20                  25                  30

Ile Cys Thr Arg Thr Val Gln His Gln Asp Ser Val Asn Ala Leu Glu
        35                  40                  45

Val Thr Pro Asp Arg Ser Met Ile Ala Ala Gly Tyr Gln His Ile
    50                  55                  60

Arg Met Tyr Asp Leu Asn Ser Asn Asn Pro Asn Pro Ile Ile Ser Tyr
65                  70                  75                  80

Asp Gly Val Asn Lys Asn Ile Ala Ser Val Gly Phe His Glu Asp Gly
                85                  90                  95

Arg Trp Met Tyr Thr Gly Gly Glu Asp Cys Thr Ala Arg Ile Trp Asp
            100                 105                 110

Leu Arg Ser Arg Asn Leu Gln Cys Gln Arg Ile Phe Gln Val Asn Ala
        115                 120                 125

Pro Ile Asn Cys Val Cys Leu His Pro Asn Gln Ala Glu Leu Ile Val
    130                 135                 140

Gly Asp Gln Ser Gly Ala Ile His Ile Trp Asp Leu Lys Thr Asp His
145                 150                 155                 160

Asn Glu Gln Leu Ile Pro Glu Pro Glu Val Ser Ile Thr Ser Ala His
                165                 170                 175

Ile Asp Pro Asp Ala Ser Tyr Met Ala Ala Val Asn Ser Thr Gly Asn
            180                 185                 190

Cys Tyr Val Trp Asn Leu Thr Gly Gly Ile Gly Asp Glu Val Thr Gln
        195                 200                 205

Leu Ile Pro Lys Thr Lys Ile Pro Ala His Thr Arg Tyr Ala Leu Gln
    210                 215                 220

Cys Arg Phe Ser Pro Asp Ser Thr Leu Leu Ala Thr Cys Ser Ala Asp
225                 230                 235                 240

Gln Thr Cys Lys Ile Trp Arg Thr Ser Asn Phe Ser Leu Met Thr Glu
                245                 250                 255

Leu Ser Ile Lys Ser Gly Asn Pro Gly Glu Ser Ser Arg Gly Trp Met
            260                 265                 270

Trp Gly Cys Ala Phe Ser Gly Asp Ser Gln Tyr Ile Val Thr Ala Ser
        275                 280                 285

Ser Asp Asn Leu Ala Arg Leu Trp Cys Val Glu Thr Gly Glu Ile Lys
    290                 295                 300

Arg Glu Tyr Gly Gly His Gln Lys Ala Val Val Cys Leu Ala Phe Asn
305                 310                 315                 320

Asp Ser Val Leu Gly
            325

<210> SEQ ID NO 9
<211> LENGTH: 2538
<212> TYPE: DNA
<213> ORGANISM: Homo sapiens
```

```
<400> SEQUENCE: 9
attctccact gaggcccagc tgttcctctc cttgaaaagt caaggcttgg ttcaagccag      60
atagcacctg aggacagaac atatcaggag ccaagttaca ccctgtttaa ccctgccttc     120
aaagggacga ctctgtaaga ttctctgcta cttattcaag ttgacacgat gcccttcaca     180
ctccacctga ggtcccgcct tccctctgcc ataaggagtt tgattctaca aaagaaacca     240
aacatcagaa atacatccag catgctggag gagctccgac cagccagcct ggtggtcctg     300
cccaggtccc ttgctccagc ttttgaaaga ttctgccagg tcaacactgg tcctctaccc     360
ctgctgggcc agagtgagcc agaaaagtgg atgctgcccc ctcaaggtgc tatctcagag     420
accaggatgg gccatcccca gttctggaaa tacgagttcg gtgcctgcac cggtagcctg     480
gcttcgctgg agcagtactc ggagcagctg aaggacatgg tggccttctt cctgggctgc     540
agcttctccc tggaggaggc cttggagaaa gcggggctcc ccagaagaga cccagcaggt     600
cacagccaga caacagtgcc ttgtgttacc catgctggct tctgctgccc tctggtggtc     660
acgatgaggc ccattcccaa ggacaagctg aagggctggt gcgggcctg ctgctccctc      720 ggaggtgagc aggggcaacc tgttcacatg gcgacccag aactgttggg aatcaaagag      780 cttttccaaac ctgcctacgg ggatgccatg gtgtgtcccc caggggaggt tccagtgttc    840
tggccttctc cgctgaccag tctcggagct gtcagcagct gtgagacccc actggctttt     900
gccagcatcc caggctgcac agttatgact gacctgaagg atgcaaaggc tccacctggt     960
tgtctcaccc cagagagaat tccagaggtc catcacattt cccaagatcc tctgcactac    1020
agcatcgcgt cagtctctgc ttctcagaag atcagagaac tagagtctat gatcggcata    1080
gacccaggga accggggat tgggcacctg ctctgtaaag atgagctgct gaaggcctct     1140
ctctcgctgt cccatgcccg ctcagtgctc atcaccactg ggttccccac acatttcaat    1200
catgagcctc cagaagagac agatggccca ccaggagctg ttgctctggt tgccttcctg    1260
caggccttgg agaaggaggt cgccataatc gttgaccaga gagcctggaa cttgcaccag    1320
aagattgttg aagatgctgt tgagcaaggt gttctgaaga cgcagatccc gatattaact    1380
taccaaggtg gatcagtgga agctgctcag gcattcctgt gcaaaaatgg ggacccgcag    1440
acacctagat ttgaccacct ggtggccata gagcgtgccg gaagagctgc tgatggcaat    1500
tactacaatg caaggaagat gaacatcaag cacttggttg accccattga cgatctttt    1560 cttgctgcga agaagattcc tggaatctca tcaactggag tcggtgatgg aggcaacgag    1620
cttgggatgg gtaaagtcaa ggaggctgtg aggaggcaca tacggcacgg ggatgtcatc    1680
gcctgcgacg tggaggctga cttgccgtc attgctggtg tttctaactg ggagggctat    1740
gccctggcct gcgcactcta catcctgtac tcatgtgctg tccacagtca gtacctgagg    1800
aaagcagtcg accctccag ggcacctgga gatcaggcct ggactcaggc cctccgtcg     1860 gtcattaagg aagaaaaat gctgggcatc ttggtgcagc acaaagtccg gagtggcgtc    1920
tcgggcatcg tgggcatgga ggtggatggg ctgcccttcc acaacaccca cgccgagatg    1980
atccagaagc tggtggacgt caccacggca caggtgtaac cgtccatgtt ccgtgtgagc    2040
agagtcccta ccaacgggca ggtctgcatc cggggagaat gcagctgctt ctggcgacaa    2100
tcctgctagt aaacactggt cttcggtgag caacgaacac tcgcctggcc tgggaaactg    2160
catgcccact ttctggggagg ggttagtgca ggtgccgtgg acaaaggaca acatttctct    2220
ggggcttttt aacttttatt cctaagactc taaaggcgtt gatttcaacc ctccttcact    2280
ctggcttctt caggcaaccc acgtggtctc ctgtgagaat cttctcgaca gttacttatg    2340
```

```
gggacacttg tgaacaatta actgccaggc agagcatgag aacaaacatt cccaggccat    2400
gtaggatagg atactccaga ctccagtcat cctcccccat ccatggtttc tgttactcat    2460
ggtttcagtt actcatagcc aactgcagac cgaaaatact aaatgaaaaa tttcagaaat    2520
aaacaactct taagtttt                                                  2538
```

<210> SEQ ID NO 10
<211> LENGTH: 616
<212> TYPE: PRT
<213> ORGANISM: Homo sapiens

<400> SEQUENCE: 10

```
Met Pro Phe Thr Leu His Leu Arg Ser Arg Leu Pro Ser Ala Ile Arg
1               5                   10                  15

Ser Leu Ile Leu Gln Lys Lys Pro Asn Ile Arg Asn Thr Ser Ser Met
            20                  25                  30

Ala Gly Glu Leu Arg Pro Ala Ser Leu Val Val Leu Pro Arg Ser Leu
        35                  40                  45

Ala Pro Ala Phe Glu Arg Phe Cys Gln Val Asn Thr Gly Pro Leu Pro
    50                  55                  60

Leu Leu Gly Gln Ser Glu Pro Glu Lys Trp Met Leu Pro Pro Gln Gly
65                  70                  75                  80

Ala Ile Ser Glu Thr Arg Met Gly His Pro Gln Phe Trp Lys Tyr Glu
                85                  90                  95

Phe Gly Ala Cys Thr Gly Ser Leu Ala Ser Leu Glu Gln Tyr Ser Glu
            100                 105                 110

Gln Leu Lys Asp Met Val Ala Phe Phe Leu Gly Cys Ser Phe Ser Leu
        115                 120                 125

Glu Glu Ala Leu Glu Lys Ala Gly Leu Pro Arg Arg Asp Pro Ala Gly
    130                 135                 140

His Ser Gln Thr Thr Val Pro Cys Val Thr His Ala Gly Phe Cys Cys
145                 150                 155                 160

Pro Leu Val Val Thr Met Arg Pro Ile Pro Lys Asp Lys Leu Glu Gly
                165                 170                 175

Leu Val Arg Ala Cys Cys Ser Leu Gly Gly Glu Gln Gly Gln Pro Val
            180                 185                 190

His Met Gly Asp Pro Glu Leu Leu Gly Ile Lys Glu Leu Ser Lys Pro
        195                 200                 205

Ala Tyr Gly Asp Ala Met Val Cys Pro Pro Gly Glu Val Pro Val Phe
    210                 215                 220

Trp Pro Ser Pro Leu Thr Ser Leu Gly Ala Val Ser Ser Cys Glu Thr
225                 230                 235                 240

Pro Leu Ala Phe Ala Ser Ile Pro Gly Cys Thr Val Met Thr Asp Leu
                245                 250                 255

Lys Asp Ala Lys Ala Pro Pro Gly Cys Leu Thr Pro Glu Arg Ile Pro
            260                 265                 270

Glu Val His His Ile Ser Gln Asp Pro Leu His Tyr Ser Ile Ala Ser
        275                 280                 285

Val Ser Ala Ser Gln Lys Ile Arg Glu Leu Glu Ser Met Ile Gly Ile
    290                 295                 300

Asp Pro Gly Asn Arg Gly Ile Gly His Leu Leu Cys Lys Asp Glu Leu
305                 310                 315                 320

Leu Lys Ala Ser Leu Ser Leu Ser His Ala Arg Ser Val Leu Ile Thr
                325                 330                 335
```

```
Thr Gly Phe Pro Thr His Phe Asn His Glu Pro Pro Glu Glu Thr Asp
            340                 345                 350

Gly Pro Pro Gly Ala Val Ala Leu Val Ala Phe Leu Gln Ala Leu Glu
        355                 360                 365

Lys Glu Val Ala Ile Ile Val Asp Gln Arg Ala Trp Asn Leu His Gln
370                 375                 380

Lys Ile Val Glu Asp Ala Val Glu Gln Gly Val Leu Lys Thr Gln Ile
385                 390                 395                 400

Pro Ile Leu Thr Tyr Gln Gly Gly Ser Val Glu Ala Ala Gln Ala Phe
                405                 410                 415

Leu Cys Lys Asn Gly Asp Pro Gln Thr Pro Arg Phe Asp His Leu Val
            420                 425                 430

Ala Ile Glu Arg Ala Gly Arg Ala Ala Asp Gly Asn Tyr Tyr Asn Ala
        435                 440                 445

Arg Lys Met Asn Ile Lys His Leu Val Asp Pro Ile Asp Asp Leu Phe
450                 455                 460

Leu Ala Ala Lys Lys Ile Pro Gly Ile Ser Ser Thr Gly Val Gly Asp
465                 470                 475                 480

Gly Gly Asn Glu Leu Gly Met Gly Lys Val Lys Glu Ala Val Arg Arg
                485                 490                 495

His Ile Arg His Gly Asp Val Ile Ala Cys Asp Val Glu Ala Asp Phe
            500                 505                 510

Ala Val Ile Ala Gly Val Ser Asn Trp Gly Gly Tyr Ala Leu Ala Cys
        515                 520                 525

Ala Leu Tyr Ile Leu Tyr Ser Cys Ala Val His Ser Gln Tyr Leu Arg
530                 535                 540

Lys Ala Val Gly Pro Ser Arg Ala Pro Gly Asp Gln Ala Trp Thr Gln
545                 550                 555                 560

Ala Leu Pro Ser Val Ile Lys Glu Glu Lys Met Leu Gly Ile Leu Val
                565                 570                 575

Gln His Lys Val Arg Ser Gly Val Ser Gly Ile Val Gly Met Glu Val
            580                 585                 590

Asp Gly Leu Pro Phe His Asn Thr His Ala Glu Met Ile Gln Lys Leu
        595                 600                 605

Val Asp Val Thr Thr Ala Gln Val
610                 615

<210> SEQ ID NO 11
<211> LENGTH: 1641
<212> TYPE: DNA
<213> ORGANISM: Homo sapiens

<400> SEQUENCE: 11
gctgatgctg ccgtgcggta cttgtcatgg agctggcact gcggcgctct cccgtcccgc       60
ggtggttgct gctgctgccg ctgctgctgg gcctgaacgc aggagctgtc attgactggc      120
ccacagagga gggcaaggaa gtatgggatt atgtgacggt ccgcaaggat gcctacatgt      180
tctggtggct ctattatgcc accaactcct gcaagaactt ctcagaactg ccctggtca       240 tgtggcttca gggcggtcca gcggttcta gcactggatt tggaaacttt gaggaaattg      300
ggccccttga cagtgatctc aaaccacgga aaaccacctg ctccaggct gccagtctcc       360 tatttgtgga taatcccgtg ggcactgggt tcagttatgt gaatggtagt ggtgcctatg      420
ccaaggacct ggctatggtg gcttcagaca tgatggttct cctgaagacc ttcttcagtt      480
gccacaaaga attccagaca gttccattct acatttctc agagtcctat ggaggaaaaa       540
```

```
tggcagctgg cattggtcta gagctttata aggccattca gcgagggacc atcaagtgca    600
actttgcggg ggttgccttg ggtgattcct ggatctcccc tgttgattcg gtgctctcct    660
ggggacctta cctgtacagc atgtctcttc tcgaagacaa aggtctggca gaggtgtcta    720
aggttgcaga gcaagtactg aatgccgtaa ataaggggct ctacagagag ccacagagc     780
tgtgggggaa agcagaaatg atcattgaac agaacacaga tggggtgaac ttctataaca    840
tcttaactaa aagcactccc acgtctacaa tggagtcgag tctagaattc acacagagcc    900
acctagtttg tctttgtcag cgccacgtga gacacctaca acgagatgcc ttaagccagc    960
tcatgaatgg ccccatcaga aagaagctca aaattattcc tgaggatcaa tcctggggag   1020
gccaggctac caacgtcttt gtgaacatgg aggaggactt catgaagcca gtcattagca   1080
ttgtggacga gttgctggag gcagggatca acgtgacggt gtataatgga cagctggatc   1140
tcatcgtaga taccatgggt caggaggcct gggtgcggaa actgaagtgg ccagaactgc   1200
ctaaattcag tcagctgaag tggaaggccc tgtacagtga ccctaaatct ttggaaacat   1260
ctgcttttgt caagtcctac aagaaccttg ctttctactg gattctgaaa gctggtcata   1320
tggttccttc tgaccaaggg gacatggctc tgaagatgat gagactggtg actcagcaag   1380
aataggatgg atggggctgg agatgagctg gtttggcctt ggggcacaga gctgagctga   1440
ggccgctgaa gctgtaggaa gcgccactct tccctgtatc taactggggc tgtgatcaag   1500
aaggttctga ccagcttctg cagaggataa aatcattgtc tctggaggca atttggaaat   1560
tatttctgct tcttaaaaaa acctaagatt ttttaaaaaa ttgatttgtt ttgatcaaaa   1620
taaaggatga taatagatat t                                             1641

<210> SEQ ID NO 12
<211> LENGTH: 452
<212> TYPE: PRT
<213> ORGANISM: Homo sapiens

<400> SEQUENCE: 12

Met Glu Leu Ala Leu Arg Arg Ser Pro Val Pro Arg Trp Leu Leu Leu
1               5                   10                  15

Leu Pro Leu Leu Leu Gly Leu Asn Ala Gly Ala Val Ile Asp Trp Pro
            20                  25                  30

Thr Glu Glu Gly Lys Glu Val Trp Asp Tyr Val Thr Val Arg Lys Asp
        35                  40                  45

Ala Tyr Met Phe Trp Trp Leu Tyr Tyr Ala Thr Asn Ser Cys Lys Asn
    50                  55                  60

Phe Ser Glu Leu Pro Leu Val Met Trp Leu Gln Gly Pro Gly Gly
65                  70                  75                  80

Ser Ser Thr Gly Phe Gly Asn Phe Glu Glu Ile Gly Pro Leu Asp Ser
                85                  90                  95

Asp Leu Lys Pro Arg Lys Thr Thr Trp Leu Gln Ala Ala Ser Leu Leu
            100                 105                 110

Phe Val Asp Asn Pro Val Gly Thr Gly Phe Ser Tyr Val Asn Gly Ser
        115                 120                 125

Gly Ala Tyr Ala Lys Asp Leu Ala Met Val Ala Ser Asp Met Met Val
    130                 135                 140

Leu Leu Lys Thr Phe Phe Ser Cys His Lys Glu Phe Gln Thr Val Pro
145                 150                 155                 160

Phe Tyr Ile Phe Ser Glu Ser Tyr Gly Gly Lys Met Ala Ala Gly Ile
                165                 170                 175
```

```
Gly Leu Glu Leu Tyr Lys Ala Ile Gln Arg Gly Thr Ile Lys Cys Asn
            180                 185                 190

Phe Ala Gly Val Ala Leu Gly Asp Ser Trp Ile Ser Pro Val Asp Ser
        195                 200                 205

Val Leu Ser Trp Gly Pro Tyr Leu Tyr Ser Met Ser Leu Leu Glu Asp
    210                 215                 220

Lys Gly Leu Ala Glu Val Ser Lys Val Ala Glu Gln Val Leu Asn Ala
225                 230                 235                 240

Val Asn Lys Gly Leu Tyr Arg Glu Ala Thr Glu Leu Trp Gly Lys Ala
                245                 250                 255

Glu Met Ile Ile Glu Gln Asn Thr Asp Gly Val Asn Phe Tyr Asn Ile
            260                 265                 270

Leu Thr Lys Ser Thr Pro Thr Ser Thr Met Glu Ser Ser Leu Glu Phe
        275                 280                 285

Thr Gln Ser His Leu Val Cys Leu Cys Gln Arg His Val Arg His Leu
    290                 295                 300

Gln Arg Asp Ala Leu Ser Gln Leu Met Asn Gly Pro Ile Arg Lys Lys
305                 310                 315                 320

Leu Lys Ile Ile Pro Glu Asp Gln Ser Trp Gly Gly Gln Ala Thr Asn
                325                 330                 335

Val Phe Val Asn Met Glu Glu Asp Phe Met Lys Pro Val Ile Ser Ile
            340                 345                 350

Val Asp Glu Leu Leu Glu Ala Gly Ile Asn Val Thr Val Tyr Asn Gly
        355                 360                 365

Gln Leu Asp Leu Ile Val Asp Thr Met Gly Gln Glu Ala Trp Val Arg
    370                 375                 380

Lys Leu Lys Trp Pro Glu Leu Pro Lys Phe Ser Gln Leu Lys Trp Lys
385                 390                 395                 400

Ala Leu Tyr Ser Asp Pro Lys Ser Leu Glu Thr Ser Ala Phe Val Lys
                405                 410                 415

Ser Tyr Lys Asn Leu Ala Phe Tyr Trp Ile Leu Lys Ala Gly His Met
            420                 425                 430

Val Pro Ser Asp Gln Gly Asp Met Ala Leu Lys Met Met Arg Leu Val
        435                 440                 445

Thr Gln Gln Glu
    450

<210> SEQ ID NO 13
<211> LENGTH: 2311
<212> TYPE: DNA
<213> ORGANISM: Homo sapiens

<400> SEQUENCE: 13
agacacaagg agaggcttgg agagagcaga cgccttctgg attcaagaag acgaggccca      60
ttcccctcag gctcacctgt tactcggcct cccagaaaga tggataggag aaatgactac     120
ggatataggg tgcctctatt tcagggccct ctgcctcccc ggggagcct  ggggcttccc     180 ttccctccag atatacagac tgagaccaca gaagaggaca gtgtcctgct gatgcatacc     240
ctgttggcgg caaccaagga ctccctggcc atggacccac cagttgtcaa ccggcctaag     300
aaaagcaaga ccaagaaggc ccctataaag actattacta aggctgcacc tgctgcccct     360
ccagtcccag ctgccaatga gattgccacc aacaagccca aataacttg  gcaggcttta     420 aacctgccta tcattaccca gatcagccag gctttaccta ccactgaggt aaccaatact     480
caggcttctt cagtcactgc tcagcctaag aaagccaaca agatgaagag agttactgcc     540
```

```
aaggcagccc aaggctccca atccccaact ggccatgagg gtggcactat acagctgaag    600
tcacccttgc aggtcctaaa gctaccagtc atctcacaga atattcacgc tccaattgcc    660
aatgagtcag ccagttccca agccttgata acctctatca agcctaagaa agcttccaag    720
gctaagaagg ctgcaaataa ggccatagct agtgccaccg aggtctcgct ggctgcaact    780
gccacccata cagctaccac ccaaggccaa attaccaatg agacagccag tatccacacc    840
acagcagcct ccatccgaac caagaaagcc tccaaagcca ggaagacaat tgctaaggtc    900
ataaatactg acactgagca tatagaggct ctaaatgtca ctgacgcagc taccaggcag    960
attgaggcct cagtagtggc tatcaggccc aaaaaatcca agggcaagaa ggctgccagc   1020
aggggcccaa attctgtctc tgagatctct gaggccccac ttgccactca gatagtcaca   1080
aaccaagccc tggcagccac cctgcgggtc aagagagggt ctagggctcg aaggctgcc    1140 actaaggctc gggcaactga agccagact ccaaatgctg accaaggggc ccaggccaag   1200
atagcctctg ctcagaccaa cgtaagtgcc cttgagactc aggttgctgc tgctgtccag   1260
gccctggcag atgactatct ggctcagttg agcctggagc ccacaaccag gacccggggc   1320
aaaagaaacc gaaagtccaa gcatctgaat ggggatgaga gaagtggcag taattacagg   1380
cggatcccat ggggccggag gcctgcacca ccgcgagatg tggccatttt acaagaaagg   1440
gctaataagt tggtgaaata cctgttggtt aaggaccaga caaagatccc catcaaacgc   1500
tcagacatgc tgagggatgt catccaagaa tatgatgaat atttcccaga aatcattgaa   1560
cgagcaagct acactctgga gaagatgttt cgagtcaatc tgaaagaaat tgataagcaa   1620
agtagcttgt atattctcat cagcactcag gaatcctctg caggcatact gggaacgacc   1680
aaggacacac ccaagctggg tctcctcatg gtgattctga gtgtcatttt tatgaatggc   1740
aacaaggcca gtgaggctgt catctgggag gtgctgcgca gttgggct gcgccctggg   1800 gtgaggcatt cactctttgg ggaagtgagg aagctcatca cagacgagtt tgtgaagcag   1860
aagtacctgg agtacaagag ggtccctaac agcagaccac ctgaatatga gttcttctgg   1920
ggcttgcgct cctaccacga gactagcaag atgaaagtcc tcaagtttgc atgcagggtg   1980
cagaagaaag accccaagga ctgggctgtg cagtaccgcg aggcagtgga gatggaagtc   2040
caagctgcag ctgtggctgt ggctgaggct gaagccaggg ctgagattta ttccccatgt   2100
ttacagatac cgctaataaa ttgcagtagt ccttcccatg gagccaaagt acatccttgg   2160
aatctttgtc cacacagcag tcaaggcagt tatggccaat cagctgaggg tgtcatgtga   2220
tggaaaaatc tgtttgctgt tcctgcttta ttgtttgctt tctgtgtgct gtcatatttt   2280
ggtatcagag ttacattaaa tttgcaaaat g                                  2311
```

<210> SEQ ID NO 14
<211> LENGTH: 706
<212> TYPE: PRT
<213> ORGANISM: Homo sapiens

<400> SEQUENCE: 14

Met Asp Arg Arg Asn Asp Tyr Gly Tyr Arg Val Pro Leu Phe Gln Gly
1               5                   10                  15

Pro Leu Pro Pro Pro Gly Ser Leu Gly Leu Pro Phe Pro Pro Asp Ile
            20                  25                  30

Gln Thr Glu Thr Thr Glu Glu Asp Ser Val Leu Leu Met His Thr Leu
        35                  40                  45

Leu Ala Ala Thr Lys Asp Ser Leu Ala Met Asp Pro Pro Val Val Asn
    50                  55                  60

-continued

```
Arg Pro Lys Lys Ser Lys Thr Lys Lys Ala Pro Ile Lys Thr Ile Thr
 65                  70                  75                  80

Lys Ala Ala Pro Ala Pro Pro Val Pro Ala Ala Asn Glu Ile Ala
             85                  90                  95

Thr Asn Lys Pro Lys Ile Thr Trp Gln Ala Leu Asn Leu Pro Val Ile
            100                 105                 110

Thr Gln Ile Ser Gln Ala Leu Pro Thr Thr Glu Val Thr Asn Thr Gln
            115                 120                 125

Ala Ser Ser Val Thr Ala Gln Pro Lys Lys Ala Asn Lys Met Lys Arg
            130                 135                 140

Val Thr Ala Lys Ala Ala Gln Gly Ser Gln Ser Pro Thr Gly His Glu
145                 150                 155                 160

Gly Gly Thr Ile Gln Leu Lys Ser Pro Leu Gln Val Leu Lys Leu Pro
                165                 170                 175

Val Ile Ser Gln Asn Ile His Ala Pro Ile Ala Asn Glu Ser Ala Ser
                180                 185                 190

Ser Gln Ala Leu Ile Thr Ser Ile Lys Pro Lys Lys Ala Ser Lys Ala
            195                 200                 205

Lys Lys Ala Ala Asn Lys Ala Ile Ala Ser Ala Thr Glu Val Ser Leu
210                 215                 220

Ala Ala Thr Ala Thr His Thr Ala Thr Gln Gly Gln Ile Thr Asn
225                 230                 235                 240

Glu Thr Ala Ser Ile His Thr Thr Ala Ala Ser Ile Arg Thr Lys Lys
                245                 250                 255

Ala Ser Lys Ala Arg Lys Thr Ile Ala Lys Val Ile Asn Thr Asp Thr
                260                 265                 270

Glu His Ile Glu Ala Leu Asn Val Thr Asp Ala Ala Thr Arg Gln Ile
            275                 280                 285

Glu Ala Ser Val Val Ala Ile Arg Pro Lys Lys Ser Lys Gly Lys Lys
290                 295                 300

Ala Ala Ser Arg Gly Pro Asn Ser Val Ser Glu Ile Ser Glu Ala Pro
305                 310                 315                 320

Leu Ala Thr Gln Ile Val Thr Asn Gln Ala Leu Ala Ala Thr Leu Arg
                325                 330                 335

Val Lys Arg Gly Ser Arg Ala Arg Lys Ala Thr Lys Ala Arg Ala
                340                 345                 350

Thr Glu Ser Gln Thr Pro Asn Ala Asp Gln Gly Ala Gln Ala Lys Ile
            355                 360                 365

Ala Ser Ala Gln Thr Asn Val Ser Ala Leu Glu Thr Gln Val Ala Ala
            370                 375                 380

Ala Val Gln Ala Leu Ala Asp Asp Tyr Leu Ala Gln Leu Ser Leu Glu
385                 390                 395                 400

Pro Thr Thr Arg Thr Arg Gly Lys Arg Asn Arg Lys Ser Lys His Leu
                405                 410                 415

Asn Gly Asp Glu Arg Ser Gly Ser Asn Tyr Arg Arg Ile Pro Trp Gly
            420                 425                 430

Arg Arg Pro Ala Pro Pro Arg Asp Val Ala Ile Leu Gln Glu Arg Ala
            435                 440                 445

Asn Lys Leu Val Lys Tyr Leu Leu Val Lys Asp Gln Thr Lys Ile Pro
            450                 455                 460

Ile Lys Arg Ser Asp Met Leu Arg Asp Val Ile Gln Glu Tyr Asp Glu
465                 470                 475                 480

Tyr Phe Pro Glu Ile Ile Glu Arg Ala Ser Tyr Thr Leu Glu Lys Met
                485                 490                 495
```

-continued

```
Phe Arg Val Asn Leu Lys Glu Ile Asp Lys Gln Ser Ser Leu Tyr Ile
            500                 505                 510
Leu Ile Ser Thr Gln Glu Ser Ser Ala Gly Ile Leu Gly Thr Thr Lys
        515                 520                 525
Asp Thr Pro Lys Leu Gly Leu Leu Met Val Ile Leu Ser Val Ile Phe
530                 535                 540
Met Asn Gly Asn Lys Ala Ser Glu Ala Val Ile Trp Glu Val Leu Arg
545                 550                 555                 560
Lys Leu Gly Leu Arg Pro Gly Val Arg His Ser Leu Phe Gly Glu Val
                565                 570                 575
Arg Lys Leu Ile Thr Asp Glu Phe Val Lys Gln Lys Tyr Leu Glu Tyr
            580                 585                 590
Lys Arg Val Pro Asn Ser Arg Pro Glu Tyr Glu Phe Phe Trp Gly
        595                 600                 605
Leu Arg Ser Tyr His Glu Thr Ser Lys Met Lys Val Leu Lys Phe Ala
610                 615                 620
Cys Arg Val Gln Lys Lys Asp Pro Lys Asp Trp Ala Val Gln Tyr Arg
625                 630                 635                 640
Glu Ala Val Glu Met Glu Val Gln Ala Ala Val Ala Val Ala Glu
                645                 650                 655
Ala Glu Ala Arg Ala Glu Ile Tyr Ser Pro Cys Leu Gln Ile Pro Leu
            660                 665                 670
Ile Asn Cys Ser Ser Pro Ser His Gly Ala Lys Val His Pro Trp Asn
        675                 680                 685
Leu Cys Pro His Ser Ser Gln Gly Ser Tyr Gly Gln Ser Ala Glu Gly
    690                 695                 700
Val Met
705

<210> SEQ ID NO 15
<211> LENGTH: 2617
<212> TYPE: DNA
<213> ORGANISM: Homo sapiens

<400> SEQUENCE: 15
agtctccgca gagcccgggc gggagtagct ggtggacccc gttgagctgc cgaacttccg      60
ggactccccc gcgaccccct tcccagcttcc cgtccgctcc gccgcagcga ttgtctcggt     120
gggttgattc ggcacaaacc gcccgaccca ggggccggtg cgcgtgtgga aggggaagca     180
ctcccctcgt ggtcgcctgg aggtgcgctg gaggaggggg tgacataacc agggactcga     240
ggtccgccgt gggaatgatc cacgaactgc tcttggctct gagcgggtac cctgggtcca     300
ttttcacctg gaacaagcgg agtggcctgc aggtatcgca ggcttccct ttcctccacc      360
ccagtgagac cagtgtcctg aatcgactct gccggctcgg cacagactat attcgcttca     420
ctgagttcat tgaacagtac acgggccatg tgcaacagca ggatcaccat ccatctcaac     480
agggccaagg tgggttacat ggaatctacc tgcgggcctt ctgcacaggg ctggattctg     540
ttttgcagcc ttatcgccaa gcactgcttg atttggaaca agagttcctg ggtgatcccc     600
atctctccat atcacatgtc aactacttcc tagaccagtt ccagcttctt tttcctctg      660
tgatggttgt agtagaacaa attaaaagtc aaaagattca tggttgtcaa atcctggaaa     720
cagtctacaa acacagctgt gggggggttgc ctcctgttcg aagtgcactg gaaaaaatcc     780
tggccgtttg tcatgggggtc atgtataaac agctctcagc ctggatgctc catggactcc     840
tcttggacca gcatgaagaa ttcttttatca aacaggggcc atcttctggt aatgtcagtg     900
```

-continued

| | |
|---|---|
| cccagccaga agaggacgag gaggatctgg gcattggggg actgacagga aaacaactga | 960 |
| gagaactgca ggacttgcgc ctgattgagg aagagaacat gctggcacca tctctgaagc | 1020 |
| agttttccct acgagtggag attttgccat cctacattcc agtgagggtt gctgaaaaaa | 1080 |
| tcctatttgt tggagaatct gtccagatgt ttgagaatca aaatgtgaac ctgactagaa | 1140 |
| aaggatccat tttgaaaaac caggaagaca cttttgctgc agagctgcac cgtctcaagc | 1200 |
| agcagccact cttcagcttg gtggactttg aacaggtggt ggatcgcatt cgcagcactg | 1260 |
| tggctgagca tctctggaag ttgatggtag aagaatccga tttactgggt cagctgaaga | 1320 |
| tcattaaaga cttttacctt ctgggacgtg agaactgtt tcaggccttc attgacacag | 1380 |
| ctcaacacat gttgaaaaca ccacccactg cagtaactga gcatgatgtg aatgtggcct | 1440 |
| ttcaacagtc agcacacaag gtattgctag atgatgacaa ccttctccct ctgttgcact | 1500 |
| tgacaatcga gtatcacgga aaggagcaca agcagatgc tactcaggca agagaagggc | 1560 |
| cttctcggga aacttctccc cgggaagccc ctgcatctgg ctgggcagcc ctaggtcttt | 1620 |
| cctacaaagt acagtggcca ctacatattc tcttcacccc agctgtcctg gaaaagtaca | 1680 |
| atgttgtttt taagtactta ctgagtgtgc gccgggtgca agctgagctg cagcactgct | 1740 |
| gggcccctaca aatgcagcgc aagcacctca gtcgaacca gactgatgca atcaagtggc | 1800 |
| gcctaagaaa tcacatggca ttttggtgg ataatcttca gtactatctc caggtagatg | 1860 |
| tgttggagtc tcagttctcc cagctgcttc atcagatcaa ttctaccga actttgaaa | 1920 |
| gcatccgatt ggctcatgac cacttcctga gcaatttgct ggctcaatcc tttatccctat | 1980 |
| tgaaacctgt gtttcactgc ctgaatgaaa tcctagatct ctgtcacagt ttttgttcgc | 2040 |
| tggtcagtca gaacctaggc ccactggatg agcgtggagc cgcccagctg agcattctcg | 2100 |
| tgaagggctt tagccgccag tcttcactcc tgttcaagat tctctccagt gttcggaatc | 2160 |
| atcagatcaa ctcagatttg gctcaactac tgttacgact agattataac aaatactata | 2220 |
| cccaggctgg tggaactctg gcagtttcg ggatgtgaaa atttctggct cataaattga | 2280 |
| aataacagcc acgttcccaa ggttgtaaca gaagattcaa acatcccat tctagccaca | 2340 |
| cacaaataaa tatctgcggc ttagtgatag gactctacct tttctcctag aagcagttac | 2400 |
| tgaacatcca ggagtacaac tccttcccat cattcccatg tggaagggtc tctcccatca | 2460 |
| aggagaacat gtggcatctc tgatcccttta cattgagaac atttgttgga tatgttcatt | 2520 |
| tattcaatag tcatttattg agcacctact acgtaccttg gtactgttca agctgtggga | 2580 |
| gatacagcgg taaacaaaca atatagagca gaaagtt | 2617 |

<210> SEQ ID NO 16
<211> LENGTH: 667
<212> TYPE: PRT
<213> ORGANISM: Homo sapiens

<400> SEQUENCE: 16

Met Ile His Glu Leu Leu Leu Ala Leu Ser Gly Tyr Pro Gly Ser Ile
1               5                   10                  15

Phe Thr Trp Asn Lys Arg Ser Gly Leu Gln Val Ser Gln Asp Phe Pro
            20                  25                  30

Phe Leu His Pro Ser Glu Thr Ser Val Leu Asn Arg Leu Cys Arg Leu
        35                  40                  45

Gly Thr Asp Tyr Ile Arg Phe Thr Glu Phe Ile Glu Gln Tyr Thr Gly
    50                  55                  60

His Val Gln Gln Gln Asp His His Pro Ser Gln Gly Gln Gly Gly
65                  70                  75                  80

```
Leu His Gly Ile Tyr Leu Arg Ala Phe Cys Thr Gly Leu Asp Ser Val
                85                  90                  95
Leu Gln Pro Tyr Arg Gln Ala Leu Leu Asp Leu Glu Gln Glu Phe Leu
            100                 105                 110
Gly Asp Pro His Leu Ser Ile Ser His Val Asn Tyr Phe Leu Asp Gln
        115                 120                 125
Phe Gln Leu Leu Phe Pro Ser Val Met Val Val Glu Gln Ile Lys
130                 135                 140
Ser Gln Lys Ile His Gly Cys Gln Ile Leu Glu Thr Val Tyr Lys His
145                 150                 155                 160
Ser Cys Gly Gly Leu Pro Pro Val Arg Ser Ala Leu Glu Lys Ile Leu
                165                 170                 175
Ala Val Cys His Gly Val Met Tyr Lys Gln Leu Ser Ala Trp Met Leu
            180                 185                 190
His Gly Leu Leu Leu Asp Gln His Glu Glu Phe Phe Ile Lys Gln Gly
        195                 200                 205
Pro Ser Ser Gly Asn Val Ser Ala Gln Pro Glu Glu Asp Glu Glu Asp
210                 215                 220
Leu Gly Ile Gly Gly Leu Thr Gly Lys Gln Leu Arg Glu Leu Gln Asp
225                 230                 235                 240
Leu Arg Leu Ile Glu Glu Asn Met Leu Ala Pro Ser Leu Lys Gln
                245                 250                 255
Phe Ser Leu Arg Val Glu Ile Leu Pro Ser Tyr Ile Pro Val Arg Val
            260                 265                 270
Ala Glu Lys Ile Leu Phe Val Gly Glu Ser Val Gln Met Phe Glu Asn
        275                 280                 285
Gln Asn Val Asn Leu Thr Arg Lys Gly Ser Ile Leu Lys Asn Gln Glu
290                 295                 300
Asp Thr Phe Ala Ala Glu Leu His Arg Leu Lys Gln Gln Pro Leu Phe
305                 310                 315                 320
Ser Leu Val Asp Phe Glu Gln Val Val Asp Arg Ile Arg Ser Thr Val
                325                 330                 335
Ala Glu His Leu Trp Lys Leu Met Val Glu Glu Ser Asp Leu Leu Gly
            340                 345                 350
Gln Leu Lys Ile Ile Lys Asp Phe Tyr Leu Leu Gly Arg Gly Glu Leu
        355                 360                 365
Phe Gln Ala Phe Ile Asp Thr Ala Gln His Met Leu Lys Thr Pro Pro
370                 375                 380
Thr Ala Val Thr Glu His Asp Val Asn Val Ala Phe Gln Gln Ser Ala
385                 390                 395                 400
His Lys Val Leu Leu Asp Asp Asn Leu Leu Pro Leu Leu His Leu
                405                 410                 415
Thr Ile Glu Tyr His Gly Lys Glu His Lys Ala Asp Ala Thr Gln Ala
            420                 425                 430
Arg Glu Gly Pro Ser Arg Glu Thr Ser Pro Arg Glu Ala Pro Ala Ser
        435                 440                 445
Gly Trp Ala Ala Leu Gly Leu Ser Tyr Lys Val Gln Trp Pro Leu His
450                 455                 460
Ile Leu Phe Thr Pro Ala Val Leu Glu Lys Tyr Asn Val Val Phe Lys
465                 470                 475                 480
Tyr Leu Leu Ser Val Arg Arg Val Gln Ala Glu Leu Gln His Cys Trp
                485                 490                 495
Ala Leu Gln Met Gln Arg Lys His Leu Lys Ser Asn Gln Thr Asp Ala
            500                 505                 510
```

```
Ile Lys Trp Arg Leu Arg Asn His Met Ala Phe Leu Val Asp Asn Leu
        515                 520                 525

Gln Tyr Tyr Leu Gln Val Asp Val Leu Glu Ser Gln Phe Ser Gln Leu
        530                 535                 540

Leu His Gln Ile Asn Ser Thr Arg Asp Phe Glu Ser Ile Arg Leu Ala
545                 550                 555                 560

His Asp His Phe Leu Ser Asn Leu Leu Ala Gln Ser Phe Ile Leu Leu
            565                 570                 575

Lys Pro Val Phe His Cys Leu Asn Glu Ile Leu Asp Leu Cys His Ser
                580                 585                 590

Phe Cys Ser Leu Val Ser Gln Asn Leu Gly Pro Leu Asp Glu Arg Gly
        595                 600                 605

Ala Ala Gln Leu Ser Ile Leu Val Lys Gly Phe Ser Arg Gln Ser Ser
        610                 615                 620

Leu Leu Phe Lys Ile Leu Ser Ser Val Arg Asn His Gln Ile Asn Ser
625                 630                 635                 640

Asp Leu Ala Gln Leu Leu Leu Arg Leu Asp Tyr Asn Lys Tyr Tyr Thr
            645                 650                 655

Gln Ala Gly Gly Thr Leu Gly Ser Phe Gly Met
            660                 665

<210> SEQ ID NO 17
<211> LENGTH: 2635
<212> TYPE: DNA
<213> ORGANISM: Homo sapiens

<400> SEQUENCE: 17
aacaacaaaa ccggcgcgcc agcggtggcg caacggctct cgtccccgcc ctcctgctac      60
ctgtagtcgc ctgggccgcc cccggcccag ccctgccttg ccgccaccct gcgctgtcca     120
gactgagggg tcaggcggag agccgggccg cgcccttcgg tcagcttctc tccctttcac     180
ccgcgcctcc tcgcgagacc cggggctggg ccgtgccggt cgccgcgcag caggaaggga     240
gcggctgcca cggaaaacgc ctggccggac ggtgtggctg cggccctgc ctgggcgcgg      300 agggcggcgg tggcgggccc cgcggccttc tctcaggtac cccagtgccc gctgaccgcc     360
ctgagcggcc cagctgcttc cccgatccgc accgcggggc cgtggcgtag ggccttgtt     420 gcgttccagc ttgggggtcg cggtggggcg gggcagtgac cccgggccgg ccgttgtgcc     480
ctcatccctc ccaccttcc ttcgtatagc ttccttctc ctcacgacgg cctccacagt      540
ccggagcccg gcggagcccg gacctggcgg ggagagctgc ctccacggcc gggcacccag     600
accccaccgt cgcagtcgcc accacctcag tccatccttg gtaccggcaa tgggcttcgt     660
atcctccagt gcacttgtaa ctgacttgga cacggaatac taagaactca cttctgtcct     720
catcccagtc gcgccggcgg tgaccatctc ggctcttttg ggcttaactg ccgctcctct     780
ggactctgtc tgactttggg ggcaccatgg accaaagtgg gatggagatt cctgtgaccc     840
tcatcattaa agcaccgaat cagaaataca gtgaccagac tattagctgc ttcttgaact     900
ggaccgtggg gaaactaaaa acgcatctat ctaacgttta ccctagcaaa ccattgacga     960
aggatcagag attggtgtat tcgggcagac tgcttcccga tcatctgcag ctgaaagaca    1020
ttctcagaaa acaagatgag tatcatatgg ttcatctagt atgtacttct cggactcctc    1080
ccagttctcc aaaatccagc accaatagag aaagtcatga agcattggca tccagcagca    1140
attctagttc agatcattca ggatcaacaa ctccatcatc tggtcaagaa accttgtctt    1200
tagctgtggg ttcttcctca gaaggattga ggcagcgtac ccttccacaa gcacaaactg    1260
```

```
accaagcaca gagtcaccag tttccatatg taatgcaagg aaatgtagac aaccaatttc    1320
ctgggcaagc tgctccacct ggattcccag tgtatcccgc gtttagccca ctgcagatgc    1380
tatggtggca acagatgtat gctcatcagt attatatgca gtatcaagct gcagtttcag    1440
ctcaggccac atcaaatgtc aacccaaccc agcctactac ttcacagcct ctaaatttgg    1500
cacatgttcc tggagaagaa ccccaccag ctccaaacct agtgcccaa gaaaatcgac    1560 ccatgaatga gaatgttcaa atgaatgcac agggaggtcc agtactaaat gaagaagact    1620
tcaatcgaga ctggctagac tggatgtaca cgttctcacg agctgcgatt ctccttagca    1680
ttgtatactt ctattcttct tttagtcggt ttatcatggt aatgggagcc atgctactgg    1740
tttatttaca ccaagctgga tggtttcctt ttaggcaaga aggaggtcat cagcaggctc    1800
ccaacaataa tgccgaagtt aacaatgatg ggcaaaatgc aaacaacttg aacttgaag    1860 aaatggagcg tcttatggat gatgggcttg aagatgagag tggagaagat ggaggtgaag    1920
atgccagtgc aattcaaagg cctggattaa tggcttcagc ttggtctttc atcaccacct    1980
tctttacttc actaatacca gaggggcctc cccaggttgc caattgacct gaaaaactgt    2040
gccagctaca aggagggtct gacttcagga aagtggttta ataacagtg caatttcaaa    2100 aaaatttata actttctttt gatcatcatg tacagaggtg ttttttttct ttaggcttct    2160
catgcatatg aatattttaa gcacgaatgg actactaaat atctgagttt ttttttttt    2220 ttttttaaag atcctaacag aacatagcgt aacaatattg gtcttccagg tgttactcat    2280
ttcaattatg tgtagtatac caggacagac ctatttcat gtcttatttc tttaaagagc    2340
tgcttcattg gccgggcgcc atggctcacg tctgtagtcc cagcacttg ggaggccgag    2400 gcgggtgggt tacttgaggt caggagttcg agaccagcct ggcaaacatg gcgaaacccc    2460
atcttaacta aaaatacaaa aaattagcc gggtgtggtg tcacgcgcct gtaatcccag    2520
ctacttgggg ggctcaggca ggagaattgc ctgaacccag gaggcggagg ttgcagtgag    2580
ctgagattgg gccactgcac tccaccctgg gcgacagagt gagactcggt ctcag        2635
```

<210> SEQ ID NO 18
<211> LENGTH: 406
<212> TYPE: PRT
<213> ORGANISM: Homo sapiens

<400> SEQUENCE: 18

```
Met Asp Gln Ser Gly Met Glu Ile Pro Val Thr Leu Ile Ile Lys Ala
1               5                   10                  15

Pro Asn Gln Lys Tyr Ser Asp Gln Thr Ile Ser Cys Phe Leu Asn Trp
            20                  25                  30

Thr Val Gly Lys Leu Lys Thr His Leu Ser Asn Val Tyr Pro Ser Lys
        35                  40                  45

Pro Leu Thr Lys Asp Gln Arg Leu Val Tyr Ser Gly Arg Leu Leu Pro
    50                  55                  60

Asp His Leu Gln Leu Lys Asp Ile Leu Arg Lys Gln Asp Glu Tyr His
65                  70                  75                  80

Met Val His Leu Val Cys Thr Ser Arg Thr Pro Pro Ser Ser Pro Lys
                85                  90                  95

Ser Ser Thr Asn Arg Glu Ser His Glu Ala Leu Ala Ser Ser Ser Asn
            100                 105                 110

Ser Ser Ser Asp His Ser Gly Ser Thr Thr Pro Ser Ser Gly Gln Glu
        115                 120                 125

Thr Leu Ser Leu Ala Val Gly Ser Ser Glu Gly Leu Arg Gln Arg
    130                 135                 140
```

-continued

```
Thr Leu Pro Gln Ala Gln Thr Asp Gln Ala Gln Ser His Gln Phe Pro
145                 150                 155                 160

Tyr Val Met Gln Gly Asn Val Asp Asn Gln Phe Pro Gly Gln Ala Ala
                165                 170                 175

Pro Pro Gly Phe Pro Val Tyr Pro Ala Phe Ser Pro Leu Gln Met Leu
            180                 185                 190

Trp Trp Gln Gln Met Tyr Ala His Gln Tyr Tyr Met Gln Tyr Gln Ala
        195                 200                 205

Ala Val Ser Ala Gln Ala Thr Ser Asn Val Asn Pro Thr Gln Pro Thr
    210                 215                 220

Thr Ser Gln Pro Leu Asn Leu Ala His Val Pro Gly Glu Glu Pro Pro
225                 230                 235                 240

Pro Ala Pro Asn Leu Val Ala Gln Glu Asn Arg Pro Met Asn Glu Asn
                245                 250                 255

Val Gln Met Asn Ala Gln Gly Gly Pro Val Leu Asn Glu Glu Asp Phe
                260                 265                 270

Asn Arg Asp Trp Leu Asp Trp Met Tyr Thr Phe Ser Arg Ala Ala Ile
            275                 280                 285

Leu Leu Ser Ile Val Tyr Phe Tyr Ser Ser Phe Ser Arg Phe Ile Met
        290                 295                 300

Val Met Gly Ala Met Leu Leu Val Tyr Leu His Gln Ala Gly Trp Phe
305                 310                 315                 320

Pro Phe Arg Gln Glu Gly Gly His Gln Gln Ala Pro Asn Asn Asn Ala
                325                 330                 335

Glu Val Asn Asn Asp Gly Gln Asn Ala Asn Asn Leu Glu Leu Glu Glu
                340                 345                 350

Met Glu Arg Leu Met Asp Asp Gly Leu Glu Asp Glu Ser Gly Glu Asp
                355                 360                 365

Gly Gly Glu Asp Ala Ser Ala Ile Gln Arg Pro Gly Leu Met Ala Ser
        370                 375                 380

Ala Trp Ser Phe Ile Thr Thr Phe Phe Thr Ser Leu Ile Pro Glu Gly
385                 390                 395                 400

Pro Pro Gln Val Ala Asn
                405
```